(12) United States Patent
Lipinski et al.

(10) Patent No.: US 12,012,602 B2
(45) Date of Patent: Jun. 18, 2024

(54) RIBOSWITCH MODULATED GENE THERAPY FOR RETINAL DISEASES

(71) Applicant: THE MEDICAL COLLEGE OF WISCONSIN, INC., Milwaukee, WI (US)

(72) Inventors: Daniel M. Lipinski, Milwaukee, WI (US); Chris A. Reid, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 1168 days.

(21) Appl. No.: 16/492,878

(22) PCT Filed: Mar. 9, 2018

(86) PCT No.: PCT/US2018/021719
§ 371 (c)(1),
(2) Date: Sep. 10, 2019

(87) PCT Pub. No.: WO2018/165536
PCT Pub. Date: Sep. 13, 2018

(65) Prior Publication Data
US 2020/0063137 A1    Feb. 27, 2020

Related U.S. Application Data

(60) Provisional application No. 62/469,705, filed on Mar. 10, 2017.

(51) Int. Cl.
*C12N 15/115* (2010.01)
*A61K 48/00* (2006.01)
*C12N 15/67* (2006.01)

(52) U.S. Cl.
CPC .......... *C12N 15/115* (2013.01); *A61K 48/005* (2013.01); *A61K 48/0075* (2013.01); *C12N 15/67* (2013.01); *C12N 2310/141* (2013.01); *C12N 2310/16* (2013.01); *C12N 2310/3519* (2013.01); *C12N 2320/50* (2013.01); *C12N 2750/14143* (2013.01); *C12N 2830/00* (2013.01)

(58) Field of Classification Search
None
See application file for complete search history.

(56) References Cited

U.S. PATENT DOCUMENTS

| | | |
|---|---|---|
| 8,158,595 B2 | 4/2012 | Galloway |
| 8,603,996 B2 | 12/2013 | Galloway |
| 8,865,667 B2 | 10/2014 | Smolke |
| 9,040,495 B2 | 5/2015 | Smolke |
| 9,315,862 B2 | 4/2016 | Smolke |
| 10,501,811 B2 | 12/2019 | Yoshida et al. |
| 10,620,109 B2 | 4/2020 | Saito et al. |
| 2002/0166132 A1 | 11/2002 | Scherman |
| 2006/0088864 A1* | 4/2006 | Smolke ............ C12Q 1/6897 435/325 |
| 2007/0089186 A1* | 4/2007 | Huang ............ C12N 15/8286 800/278 |
| 2008/0199961 A1 | 8/2008 | Rasko |
| 2009/0210952 A1 | 8/2009 | Wu et al. |
| 2010/0152212 A1 | 6/2010 | Breaker |
| 2010/0184810 A1 | 7/2010 | Breaker |
| 2010/0286082 A1 | 11/2010 | Breaker |
| 2012/0321647 A1 | 12/2012 | Breaker |
| 2013/0012527 A1 | 1/2013 | Breaker |
| 2013/0039971 A1 | 2/2013 | Dejneka |
| 2013/0143955 A1 | 6/2013 | Breaker |
| 2015/0024024 A1 | 1/2015 | Tao |
| 2017/0051290 A1* | 2/2017 | Byrne ............ C12N 15/1136 |
| 2017/0370821 A1 | 12/2017 | Saito et al. |
| 2018/0100203 A1 | 4/2018 | Yoshida et al. |
| 2020/0056248 A1 | 2/2020 | Yoshida et al. |

FOREIGN PATENT DOCUMENTS

| | | |
|---|---|---|
| AU | 2012/265582 A1 | 1/2013 |
| CN | 102727513 A | 10/2012 |
| CN | 102895673 A | 1/2013 |
| CN | 103068863 A | 4/2013 |
| CN | 106074591 A | 7/2013 |
| CN | 105431204 A | 2/2022 |
| WO | 2006/021817 A2 | 3/2006 |
| WO | 2011/119871 A1 | 9/2011 |
| WO | 2011/157777 A1 | 12/2011 |
| WO | 2012/087983 A1 | 6/2012 |
| WO | 2015/006734 A1 | 1/2015 |
| WO | 2017/042239 A1 | 3/2017 |

OTHER PUBLICATIONS

Ricci, V., Ronzoni, M., & Fabozzi, T. (2015). Aflibercept a new target therapy in cancer treatment: a review. Critical Reviews in Oncology/Hematology, 96(3), 569-576. (Year: 2015).*
C. Beisel et al., Nucleic Acids Research, 2011, vol. 30, No. 7, 2981-2994.
Boye, S. E., et al. "A comprehensive review of retinal gene therapy." Molecular therapy 21.3 (2013): 509-519.
Chang, A. L., et al. "Synthetic RNA switches as a tool for temporal and spatial control over gene expression." Current opinion in biotechnology 23.5 (2012): 679-688.
Enslow, R., et al. "Association of anti-VEGF injections with progression of geographic atrophy." Ophthalmology and eye diseases 8 (2016): OED-S38863.
Ferguson, L. R.. Regulation of gene expression for therapy of age related macular degeneration. Diss. University of Florida, 2009.

(Continued)

*Primary Examiner* — Neil P Hammell
*Assistant Examiner* — Khaleda B Hasan
(74) *Attorney, Agent, or Firm* — Quarles & Brady LLP

(57) ABSTRACT

The present invention provides constructs comprising modified riboswitches to regulate expression of a transgene within a subject. Methods of treating a disease, specifically an eye disease, are also contemplated.

21 Claims, 35 Drawing Sheets
(22 of 35 Drawing Sheet(s) Filed in Color)
Specification includes a Sequence Listing.

(56) References Cited

OTHER PUBLICATIONS

International Searching Authority, International Search Report and Written Opinion for application PCT/US2018/021719, dated Jul. 3, 2018, 14 pages.
Martin, D. F., et al. "Ranibizumab and bevacizumab for treatment of neovascular age-related macular degeneration: two-year results." Ophthalmology 119.7 (2012): 1388-1398.
Rottiers, V. et al. "MicroRNAs in metabolism and metabolic disorders." Nature reviews Molecular cell biology 13.4 (2012): 239.
Beilstein, K., et al. Conditional Control of Mammalian Gene Expression by Tetracycline-Dependent Hammerhead Ribozymes. ACS synthetic biology 4, 526-534 (2015).
Chen, Y. Y., et al. Genetic control of mammalian T-cell proliferation with synthetic RNA regulatory systems. Proceedings of the National Academy of Sciences of the United States of America 107, 8531-8536, https://doi.org/10.1073/ pnas.1001721107 (2010).
Win, M. N. et al. "A modular and extensible RNA-based gene-regulatory platform for engineering cellular function." Proceedings of the National Academy of Sciences 104.36 (2007): 14283-14288.
Beisel, Chase L. et al., "Design of small molecule-responsive microRNAs based on structural requirements for Drosha processing", Nucleic Acids Research, 2011, vol. 39, No. 7, 2981-2994.
Doench, John G. et al., "siRNAs can function as miRNAs", Genes & Development, 17:438-442, downloaded from genesdev.cship.org on Sep. 25, 2022.
Miki, Kenji et al., "Efficient Detection and Purification of Cell Populations Using Synthetic MicroRNA Switches", Cell Stem Cell 16, 699-711, Jun. 4, 2015.
Drewry, M. D., et al. "Differentially expressed microRNAs in the aqueous humor of patients with exfoliation glaucoma or primary open-angle glaucoma." Human molecular genetics. 27(7):1263-1275. Feb. 2018.
Guo, R. et al. "Relationship between the pathogenesis of glaucoma and miRNA." Opthalmic research. 57(3):194-199. Jan. 2017.
Guzman-Aranguez, A., et al. "Small-interfering RNAs (siRNAs) as a promising tool for ocular therapy: siRNA for ocular therapy." British Journal of Pharmacology, 170(4): 730-747. Oct. 2013.
Ketzer, P., et al. "Artificial riboswitches for gene expression and replication control of DNA and RNA viruses." Proceedings of the national academy of sciences. 111(5):E554-E562. Jan. 2014.
Kim, M. et al. "Angiogenesis in glaucoma filtration surgery and neovascular glaucoma: a review." Survey of Opthamology. 60(6):524-535, Nov. 2015.
Agrawal S., et al. "MicroRNA signature and funtional in retinal neurovascularization." World J Biol Chem. 5(1):1-11. Feb. 2014.
Supplementary European Search Report Issued for European Application No. EP 18/764686, dated Nov. 30, 2020, 16 pages.
Doench, J. G., et al. "siRNAs can function as miRNAs." Genes and Development. 17:438-442. 2003.

* cited by examiner

SLIM switch design

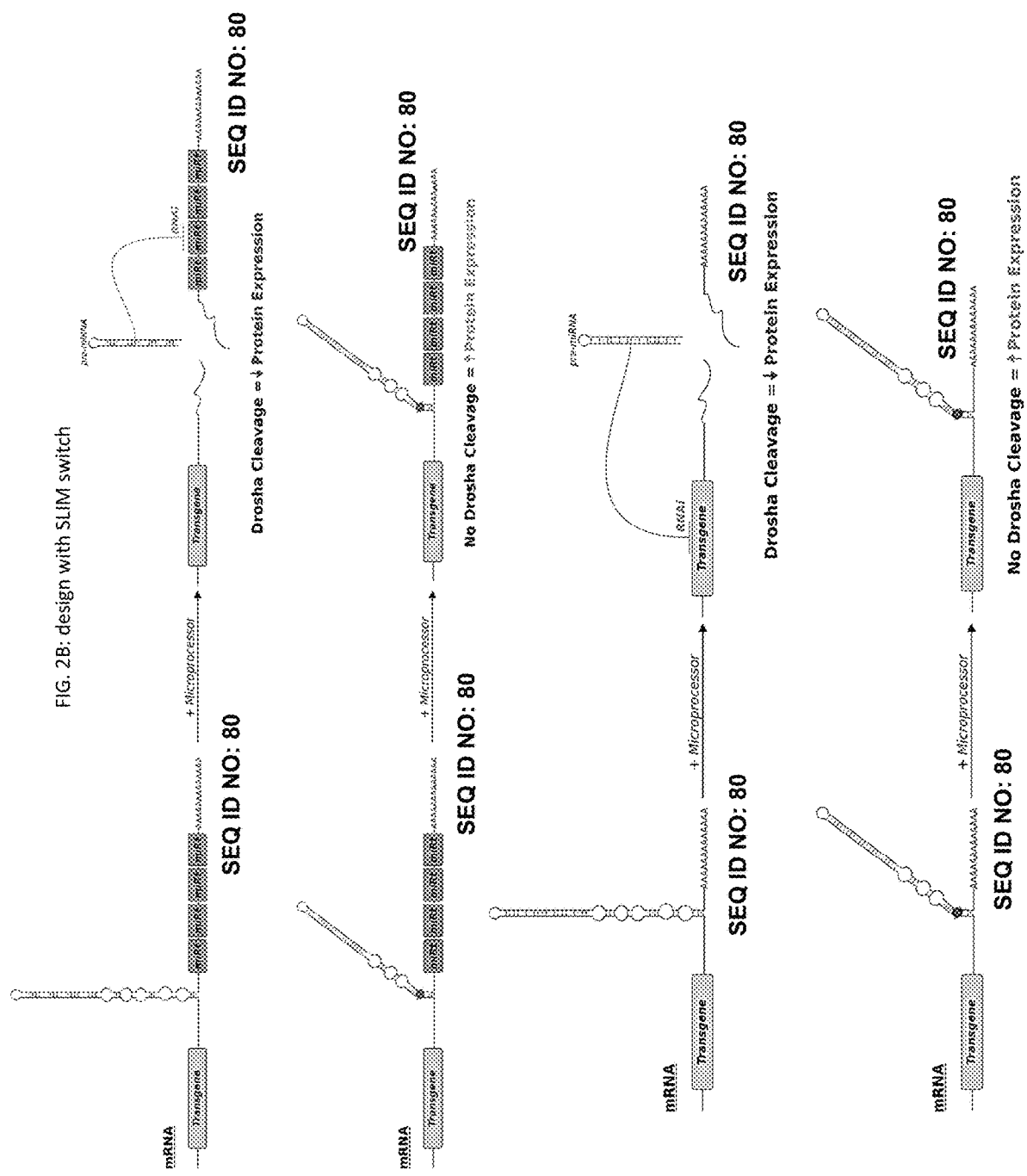
FIG. 2B: design with SLIM switch

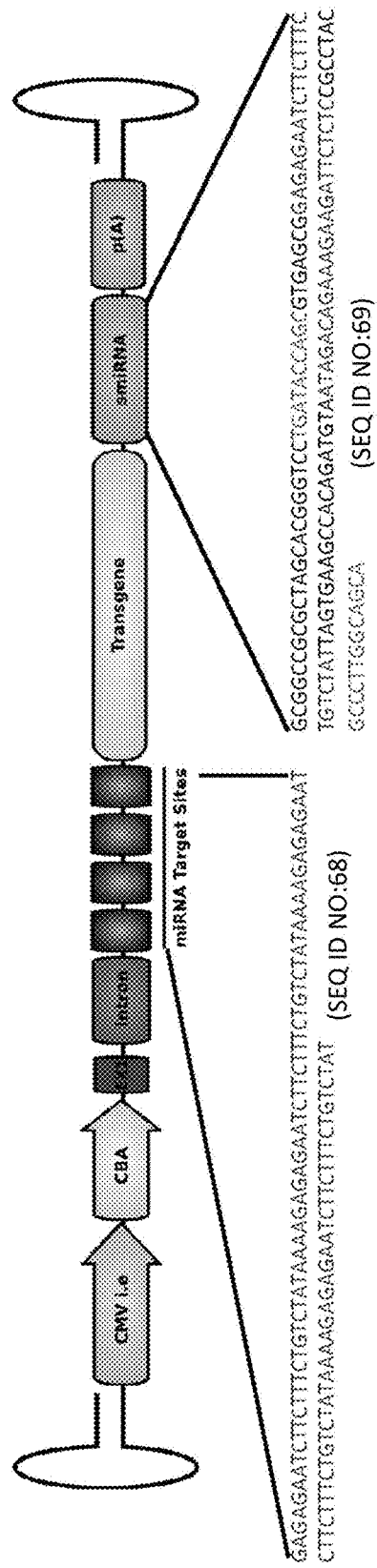
FIG. 2C (rAAV vector encoding Aflibecept and SLIM switch)

FIG. 3
ON type Aptamer

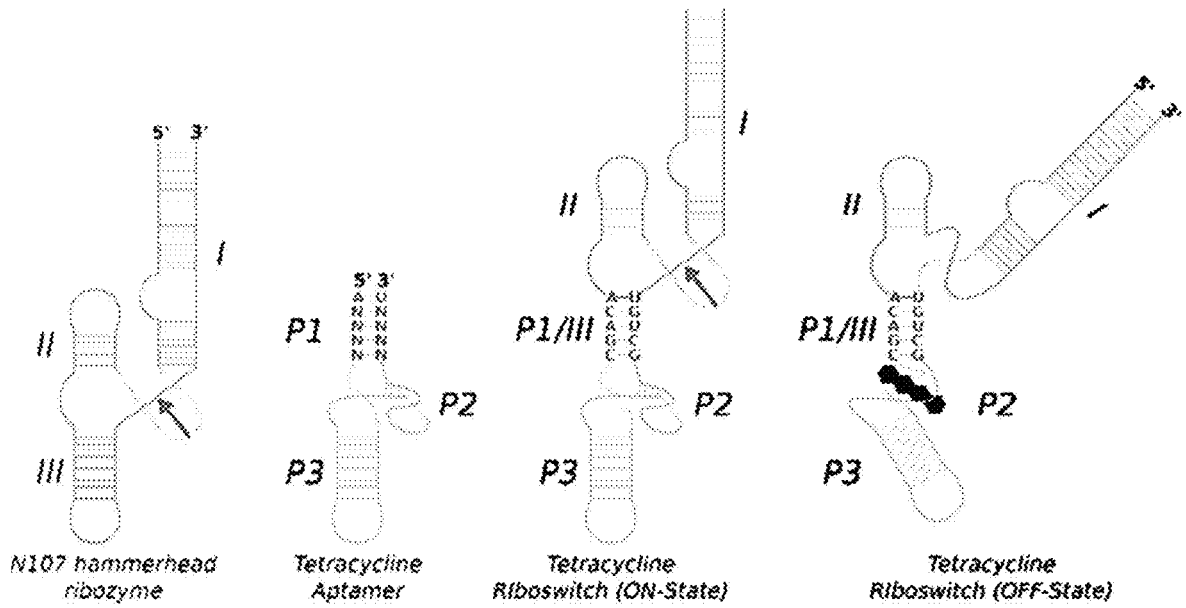

FIG. 4 rAAV smCBA-Aflibercept-Theo-SLIM Construct:

| Element | Color |
| --- | --- |
| switchable miRNA | Red (SEQ ID. NO:1) |
| miRNA Target Sites | Light Blue (SEQ ID. NO:2) |
| Inverted Terminal Repeats | Bold (SEQ ID. NO:3) |
| bGH Poly(A) | Teal Highlight (SEQ ID. NO:4) |
| Chimeric Intron | Orange (SEQ ID. NO:5) |
| Chicken Beta Actin Promoter | Purple (SEQ ID. NO:6) |
| CMV enhancer | Green (SEQ ID. NO:7) |
| cDNA Aflibercept | Yellow Highlight (SEQ ID. NO:8) |

FIG. 5

GGTTGGCCACTCCCTCTCTGCGCGCTCGCTCGCTCACTGAGGCCGGGCGACCAAAGGTCGCCCGACGCCCGGGCTTTGCCCG
GGCGGCCTCAGTGAGCGAGCGAGCGCGCAGAGAGGGAGTGGCCAACTCCATCACTAGGGGTTCCTAGATCTGAATTCGGTA
CCCCTAGTTATTAATAGTAATCAATTACGGGGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGACGTATGTTCCCATAGTAACGCCAATAGGGA
CTTTCCATTGACGTCAATGGGTGGACTATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGACCTTATGGGACTTTCCTACTTGGCAGT
ACATCTACGTATTAGTCATCGCTATTACCATGGTCGAGGTGAGCCCCACGTTCTGCTTCACTCTCCCCATCTCCCCCCCCTCCCCA
CCCCCAATTTTGTATTTATTTATTTTTTAATTATTTTGTGCAGCGATGGGGCGGGGGGGGGGGGGGCGCGCGCCAGGCG
GGGCGGGGCGGGGCGAGGGGCGGGGCGGGGCGAGGCGGAGAGGTGCGGCGGCAGCCAATCAGAGCGGCGCGCTCCGAA
AGTTTCCTTTTATGGCGAGGCGGCGGCGGCGGCGGCCCTATAAAAAGCGAAGCGCGCGGCGGGCGGGAGTCGCTGCGACGC
TGCCTTCGCCCCGTGCCCCGCTCCGCCGCCGCCTCGCGCCGCCCGCCCCGGCTCTGACTGACCGCGTTACTCCCACAGGTGAGC
GGGCGGGACGGCCCTTCTCCTCCGGGCTGTAATTAGCGCTTGGTTTAATGACGGCTTGTTTCTTTTCTGTGGCTGCGTGAAAGC
CTTGAGGGGCTCCGGGAGCTAGAGCCTCTGCTAACCATGTTCATGCCTTCTTCTTTTTCCTACAGCTCCTGGGCAACGTGCTGG
TTATTGTGCTGTCTCATCATTTTGGCAAAGAATTCCTCGAAGATCTAGGCAACGCGTATTGGGATCTCGAGGCGGCCGCGCCGC
CACCCTAGCGAGAGAATCTTCTTTCTGTCTATAAAGAGAGAATCTTCTTTCTGTCTATAAAGAGAGAATCTTCTTTCTGTCTA
TAAAGAGAGAATCTTCTTTCTGTCTATGTCGACCCTGCAATGGTATCATATTGGGACACAGGAGTCCTCCTGTGCGCCCTTTT
GAGCTGTCTTTTGCTGACGGGTTCTTCTTCAGGTTCTGATACCGGGAGACCATTCGTTGAAATGTATAGTGAGATACCCGAAAT
TATACATATGACTGAAGGGCGCGAGCTCGTCATACCCTGTCGGGTAACAAGTCCAAACATAACAGTGACCCTGAAGAAGTTCC
CTTTGGATACTCTCATTCCCGACGGGAAGCGAATAATTTGGGACTCAAGGAAGGGATTTATCATATCTAATGCAACATATAAG
GAAATAGGGCTCCTCACATGCGAAGCCACAGTCAACGGGCACCTCTACAAAACTAATTACCTGACCCATCGACAGACAAATAC
CATCATTGATGTGGTTCTGAGTCCATCTCATGGAATAGAGTTGAGTGTAGGGGAGAAGCTTGTTCTCAATTGCACAGCTAGAA
CCGAGTTGAACGTGGGTATCGATTTTAACTGGGAATACCCATCTAGTAAGCACCAACACAAAAAACTTGTCAATCGAGATTTG
AAAACTCAATCTGGTAGCGAGATGAAAAAGTTCCTGTCAACTCTTACAATCGATGGCGTGACCCGGAGTGATCAAGGATTGTA
TACCTGCGCCGCCAGCTCTGGCCTGATGACTAAAAAGAACAGCACCTTTGTACGAGTGCATGAAAAGGATAAGACTCATACAT
GCCCTCCTTGTCCCGCTCCAGAGCTGCTGGGAGGTCCCAGTGTTTTCCTCTTCCCACCAAAGCCCAAAGATACTCTGATGATTAG
CCGGACCCCTGAGGTGACTTGCGTCGTGGTGGATGTTTCACATGAAGATCAGAAGTGAAGTTCAATTGGTACGTTGATGGTG
TGGAGGTACACAATGCCAAGACTAAACCTCGGGAGGAACAGTATAACAGCACTTACAGAGTTGTCAGCGTACTCACAGTGCTT
CATCAGGACTGGTTGAATGGTAAGGAGTATAAGTGCAAAGTGAGTAATAAGGCTCTGCCAGCACCCATAGAGAAGACAATCT
CAAAGGCCAAAGGCCAGCCCCGAGAACCACAAGTATACACACTGCCACCTAGTAGAGACGAGTTGACAAAAAATCAGGTCAG
CCTCACCTGTCTCGTGAAAGGCTTCTACCCTAGCGACATTGCCGTAGAATGGGAAAGCAACGGGCAACCAGAAAACAATTATA
AGACAACACCTCCCGTTCTCGATAGTGACGGAAGTTTCTTCCTGTATAGCAAACTTACCGTGGATAAATCAAGATGGCAGCAA
GGTAATGTGTTTAGCTGTTCAGTAATGCACGAAGCTCTGCATAACCACTACACCCAAAAATCTTTGTCTCTGTCTCCAGGGTGA
GCGTATCAGCAGGTCCCATAAGCTTTCGACAATTAACGAGTGTGTACTCGTTCTATCATCTCACAGTTAAAGTCGGGAGAATAG
GAGCCGCACGGGTCCTGATACCAGCGTGAGCGGAGAGAATCTTCTTTCTGTCTATTAGTGAAGCCACAGATGTAATAGACAGA
AAGAAGATTCTCTCCGCCTACGCCCTTGGCAGCACCGTACGGTTCGATCAGCTTATTGGTACATGATAAGTCTCAGGCATCGTA
CGATGTCGACCTGCAGGAGTCGGTCGACTAGAGCTCGCTGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGGGAAGACAATAGCAGGC
ATGCTGGGGAGAGATCTAGGAACCCCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCGAGCGCGCAGAGAGGGAGTGGCCA
ACC (SEQ ID NO:9)

C57BL6/J mouse injected intravitreally with $1.0 \times 10^{10}$ vector genomes(vg) of rAAV2.smCBA-hGFP-3x-L2Bulge9. (A) Pre-treatment retinal imaging 4 weeks post injection. (B) Fluorescent imaging two hours post-gavage @ 10mg/kg of theophylline (activating ligand).

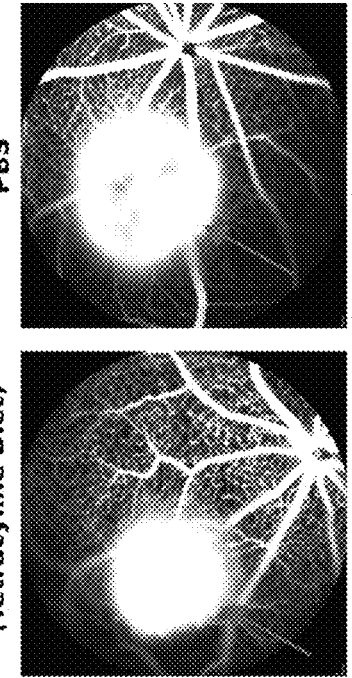
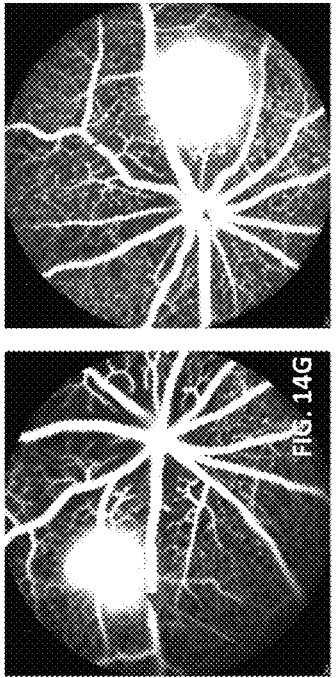
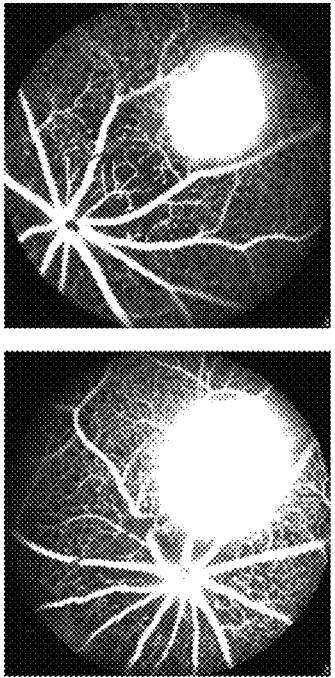
FIG. 14A smCBA-Eylea (non-inducible)
FIG. 14B smCBA-Eylea-1x-TC45 (Standard Diet)
FIG. 14C smCBA-Eylea-1x-TC45 (Tetracyline Diet)
FIG. 14D PBS
FIG. 14E, FIG. 14F, FIG. 14G, FIG. 14H
FIG. 14I, FIG. 14J, FIG. 14K, FIG. 14L

FIG. 16

*<u>Recombinant VEGF inhibitor cDNA (reverse engineered from Elyea protein sequence) with synthetic nerve growth factor secretion signal (SEQ ID NO:18)</u>*

**XATGTCCATGTTGTTCTACACTCTGATCACAGCTTTTCTGATCGGCATACAGGCGGAACC
ACACTCAGTCTGATACCGGGAGACCATTCGTTGAAATGTATAGTGAGATACCCGAAATTA
TACATATGACTGAAGGGCGCGAGCTCGTCATACCCTGTCGGGTAACAAGTCCAAACATA
ACAGTGACCCTGAAGAAGTTCCCTTTGGATACTCTCATTCCCGACGGGAAGCGAATAATT
TGGGACTCAAGGAAGGGATTTATCATATCTAATGCAACATATAAGGAAATAGGGCTCCTC
ACATGCGAAGCCACAGTCAACGGGCACCTCTACAAAACTAATTACCTGACCCATCGACA
GACAAATACCATCATTGATGTGGTTCTGAGTCCATCTCATGGAATAGAGTTGAGTGTAGG
GGAGAAGCTTGTTCTCAATTGCACAGCTAGAACCGAGTTGAACGTGGGTATCGATTTTAA
CTGGGAATACCCATCTAGTAAGCACCAACACAAAAAACTTGTCAATCGAGATTTGAAAAC
TCAATCTGGTAGCGAGATGAAAAAGTTCCTGTCAACTCTTACAATCGATGGCGTGACCCG
GAGTGATCAAGGATTGTATACCTGCGCCGCCAGCTCTGGCCTGATGACTAAAAAGAACA
GCACCTTTGTACGAGTGCATGAAAAGGATAAGACTCATACATGCCCTCCTTGTCCCGCTC
CAGAGCTGCTGGGAGGTCCCAGTGTTTTCCTCTTCCCACCAAAGCCCAAAGATACTCTGA
TGATTAGCCGGACCCCTGAGGTGACTTGCGTCGTGGTGGATGTTTCACATGAAGATCCA
GAAGTGAAGTTCAATTGGTACGTTGATGGTGTGGAGGTACACAATGCCAAGACTAAACC
TCGGGAGGAACAGTATAACAGCACTTACAGAGTTGTCAGCGTACTCACAGTGCTTCATC
AGGACTGGTTGAATGGTAAGGAGTATAAGTGCAAAGTGAGTAATAAGGCTCTGCCAGCA
CCCATAGAGAAGACAATCTCAAAGGCCAAAGGCCAGCCCCGAGAACCACAAGTATACA
CACTGCCACCTAGTAGAGACGAGTTGACAAAAAATCAGGTCAGCCTCACCTGTCTCGTG
AAAGGCTTCTACCCTAGCGACATTGCCGTAGAATGGGAAAGCAACGGGCAACCAGAAA
ACAATTATAAGACAACACCTCCCGTTCTCGATAGTGACGGAAGTTTCTTCCTGTATAGCA
AACTTACCGTGGATAAATCAAGATGGCAGCAAGGTAATGTGTTTAGCTGTTCAGTAATGC
ACGAAGCTCTGCATAACCACTACACCCAAAAATCTTTGTCTCTGTCTCCAGGTGA**AAAC
AAACAAAX

X = positions for SLIM regulatory elements (SLIM Sequences in FIG. 18)

<u>Complete AAV expression cassette for SLIM EYLEA (SEQ ID NO:19)</u>

GGTTGGCCACTCCCTCTCTGCGCGCTCGCTCGCTCACTGAGGCCGGGCGACCAAAGGTC
GCCCGACGCCCGGGCTTTGCCCGGGCGGCCTCAGTGAGCGAGCGAGCGCGCAGAGAGG
GAGTGGCCAACTCCATCACTAGGGGTTCCTAGATCTGAATTCGGTACCCCTAGTTATTAAT
AGTAATCAATTACGGGGTCATTAGTTCATAGCCCATATATGGAGTTCCGCGTTACATAACTT
ACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGACTATT
TACGGTAAACTGCCCACTTGGCAGTACATCAAGTGTATCATATGCCAAGTACGCCCCCTAT
TGACGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTCGAGGTGAGC
CCCACGTTCTGCTTCACTCTCCCCATCTCCCCCCCCTCCCCACCCCCAATTTTGTATTTATT
TATTTTTTAATTATTTTGTGCAGCGATGGGGGCGGGGGGGGGGGGGGCGCGCGCCAG
GCGGGGCGGGGCGGGGCGAGGGGCGGGGCGGGGCGAGGCGGAGAGGTGCGGCGGCA
GCCAATCAGAGCGGCGCGCTCCGAAAGTTTCCTTTTATGGCGAGGCGGCGGCGGCGGCG
GCCCTATAAAAAGCGAAGCGCGCGGCGGGCGGGAGTCGCTGCGACGCTGCCTTCGCCCC

FIG. 16 (continued)

GTGCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGTTTA
ATGACGGCTTGTTTCTTTTCTGTGGCTGCGTGAAAGCCTTGAGGGGCTCCGGGAGCTAGA
GCCTCTGCTAACCATGTTCATGCCTTCTTCTTTTTCCTACAGCTCCTGGGCAACGTGCTGG
TTATTGTGCTGTCTCATCATTTTGGCAAAGAATTCCTCGAAGATCTAGGCAACGCGTCTCGA
GGCGGCCGCCGCCACCXATGGTATCATATTGGGACACAGGAGTCCTCCTGTGCGCCCTT
**TTGAGCTGTCTTTTGCTGACGGGTTCTTCTTCAGGTTCTGATACCGGGAGACCATTCGTTG
AAATGTATAGTGAGATACCCGAAATTATACATATGACTGAAGGGCGCGAGCTCGTCATA
CCCTGTCGGGTAACAAGTCCAAACATAACAGTGACCCTGAAGAAGTTCCCTTTGGATACT
CTCATTCCCGACGGGAAGCGAATAATTTGGGACTCAAGGAAGGGATTTATCATATCTAAT
GCAACATATAAGGAAATAGGGCTCCTCACATGCGAAGCCACAGTCAACGGGCACCTCTA
CAAAACTAATTACCTGACCCATCGACAGACAAATACCATCATTGATGTGGTTCTGAGTCC
ATCTCATGGAATAGAGTTGAGTGTAGGGGAGAAGCTTGTTCTCAATTGCACAGCTAGAAC
CGAGTTGAACGTGGGTATCGATTTTAACTGGGAATACCCATCTAGTAAGCACCAACACAA
AAAACTTGTCAATCGAGATTTGAAAACTCAATCTGGTAGCGAGATGAAAAAGTTCCTGTC
AACTCTTACAATCGATGGCGTGACCCGGAGTGATCAAGGATTGTATACCTGCGCCGCCA
GCTCTGGCCTGATGACTAAAAAGAACAGCACCTTTGTACGAGTGCATGAAAAGGATAAG
ACTCATACATGCCCTCCTTGTCCCGCTCCAGAGCTGCTGGGAGGTCCCAGTGTTTTCCTC
TTCCCACCAAAGCCCAAAGATACTCTGATGATTAGCCGGACCCCTGAGGTGACTTGCGT
CGTGGTGGATGTTTCACATGAAGATCCAGAAGTGAAGTTCAATTGGTACGTTGATGGTGT
GGAGGTACACAATGCCAAGACTAAACCTCGGGAGGAACAGTATAACAGCACTTACAGA
GTTGTCAGCGTACTCACAGTGCTTCATCAGGACTGGTTGAATGGTAAGGAGTATAAGTGC
AAAGTGAGTAATAAGGCTCTGCCAGCACCCATAGAGAAGACAATCTCAAAGGCCAAAGG
CCAGCCCCGAGAACCACAAGTATACACACTGCCACCTAGTAGAGACGAGTTGACAAAAA
ATCAGGTCAGCCTCACCTGTCTCGTGAAAGGCTTCTACCCTAGCGACATTGCCGTAGAAT
GGGAAAGCAACGGGCAACCAGAAACAATTATAAGACAACACCTCCCGTTCTCGATAGT
GACGGAAGTTTCTTCCTGTATAGCAAACTTACCGTGGATAAATCAAGATGGCAGCAAGGT
AATGTGTTTAGCTGTTCAGTAATGCACGAAGCTCTGCATAACCACTACACCCAAAAATCT
TTGTCTCTGTCTCCAGGGTGA**GCGGCCGCATCGGCTAGCXAAGCTTCCTGCAGGAGTCGG
TCGACTAGAGCTCGCTGATCAGCCTCGACTGTGCCTTCTAGTTGCCAGCCATCTGTTGTTT
GCCCCTCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCTGGGGAGATC
TAGGAACCCCTAGTGATGGAGTTGGCCACTCCCTCTCTGCGCGCTCGCTCGCTCACTGAG
GCCGCCCGGGCAAAGCCCGGGCGTCGGGCGACCTTTGGTCGCCCGGCCTCAGTGAGCG
AGCGAGCGCGCAGAGAGGGAGTGGCCAACC (bold sequence: SEQ ID NO:20)

X = positions for SLIM regulatory elements (see FIGS. 18-19)

FIG. 18

SLIM SEQUENCES
6S-Folinic Acid-responsive miRNA Switches (Eylea CDS target)
6s-Folinic Acid Aptamer
siRNA #1
Complementary Strand

SLIM switch for Target 1 (SEQ ID NO:21)
GAACGCCTCCTAACGTCTGGTCACGACCCTGCGTGAGCGACCCCATTGTTCAGGTTTGTA
TTCTTTTGGCCACTGACTGAGAATACAAATGAACAATGGGGGCGCCTACGCAGCCCCTCG
AAATCACGAGGGAGACGAGATAAGGGGGCGTTT

SLIM switch for Target 2 (SEQ ID NO:22)
GAACGCCTCCTAACGTCTGGTCACGACCCTGCGTGAGCGACCCTGAGTTCCTTCCCTAAA
TACTTTTGGCCACTGACTGAGTATTTAGGAGGAACTCAGGGGGGCGCCTACGCAGCCCC
TCGAAATCACGAGGGAGACGAGATAAGGGGGCGTTT

SLIM switch for Target 3 (SEQ ID NO:23)
GAACGCCTCCTAACGTCTGGTCACGACCCTGCGTGAGCGACCAAGAGTTAACGTGTCGA
TCTCTTTTGGCCACTGACTGAGAGATCGACGTTAACTCTTGGGGGCGCCTACGCAGCCCC
TCGAAATCACGAGGGAGACGAGATAAGGGGGCGTTT

SLIM switch for Target 4 (SEQ ID NO:24)
GAACGCCTCCTAACGTCTGGTCACGACCCTGCGTGAGCGACCCTTCCCTAAATAGTATAG
ATCTTTTGGCCACTGACTGAGATCTATACTTTAGGGAAGGGGGCGCCTACGCAGCCCCT
CGAAATCACGAGGGAGACGAGATAAGGGGGCGTTT

SLIM switch for Target 5 (SEQ ID NO:25)
GAACGCCTCCTAACGTCTGGTCACGACCCTGCGTGAGCGACCGTGTCGATCTTGGCTCA
ACTCTTTTGGCCACTGACTGAGCGTGTCGATTGGCTCAACTGGGGCGCCTACGCAGCCCC
TCGAAATCACGAGGGAGACGAGATAAGGGGGCGTTT

Theophylline-responsive miRNA Switches (Eylea CDS target)
Theophylline Aptamer
siRNA #1
Complementary Strand

SLIM switch for Target 1 (SEQ ID NO:26)
GAACGCCTCCTTGATACCAGCTGCGTGAGCGACCCCATTGTTCAGGTTTGTATTCTTTTGG
CCACTGACTGAGAATACAAATGAACAATGGGGGCGCCTACGCGCCCTTGGCAGCAAGGG
GGCGTTT

SLIM switch for Target 2 ((SEQ ID NO:27)
GAACGCCTCCTTGATACCAGCTGCGTGAGCGACCCTGAGTTCCTTCCCTAAATACTTTTG
GCCACTGACTGAGTATTTAGGAGGAACTCAGGGGGGCGCCTACGCGCCCTTGGCAGCAA
GGGGGCGTTT

FIG. 18 (continued)

SLIM switch for Target 3 ((SEQ ID NO:28)
GAACGCCTCCTTGATACCAGCTGCGTGAGCGACCAAGAGTTAACGTGTCGATCTCTTTTG
GCCACTGACTGAGAGATCGACGTTAACTCTTGGGGGCGCCTACGCGCCCTTGGCAGCAA
GGGGGCGTTT

SLIM switch for Target 4 (SEQ ID NO:29)
GAACGCCTCCTTGATACCAGCTGCGTGAGCGACCCTTCCCTAAATAGTATAGATCTTTTG
GCCACTGACTGAGATCTATACTTTAGGGAAGGGGGCGCCTACGCGCCCTTGGCAGCAA
GGGGGCGTTT

SLIM switch for Target 5 (SEQ ID NO:30)
GAACGCCTCCTTGATACCAGCTGCGTGAGCGACCGTGTCGATCTTGGCTCAACTCTTTTG
GCCACTGACTGAGCGTGTCGATTGGCTCAACTGGGGCGCCTACGCGCCCTTGGCAGCAA
GGGGGCGTTT

Tetracycline-responsive miRNA Switches (Eylea CDS target)
Tetracycline Aptamer
siRNA #1
Complementary Strand

SLIM switch for Target 1 (SEQ ID NO:31)
GAACGCCTCCTAGAGGTGAAGAATACGACCACCTTGCGTGAGCGACCCATTGTTCAGG
TTTGTATTCTTTTGGCCACTGACTGAGAATACAAATGAACAATGGGGGCGCCTACGCAGG
CTCGAAAGAGCCTAAAACATAAGGGGGCGTTT

SLIM switch for Target 2 ((SEQ ID NO:32)
GAACGCCTCCTAGAGGTGAAGAATACGACCACCTTGCGTGAGCGACCCTGAGTTCCTTC
CCTAAATACTTTTGGCCACTGACTGAGTATTTAGGAGGAACTCAGGGGGGCGCCTACGCA
GGCTCGAAAGAGCCTAAAACATAAGGGGGCGTTT

SLIM switch for Target 3 (SEQ ID NO:33)
GAACGCCTCCTAGAGGTGAAGAATACGACCACCTTGCGTGAGCGACCAAGAGTTAACGT
GTCGATCTCTTTTGGCCACTGACTGAGAGATCGACGTTAACTCTTGGGGGCGCCTACGCA
GGCTCGAAAGAGCCTAAAACATAAGGGGGCGTTT

SLIM switch for Target 4 (SEQ ID NO:34)
GAACGCCTCCTAGAGGTGAAGAATACGACCACCTTGCGTGAGCGACCCTTCCCTAAATA
GTATAGATCTTTTGGCCACTGACTGAGATCTATACTTTAGGGAAGGGGGCGCCTACGCA
GGCTCGAAAGAGCCTAAAACATAAGGGGGCGTTT

SLIM switch for Target 5 (SEQ ID NO:35)
GAACGCCTCCTAGAGGTGAAGAATACGACCACCTTGCGTGAGCGACCGTGTCGATCTTG
GCTCAACTCTTTTGGCCACTGACTGAGCGTGTCGATTGGCTCAACTGGGGCGCCTACGCA
GGCTCGAAAGAGCCTAAAACATAAGGGGGCGTTT Eylea Target 1: TATTTAGGGAAGGAACTCAGG (SEQ ID NO:70)
Eylea Target 2: AATACAAACCTGAACAATGGG (SEQ ID NO:71)
Eylea Target 3: AGTTGAGCCAAGATCGACACG (SEQ ID NO:72)
Eylea Target 4: ATCTATACTATTTAGGGAAGG (SEQ ID NO:73)
Eylea Target 5: AGATCGACACGTTAACTCTTG (SEQ ID NO:74)

FIG. 18 (continued)

<u>Soluble fms-like tyrosine kinase 1 (sFLT1) VEGF inhibitor cDNA</u> (SEQ ID NO:36)

XATGGTCAGCTACTGGGACACCGGGGTCCTGCTGTGCGCGCTGCTCAGCTGTCTGCTTC
TCACAGGATCTAGTTCAGGTTCAAAATTAAAAGATCCTGAACTGAGTTTAAAAGGCACCC
AGCACATCATGCAAGCAGGCCAGACACTGCATCTCCAATGCAGGGGGGAAGCAGCCCA
TAAATGGTCTTTGCCTGAAATGGTGAGTAAGGAAAGCGAAAGGCTGAGCATAACTAAAT
CTGCCTGTGGAAGAAATGGCAAACAATTCTGCAGTACTTTAACCTTGAACACAGCTCAAG
CAAACCACACTGGCTTCTACAGCTGCAAATATCTAGCTGTACCTACTTCAAAGAAGAAGG
AAACAGAATCTGCAATCTATATATTTATTAGTGATACAGGTAGACCTTTCGTAGAGATGTA
CAGTGAAATCCCCGAAATTATACACATGACTGAAGGAAGGGAGCTCGTCATTCCCTGCC
GGGTTACGTCACCTAACATCACTGTTACTTTAAAAAAGTTTCCACTTGACACTTTGATCCC
TGATGGAAAACGCATAATCTGGGACAGTAGAAAGGGCTTCATCATATCAAATGCAACGT
ACAAAGAAATAGGGCTTCTGACCTGTGAAGCAACAGTCAATGGGCATTTGTATAAGACA
AACTATCTCACACATCGACAAACCAATACAATCATAGATGTCCAAATAAGCACACCACGC
CCAGTCAAATTACTTAGAGGCCATACTCTTGTCCTCAATTGTACTGCTACCACTCCCTTGA
ACACGAGAGTTCAAATGACCTGGAGTTACCCTGATGAAAAAAATAAGAGAGCTTCCGTA
AGGCGACGAATTGACCAAAGCAATTCCCATGCCAACATATTCTACAGTGTTCTTACTATT
GACAAAATGCAGAACAAAGACAAAGGACTTTATACTTGTCGTGTAAGGAGTGGACCATC
ATTCAAATCTGTTAACACCTCAGTGCATATATATGATAAAGCATTCATCACTGTGAAACAT
CGAAAACAGCAGGTGCTTGAAACCGTAGCTGGCAAGCGGTCTTACCGGCTCTCTATGAA
AGTGAAGGCATTTCCTCGCCGGAAGTTGTATGGTTAAAAGATGGGTTACCTGCGACTG
AGAAATCTGCTCGCTATTTGACTCGTGGCTACTCGTTAATTATCAAGGACGTAACTGAAG
AGGATGCAGGGAATTATACAATCTTGCTGAGCATAAAACAGTCAAATGTGTTTAAAAACC
TCACTGCCACTCTAATTGTCAATGTGAAACCCCAGATTTACGAAAAGGCCGTGTCATCGT
TTCCAGACCCGGCTCTCTACCCACTGGGCAGCAGACAAATCCTGACTTGTACCGCATAT
GGTATCCCTCAACCTACAATCAAGTGGTTCTGGCACCCCTGTAACCATAATCATTCCGAA
GCAAGGTGTGACTTTTGTTCCAATAATGAAGAGTCCTTTATCCTGGATGCTGACAGCAAC
ATGGGAAACAGAATTGAGAGCATCACTCAGCGCATGGCAATAATAGAAGGAAAGAATAA
GATGGCTAGCACCTTGGTTGTGGCTGACTCTAGAATTTCTGGAATCTACATTTGCATAGC
TTCCAATAAAGTTGGGACTGTGGGAAGAAACATAAGCTTTTATATCACAGATGTGCCAAA
TGGGTTTCATGTTAACTTGGAAAAAATGCCGACGGAAGGAGAGGACCTGAAACTGTCTT
GCACAGTTAACAAGTTCTTATACAGAGACGTTACTTGGATTTTACTGCGGACAGTTAATA
ACAGAACAATGCACTACAGTATTAGCAAGCAAAAAATGGCCATCACTAAGGAGCACTCC
ATCACTCTTAATCTTACCATCATGAATGTTTCCCTGCAAGATTCAGGCACCTATGCCTGCA
GAGCCAGGAATGTATACACAGGGGAAGAAATCCTCCAGAAGAAAGAAATTACAATCAGA
GGTGAGCACTGCAACAAAAAGGCTGTTTTCTCTCGGATCTCCAAATTTAAAAGCACAAGG
AATGATTGTACCACACAAGTAATGTAAAACATTAAAAACAAACAAAX

X = positions for SLIM regulatory elements (see below)

FIG. 19

SLIM SEQUENCES
6S-Folinic Acid-responsive miRNA Switches (sFLT1 CDS target)
6S-Folinic Acid Aptamer
siRNA #1
Complementary Strand

SLIM riboswitch for sFLT1 Target 1 (SEQ ID NO:37)
GAACGCCTCCTAACGTCTGGTCACGACCCTGCGTGAGCGACCAGACGAAGAGTGTCCTAGATCTTTTGGCCACTGACTGAGATCTAGGACTCTTCGTCTGGGGGCGCCTACGCAGCCCCTCGAAATCACGAGGGAGACGAGATAAGGGGGCGTTT

SLIM riboswitch for sFLT1 Target 2 (SEQ ID NO:38)

GAACGCCTCCTAACGTCTGGTCACGACCCTGCGTGAGCGACCGCTTTCCGACTCGTATTGATCTTTTGGCCACTGACTGAGATCAATACGTCGGAAAGCGGGGGCGCCTACGCAGCCCCTCGAAATCACGAGGGAGACGAGATAAGGGGGCGTTT

SLIM riboswitch for sFLT1 Target 3 (SEQ ID NO:39)

GAACGCCTCCTAACGTCTGGTCACGACCCTGCGTGAGCGACCACCTTCTTTACCGTTTGTTACTTTTGGCCACTGACTGAGTAACAAACTAAAGAAGGTGGGGGCGCCTACGCAGCCCCTCGAAATCACGAGGGAGACGAGATAAGGGGGCGTTT

SLIM riboswitch for sFLT1 Target 4 (SEQ ID NO:40)

GAACGCCTCCTAACGTCTGGTCACGACCCTGCGTGAGCGACCCGTTTGTTAAGACGTCATGACTTTTGGCCACTGACTGAGTCATGACGTTAACAAACGGGGGGCGCCTACGCAGCCCCTCGAAATCACGAGGGAGACGAGATAAGGGGGCGTTT

SLIM riboswitch for sFLT1 Target 5 (SEQ ID NO:41)

GAACGCCTCCTAACGTCTGGTCACGACCCTGCGTGAGCGACGCAAATATCTAGCTGTACCTACTTTTGGCCACTGACTGAGTAGGTACATAGATATTTGCGGGGCGCCTACGCAGCCCCTCGAAATCACGAGGGAGACGAGATAAGGGGGCGTTT

Theophylline-responsive miRNA Switches (sFLT1 CDS target)

Theophylline Aptamer
siRNA #1
Complementary Strand

SLIM riboswitch for sFLT1 Target 1 (SEQ ID NO:42)

GAACGCCTCCTTGATACCAGCTGCGTGAGCGACCAGACGAAGAGTGTCCTAGATCTTTTGGCCACTGACTGAGATCTAGGACTCTTCGTCTGGGGGCGCCTACGCGCCCTTGGCAGCAAGGGGGCGTTT

SLIM riboswitch for sFLT1 Target 2 (SEQ ID NO:43)

GAACGCCTCCTTGATACCAGCTGCGTGAGCGACCGCTTTCCGACTCGTATTGATCTTTTGGCCACTGACTGAGATCAATACGTCGGAAAGCGGGGGCGCCTACGCGCCCTTGGCAGCAAGGGGGCGTTT

FIG. 19 (continued)

SLIM riboswitch for sFLT1 Target 3 (SEQ ID NO:44)
GAACGCCTCCTTGATACCAGCTGCGTGAGCGACCACCTTCTTTACCGTTTGTTACTTTTGG
CCACTGACTGAGTAACAAACTAAAGAAGGTGGGGCGCCTACGCGCCCTTGGCAGCAAG
GGGGCGTTT

SLIM riboswitch for sFLT1 Target 4 (SEQ ID NO:45)
GAACGCCTCCTTGATACCAGCTGCGTGAGCGACCCGTTTGTTAAGACGTCATGACTTTTG
GCCACTGACTGAGTCATGACGTTAACAAACGGGGGGCGCCTACGCGCCCTTGGCAGCAA
GGGGGCGTTT

SLIM riboswitch for sFLT1 Target 5 (SEQ ID NO:46)
GAACGCCTCCTTGATACCAGCTGCGTGAGCGACGCAAATATCTAGCTGTACCTACTTTTG
GCCACTGACTGAGTAGGTACATAGATATTTGCGGGGCGCCTACGCGCCCTTGGCAGCAA
GGGGGCGTTT

Tetracycline-responsive miRNA Switches (sFLT1 CDS target)

Tetracycline Aptamer
siRNA #1
Complementary Strand

SLIM riboswitch for sFLT1 Target 1 (SEQ ID NO:47)
GAACGCCTCCTAGAGGTGAAGAATACGACCACCTTGCGTGAGCGACCAGACGAAGAGTG
TCCTAGATCTTTTGGCCACTGACTGAGATCTAGGACTCTTCGTCTGGGGGCGCCTACGCA
GGCTCGAAAGAGCCTAAAACATAAGGGGGCGTTT

SLIM riboswitch for sFLT1 Target 2 (SEQ ID NO:48)
GAACGCCTCCTAGAGGTGAAGAATACGACCACCTTGCGTGAGCGACCGCTTTCCGACTC
GTATTGATCTTTTGGCCACTGACTGAGATCAATACGTCGGAAAGCGGGGGCGCCTACGC
AGGCTCGAAAGAGCCTAAAACATAAGGGGGCGTTT

SLIM riboswitch for sFLT1 Target 3 (SEQ ID NO:49)
GAACGCCTCCTAGAGGTGAAGAATACGACCACCTTGCGTGAGCGACCACCTTCTTTACC
GTTTGTTACTTTTGGCCACTGACTGAGTAACAAACTAAAGAAGGTGGGGGCGCCTACGCA
GGCTCGAAAGAGCCTAAAACATAAGGGGGCGTTT

SLIM riboswitch for sFLT1 Target 4 (SEQ ID NO:50)
GAACGCCTCCTAGAGGTGAAGAATACGACCACCTTGCGTGAGCGACCCGTTTGTTAAGA
CGTCATGACTTTTGGCCACTGACTGAGTCATGACGTTAACAAACGGGGGGCGCCTACGC
AGGCTCGAAAGAGCCTAAAACATAAGGGGGCGTTT

SLIM riboswitch for sFLT1 Target 5 (SEQ ID NO:51)
GAACGCCTCCTAGAGGTGAAGAATACGACCACCTTGCGTGAGCGACGCAAATATCTAGC
TGTACCTACTTTTGGCCACTGACTGAGTAGGTACATAGATATTTGCGGGGCGCCTACGCA
GGCTCGAAAGAGCCTAAAACATA sFLT1 Target 1: TAGGTACAGCTAGATATTTGC (SEQ ID NO:75)
sFLT1 Target 2: TCATGACGTCTTAACAAACGG (SEQ ID NO:76)
sFLT1 Target 3: TAACAAACGGTAAAGAAGGTG (SEQ ID NO:77)
sFLT1 Target 4: ATCAATACGAGTCGGAAAGCG (SEQ ID NO:78)
sFLT1 Target 5: ATCTAGGACACTCTTCGTCTG (SEQ ID NO: 79)

FIG. 23

SEQUENCES

Codon Optimized PTGS2 (SEQ ID NO:52)

ATGCTTGCCCGGGCCCTGCTTCTGTGTGCGGTATTGGCACTGAGTCACACAGCCAACCCG
TGCTGCTCACACCCATGTCAGAATCGGGGAGTTTGCATGTCAGTAGGGTTTGACCAATATA
AGTGCGACTGTACCCGGACAGGCTTTTATGGAGAAAATTGTTCTACACCCGAATTTTTGAC
GAGGATTAAGCTCTTTCTGAAGCCTACACCAAATACAGTCCATTATATCCTCACGCACTTCA
AGGGTTTTTGGAATGTCGTAAACAACATTCCGTTTCTGAGAAATGCGATAATGTCTTACGTC
CTTACATCCCGGAGCCACCTTATTGACTCACCCCAACATACAACGCCGACTACGGATACA
AAAGTTGGGAAGCTTTCTCCAACCTGTCTTACTACACGCGAGCATTGCCTCCTGTACCCGA
CGATTGCCCGACGCCGTTGGGGGTGAAAGGAAAAAAGCAGCTCCCGGACTCAAACGAAAT
AGTAGAGAAATTGTTGCTTCGCCGAAAATTTATACCAGACCCGCAGGGTAGCAATATGATG
TTTGCGTTCTTCGCTCAGCACTTCACTCACCAATTCTTTAAGACAGACCACAAGAGAGGTC
CCGCATTCACGAATGGCCTTGGACACGGCGTCGACTTGAACCACATATATGGGGAGACAT
TGGCCAGACAAAGGAAACTTCGATTGTTTAAGGATGGGAAAATGAAATACCAAATTATTGAT
GGCGAGATGTATCCTCCAACAGTGAAGGATACGCAAGCGGAGATGATTTATCCACCGCAG
GTACCAGAGCATTTGCGGTTCGCGGTGGGGCAGGAAGTATTTGGACTTGTTCCCGGTCTG
ATGATGTACGCCACAATATGGCTCCGGGAGCATAATCGCGTGTGTGACGTACTTAAGCAAG
AGCACCCGGAATGGGGCGACGAGCAACTTTTTCAAACGAGTCGACTGATTCTCATTGGGG
AAACGATTAAAATAGTGATCGAAGATTATGTGCAACATCTTTCTGGTTACCACTTTAAGTTG
AAGTTCGATCCTGAGCTGCTTTTCAATAAACAATTCCAGTATCAAAACAGAATCGCCGCGG
AGTTCAACACGCTGTATCATTGGCATCCCCTGTTGCCCGATACTTTTCAAATCCATGACCAG
AAATACAATTACCAGCAATTTATATATAATAACTCTATCCTCCTGGAGCATGGCATTACACAA
TTCGTTGAAAGTTTCACAAGGCAGATCGCAGGAAGAGTTGCGGGTGGCCGGAATGTGCCG
CCTGCCGTGCAAAAGGTATCACAGGCTAGCATCGACCAATCAAGGCAAATGAAGTACCAG
TCTTTTAATGAGTACAGGAAAAGGTTCATGCTGAAGCCTTACGAGAGCTTTGAAGAACTGA
CGGGCGAAAAGGAAATGTCCGCGGAACTGGAAGCGTTGTACGGAGATATTGATGCGGTAG
AGCTCTACCCCGCGCTTCTGGTCGAAAAGCCCCGGCCAGATGCCATTTTCGGGGAAACCA
TGGTTGAAGTGGGCGCCCCATTCAGTTTGAAAGGTCTGATGGGTAATGTAATTTGCAGTCC
GGCGTACTGGAAGCCTTCCACTTTTGGTGGGGAAGTGGGGTTTCAAATTATCAATACGGCC
TCAATTCAGTCTCTGATTTGTAACAATGTTAAGGGATGTCCCTTTACATCTTTTAGTGTACCG
GACCCCGAGCTTATTAAGACCGTGACCATAAATGCTTCAAGCTCTAGAAGTGGTCTTGATG
ATATCAACCCCACAGTTTTGCTTAAGGAAAGGAGCACGGAGCTCTAA

FIG. 23 (continued)

Codon Optimized PTGFR (SEQ ID NO:53)

ATGAGCATGAACAACTCAAAACAGTTGGTCTCCCCAGCAGCGGCCCTTTTGTCCAACACAA
CGTGTCAGACTGAGAATAGACTCAGTGTATTTTTTAGCGTGATTTTATGACCGTCGGTATC
CTGTCTAACTCTCTTGCCATAGCAATATTGATGAAAGCCTATCAGCGATTCCGGCAAAAGTC
TAAGGCGTCATTTTTGTTGTTGGCAAGCGGGCTTGTCATCACGGACTTTTCGGGCACCTC
ATTAACGGAGCCATAGCCGTGTTCGTTTATGCTTCAGACAAAGAGTGGATACGATTCGATC
AGAGCAATGTGCTTTGCAGTATCTTTGGCATATGTATGGTGTTAGTGGATTGTGTCCACTC
TTGCTTGGGAGCGTGATGGCTATTGAAAGATGCATCGGGGTGACTAAACCTATCTTTCACA
GTACCAAAATTACATCTAAGCACGTCAAGATGATGTTGTCCGGGGTGTGTCTTTTGCTGTC
TTTATTGCGTTGTTGCCAATACTGGGCCACAGGGACTACAAAATTCAGGCCTCACGCACTT
GGTGCTTCTATAACACTGAGGATATTAAAGACTGGGAGGATAGGTTTATCTTCTTCTTTTC
TCATTCCTCGGTCTGCTCGCACTGGGGGTATCCCTTTGTGTAACGCTATCACAGGTATCA
CCTTGTTGCGCGTTAAATTTAAGAGCCAACAGCATCGCCAGGGGAGGTCACATCACCTCG
AAATGGTAATACAGTTGCTCGCGATCATGTGTGTTAGTTGTATCTGCTGGTCACCCTTCTTG
GGATATAGAATAATTCTGAATGGAAAAGAAAGTACAAAGTCTATGAAGAACAGAGCGATTT
TCTGCATCGATTGCAATGGCCCACTTTGGAATAA

PTGS2-P2A-PTGFR (SEQ ID NO:54)

PTGS2: Bold (SEQ ID NO:55)

*P2A: Italicized* (SEQ ID NO:56)

PTGFR: Underlined (SEQ ID NO:57)

**XATGCTTGCCCGGGCCCTGCTTCTGTGTGCGGTATTGGCACTGAGTCACACAGCCAACC
CGTGCTGCTCACACCCATGTCAGAATCGGGGAGTTTGCATGTCAGTAGGGTTTGACCAAT
ATAAGTGCGACTGTACCCGGACAGGCTTTTATGGAGAAAATTGTTCTACACCCGAATTTT
TGACGAGGATTAAGCTCTTTCTGAAGCCTACACCAAATACAGTCCATTATATCCTCACGC
ACTTCAAGGGTTTTTGGAATGTCGTAAACAACATTCCGTTTCTGAGAAATGCGATAATGT
CTTACGTCCTTACATCCCGGAGCCACCTTATTGACTCACCCCCAACATACAACGCCGACT
ACGGATACAAAAGTTGGGAAGCTTTCTCCAACCTGTCTTACTACACGCGAGCATTGCCTC
CTGTACCCGACGATTGCCCGACGCCGTTGGGGGTGAAAGGAAAAAAGCAGCTCCCGGA
CTCAAACGAAATAGTAGAGAAATTGTTGCTTCGCCGAAAATTTATACCAGACCCGCAGG
GTAGCAATATGATGTTTGCGTTCTTCGCTCAGCACTTCACTCACCAATTCTTTAAGACAGA
CCACAAGAGAGGTCCCGCATTCACGAATGGCCTTGGACACGGCGTCGACTTGAACCACA
TATATGGGGAGACATTGGCCAGACAAAGGAAACTTCGATTGTTAAGGATGGGAAAATG
AAATACCAAATTATTGATGGCGAGATGTATCCTCCAACAGTGAAGGATACGCAAGCGGA
GATGATTTATCCACCGCAGGTACCAGAGCATTTGCGGTTCGCGGTGGGGCAGGAAGTAT
TTGGACTTGTTCCCGGTCTGATGATGTACGCCACAATGGCTCCGGGAGCATAATCGCG
TGTGTGACGTACTTAAGCAAGAGCACCCGGAATGGGGCGACGAGCAACTTTTCAAACG
AGTCGACTGATTCTCATTGGGGAAACGATTAAAATAGTGATCGAAGATTATGTGCAACAT
CTTTCTGGTTACCACTTTAAGTTGAAGTTCGATCCTGAGCTGCTTTTCAATAAACAATTCC
AGTATCAAAACAGAATCGCCGCGGAGTTCAACACGCTGTATCATTGGCATCCCCTGTTGC
CCGATACTTTTCAAATCCATGACCAGAAATACAATTACCAGCAATTTATATATAATAACTC**

FIG. 23 (continued)

TATCCTCCTGGAGCATGGCATTACACAATTCGTTGAAAGTTTCACAAGGCAGATCGCAGG
AAGAGTTGCGGGTGGCCGGAATGTGCCGCCTGCCGTGCAAAAGGTATCACAGGCTAGC
ATCGACCAATCAAGGCAAATGAAGTACCAGTCTTTTAATGAGTACAGGAAAAGGTTCATG
CTGAAGCCTTACGAGAGCTTTGAAGAACTGACGGGCGAAAAGGAAATGTCCGCGGAACT
GGAAGCGTTGTACGGAGATATTGATGCGGTAGAGCTCTACCCCGCGCTTCTGGTCGAAA
AGCCCCGGCCAGATGCCATTTTCGGGGAAACCATGGTTGAAGTGGGCGCCCCATTCAGT
TTGAAAGGTCTGATGGGTAATGTAATTTGCAGTCCGGCGTACTGGAAGCCTTCCACTTTT
GGTGGGGAAGTGGGGTTTCAAATTATCAATACGGCCTCAATTCAGTCTCTGATTTGTAAC
AATGTTAAGGGATGTCCCTTTACATCTTTTAGTGTACCGGACCCCGAGCTTATTAAGACC
GTGACCATAAATGCTTCAAGCTCTAGAAGTGGTCTTGATGATATCAACCCCACAGTTTTG
CTTAAGGAAAGGAGCACGGAGCTC*GGAAGCGGAGCTACTAACTTCAGCCTGCTGAAGCA*
*GGCTGGAGACGTCGAGGAGAACCCTGGACCT*AGCATGAACAACTCAAAACAGTTGGTCTC
CCCAGCAGCGGCCCTTTTGTCCAACACAACGTGTCAGACTGAGAATAGACTCAGTGTATTT
TTTAGCGTGATTTTTATGACCGTCGGTATCCTGTCTAACTCTCTTGCCATAGCAATATTGAT
GAAAGCCTATCAGCGATTCCGGCAAAAGTCTAAGGCGTCATTTTTGTTGTTGGCAAGCGGG
CTTGTCATCACGGACTTTTCGGGCACCTCATTAACGGAGCCATAGCCGTGTTCGTTTATG
CTTCAGACAAAGAGTGGATACGATTCGATCAGAGCAATGTGCTTTGCAGTATCTTTGGCAT
ATGTATGGTGTTTAGTGGATTGTGTCCACTCTTGCTTGGGAGCGTGATGGCTATTGAAAGA
TGCATCGGGGTGACTAAACCTATCTTTCACAGTACCAAAATTACATCTAAGCACGTCAAGAT
GATGTTGTCCGGGGTGTGTCTTTTGCTGTCTTTATTGCGTTGTTGCCAATACTGGGCCAC
AGGGACTACAAAATTCAGGCCTCACGCACTTGGTGCTTCTATAACACTGAGGATATTAAAG
ACTGGGAGGATAGGTTTTATCTTCTTCTTTTCTCATTCCTCGGTCTGCTCGCACTGGGGGT
ATCCCTTTTGTGTAACGCTATCACAGGTATCACCTTGTTGCGCGTTAAATTTAAGAGCCAAC
AGCATCGCCAGGGGAGGTCACATCACCTCGAAATGGTAATACAGTTGCTCGCGATCATGT
GTGTTAGTTGTATCTGCTGGTCACCCTTCTTGGGATATAGAATAATTCTGAATGGAAAAGAA
AAGTACAAAGTCTATGAAGAACAGAGCGATTTTCTGCATCGATTGCAATGGCCCACTTTGG
AATAA☒

X- locations for the SLIM riboswitches or target sequences

Complete AAV expression cassette for PGF2alpha biosynthesis(SEQ ID NO:58)

*TC40: Underlined and Italicized* (SEQ ID NO:59)

PTGS2: Bold (SEQ ID NO:60)

*P2A: Italicized* (SEQ ID NO:61)

PTGFR: Underlined (SEQ ID NO:62)

*TC45: Bold and Italicized* (SEQ ID NO:63)

GGTTGGCCACTCCCTCTCTGCGCGCTCGCTCGCTCACTGAGGCCGGGCGACCAAGGTC
GCCCGACGCCCGGGCTTTGCCCGGGCGGCCTCAGTGAGCGAGCGAGCGCGCAGAGAGG
GAGTGGCCAACTCCATCACTAGGGGTTCCTAGATCTGAATTCGGTACCCCTAGTTATTAAT
AGTAATCAATTACGGGGTCATTAGTTCATAGCCCATATATGGAGTTCCGCGTTACATAACTT
ACGGTAAATGGCCCGCCTGGCTGACCGCCCAACGACCCCGCCCATTGACGTCAATAATG
ACGTATGTTCCCATAGTAACGCCAATAGGGACTTTCCATTGACGTCAATGGGTGGACTATT
TACGGTAAACTGCCCACTTGGCAGTACATCAAGTGTATCATATGCCAAGTACGCCCCCTAT

FIG. 23 (continued)

```
TGACGTCAATGACGGTAAATGGCCCGCCTGGCATTATGCCCAGTACATGACCTTATGGGACTTTCCT
ACTTGGCAGTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTAATTATTTTGTGC
AGCGATGGGGGCGGGGGGGGGGGGGGGCGCGCGCCAGGCGGGGCGGGGCGGGGCGAGGGG
CGGGGCGGGGCGAGGCGGAGAGGTGCGGCGGCAGCCAATCAGAGCGGCGCGCTCCGAAAGTTTC
CTTTTATGGCGAGGCGGCGGCGGCGGCCCTATAAAAAGCGAAGCGCGCGGCGGGCGGGAGT
CGCTGCGACGCTGCCTTCGCCCCGTGCCCCGCTCCGCCGCCGCCTCGCGCCGCCCGCCCCGGCT
CTGACTGACCGCGTTACTCCCACAGGTGAGCGGGCGGGACGGCCCTTCTCCTCCGGGCTGTAATTA
GCGCTTGGTTTAATGACGGCTTGTTTCTTTTCTGTGGCTGCGTGAAAGCCTTGAGGGGCTCCGGGA
GCTAGAGCCTCTGCTAACCATGTTCATGCCTTCTTCTTTTTCCTACAGCTCCTGGGCAACGTGCTGGT
TATTGTGCTGTCTCATCATTTTGGCAAAGAATTCCTCGAAGATCTAGGCAACTCGAGAAACAAACAAA
CTGAGGTGCAGGTACATCCAGCTGACGAGTCCCAAATAGGACGAAAGGGAGAGGTGAAGAATACGA
CCACCTAGGCTCGAAAGAGCCTAAAACATACCTTCCTGGATTCCACTGCTATCCACAAAAAGAAAAAT
AAAAAGCCACCATGCTTGCCCGGGCCCTGCTTCTGTGTGCGGTATTGGCACTGAGTCACACAGCCA
ACCCGTGCTGCTCACACCCATGTCAGAATCGGGGAGTTTGCATGTCAGTAGGGTTTGACCAATATA
AGTGCGACTGTACCCGGACAGGCTTTTATGGAGAAAATTGTTCTACACCCGAATTTTTGACGAGGA
TTAAGCTCTTTCTGAAGCCTACACCAAATACAGTCCATTATATCCTCACGCACTTCAAGGGTTTTTG
GAATGTCGTAAACAACATTCCGTTTCTGAGAAATGCGATAATGTCTTACGTCCTTACATCCCGGAG
CCACCTTATTGACTCACCCCCAACATACAACGCCGACTACGGATACAAAAGTTGGGAAGCTTTCTC
CAACCTGTCTTACTACACGCGAGCATTGCCTCCTGTACCCGACGATTGCCCGACGCCGTTGGGGG
TGAAAGGAAAAAAGCAGCTCCCGGACTCAAACGAAATAGTAGAGAAATTGTTGCTTCGCCGAAAA
TTTATACCAGACCCGCAGGGTAGCAATATGATGTTTGCGTTCTTCGCTCAGCACTTCACTCACCAA
TTCTTTAAGACAGACCACAAGAGAGGTCCCGCATTCACGAATGGCCTTGGACACGGCGTCGACTT
GAACCACATATATGGGGAGACATTGGCCAGACAAAGGAAACTTCGATTGTTTAAGGATGGGAAAA
TGAAATACCAAATTATTGATGGCGAGATGTATCCTCCAACAGTGAAGGATACGCAAGCGGAGATG
ATTTATCCACCGCAGGTACCAGAGCATTTGCGGTTCGCGGTGGGCAGGAAGTATTTGGACTTGTT
CCCGGTCTGATGATGTACGCCACAATATGGCTCCGGGAGCATAATCGCGTGTGTGACGTACTTAA
GCAAGAGCACCCGGAATGGGGCGACGAGCAACTTTTTCAAACGAGTCGACTGATTCTCATTGGGG
AAACGATTAAAATAGTGATCGAAGATTATGTGCAACATCTTTCTGGTTACCACTTTAAGTTGAAGTT
CGATCCTGAGCTGCTTTTCAATAAACAATTCCAGTATCAAAACAGAATCGCCGCGGAGTTCAACAC
GCTGTATCATTGGCATCCCCTGTTGCCCGATACTTTTCAAATCCATGACCAGAAATACAATTACCA
GCAATTTATATATAATAACTCTATCCTCCTGGAGCATGGCATTACACAATTCGTTGAAAGTTTCACA
AGGCAGATCGCAGGAAGAGTTGCGGGTGGCCGGAATGTGCCGCCTGCCGTGCAAAAGGTATCAC
AGGCTAGCATCGACCAATCAAGGCAAATGAAGTACCAGTCTTTTAATGAGTACAGGAAAAGGTTC
ATGCTGAAGCCTTACGAGAGCTTTGAAGAACTGACGGGCGAAAAGGAAATGTCCGCGGAACTGG
AAGCGTTGTACGGAGATATTGATGCGGTAGAGCTCTACCCCGCGCTTCTGGTCGAAAAGCCCCGG
CCAGATGCCATTTTCGGGGAAACCATGGTTGAAGTGGGCGCCCCATTCAGTTTGAAAGGTCTGAT
GGGTAATGTAATTTGCAGTCCGGCGTACTGGAAGCCTTCCACTTTTGGTGGGGAAGTGGGGTTTCA
AATTATCAATACGGCCTCAATTCAGTCTCTGATTTGTAACAATGTTAAGGGATGTCCCTTTACATCT
TTTAGTGTACCGGACCCCGAGCTTATTAAGACCGTGACCATAAATGCTTCAAGCTCTAGAAGTGGT
CTTGATGATATCAACCCCACAGTTTTGCTTAAGGAAAGGAGCACGGAGCTCGGAAGCGGAGCTAC
TAACTTCAGCCTGCTGAAGCAGGCTGGAGACGTCGAGGAGAACCCTGGACCTAGCATGAACAACTC
AAAACAGTTGGTCTCCCCAGCAGCGGCCCTTTTGTCCAACACAACGTGTCAGACTGAGAATAGACTC
AGTGTATTTTTTAGCGTGATTTTATGACCGTCGGTATCCTGTCTAACTCTCTTGCCATAGCAATATTG
ATGAAAGCCTATCAGCGATTCCGGCAAAGTCTAAGGCGTCATTTTTGTTGTTGGCAAGCGGGCTTG
TCATCACGGACTTTTTCGGGCACCTCATTAACGGAGCCATAGCCGTGTTCGTTTATGCTTCAGACAAA
GAGTGGATACGATTCGATCAGAGCAATGTGCTTTGCAGTATCTTTGGCATATGTATGGTGTTTAGTGG
ATTGTGTCCACTCTTGCTTGGGAGCGTGATGGCTATTGAAAGATGCATCGGGGTGACTAAACCTATC
TTTCACAGTACCAAAATTACATCTAAGCACGTCAAGATGATGTTGTCCGGGGTGTGTCTTTTTGCTGT
CTTTATTGCGTTGTTGCCAATACTGGGCCACAGGGACTACAAAATTCAGGCCTCACGCACTTG
```

FIG. 23 (continued)

GTGCTTCTATAACACTGAGGATATTAAAGACTGGGAGGATAGGTTTTATCTTCTTCTTTTCTCATTCCT
CGGTCTGCTCGCACTGGGGGTATCCCTTTTGTGTAACGCTATCACAGGTATCACCTTGTTGCGCGTT
AAATTTAAGAGCCAACAGCATCGCCAGGGGAGGTCACATCACCTCGAAATGGTAATACAGTTGCTCG
CGATCATGTGTGTTAGTTGTATCTGCTGGTCACCCTTCTTGGGATATAGAATAATTCTGAATGGAAAA
GAAAAGTACAAAGTCTATGAAGAACAGAGCGATTTTCTGCATCGATTGCAATGGCCCACTTTGGAATA
AAAACAAACAAA*CTGAGATGCAGGTACATCCCACTGATGAGTCCCAAATAGGACGAAAGGGAGAG*
*GTGAAGAATACGACCACCTAGGCTCGAAAGAGCCTAAAACATACCTTCTGGGATTCCACTGCTAT*
*CCAC*AAAAAGAAAAATAAAAAGCGGCCGCTGCAGGAGTCGGTCGACTAGAGCTCGCTGATCAGCCT
CGACTGTGCCTTCTAGTTGCCAGCCATCTGTTGTTTGCCCCTCCCCGTGCCTTCCTTGACCCTGGA
AGGTGCCACTCCCACTGTCCTTTCCTAATAAAATGAGGAAATTGCATCGCATTGTCTGAGTAGGTGTC
ATTCTATTCTGGGGGGTGGGGTGGGCAGGACAGCAAGGGGGAGGATTGGGAAGACAATAGCAGG
CATGCTGGGGAGAGATCTAGGAACCCCTAGTGATGGAGTTGGCCACTCCCTCTCTGCGCGCTCGCT
CGCTCACTGAGGCCGCCCGGGCAAAGCCCGGGCGTCGGGCGACCTTTGGTCGCCCGGCCTCAGT
GAGCGAGCGAGCGCGCAGAGAGGGAGTGGCCAACC

ADDITIONAL RIBOSWITCH SEQUENCES TO TC40 AND TC45

<u>L2bulge9 (Theophylline OFF switch)</u> (SEQ ID NO:64)

CTCGAGGCGATCGCAAACAAACAAAGCTGTCACCGGATGTGCTTTCCGGTCTGATGAGTCCGTTGTC
CAATACCAGCATCGTCTTGATGCCCTTGGCAGTGGATGGGGACGGAGGACGAAACAGCAAAAAGAA
AAATAAAAATTTTTTTTTTAATTAATCTTGGGCCC

<u>Theo6HDV (Theophylline OFF switch)</u> (SEQ ID NO:65)

ATGGCCGGCATGGTCCCAGCCTCCTCGCTGGCGCCGGCTGGGCAACCACATACCAGCCGAAAGGC
CCTTGGCAGGTGGGCGAATGGGACGCACAAATCTCTCTAGCTTCCCAGAGAGAAGCGAGAGAAAAG
TGGCTCTC

<u>GuaM8HDV (Guanine OFF switch)</u> (SEQ ID NO:66)

ATGGCCGGCATGGTCCCAGCCTCCTCGCTGGCGCCGGCTGGGCAATGCTATAATCGCGTGGATATG
GCACGCAAGTTTCTACCGGGCACCGTAAATGTCCGACTAGTAGCGAATGGGACGCACAAATCTCTCT
AG

<u>K19 (Tetracycline ON switch)</u> ((SEQ ID NO:67)

CAAACAAACAAAGGCGCGTCCTGGATTCGTGGTAAAACATACCAGATTTCGATCTGGAGAGGTGAAG
AATACGACCACCTGTAGTATCCAGCTGATGAGTCCCAAATAGGACGAAACGCGCTAAACAAACAAAC

RIBOSWITCH MODULATED GENE THERAPY FOR RETINAL DISEASES

CROSS-REFERENCE TO RELATED APPLICATIONS

This Application represents the national stage entry of PCT International Application No. PCT/US2018/021719 filed on Mar. 9, 2018 and claims priority to U.S. Provisional Application No. 62/469,705 filed on Mar. 10, 2017, the contents of which are incorporated by reference in its entirety.

STATEMENT REGARDING FEDERALLY SPONSORED RESEARCH

N/A

BACKGROUND OF THE INVENTION

Age-Related Macular Degeneration (AMD) and glaucoma are leading causes of vision loss worldwide. AMD is a common eye disease among people age 50 and older. In AMD, there is damage to the macula, a small area made up of millions of light-sensing cells near the center of the retina and the part of the eye needed for sharp, central vision, and the ability to see objects that are straight ahead. Macular damage is caused by the formation of deposits called drusen, and in some cases, the growth of abnormal blood vessels, under the retina.

Glaucoma is a group of diseases in which the eye's optic nerve is damaged resulting in vision loss and blindness. The hallmark of glaucoma is increased intraocular pressure related to build-up of fluid (aqueous humor). It some patients the disease is genetic. In other patients, inflammation in the eye is thought to be involved in glaucoma.

Neither AMD nor glaucoma can be prevented. There is no treatment for early AMD in which there is no symptoms or loss of vision. Advanced AMD is treated with biologics. Glaucoma is often treated with prostaglandin eye drops. Current treatments are invasive and expensive and burdensome on the patient and clinic, requiring monthly eye injections (AMD) or daily eye drop administration.

Ocular gene therapies have the potential to profoundly improve the quality of life in patients with inherited retinal disease. Several factors make the eye an ideal organ for gene-replacement therapy. The eye is accessible, it is a compartmentalized, privileged site. This in turn means that immunologically the eyes are able to tolerate the introduction of foreign proteins/antigens without eliciting an inflammatory immune response. Clinical trials can take advantage of contralateral controls. For this reason, gene therapies for eye diseases are in development.

In this regard, recombinant adeno-associated virus (rAAV) vectors have emerged as promising tools for mediating gene therapy for diseases of the retina. Effectively controlling gene expression levels following vector delivery is paramount to the success of potential gene therapies, where uncontrolled over-expression of the therapeutic transgenes can lead to toxicity. Traditionally, inducible promoter systems have been employed. Unfortunately, due to the limited coding capacity of AAV, and the large size of the regulatory elements required to make such systems work effectively, inclusion of traditional promoters is not feasible.

Riboswitches are a possible alternative. Riboswitches are specific regulatory components of an mRNA molecule that bind and target small target molecules thereby regulating the expression of the riboswitch-containing mRNA's protein product in a cis-fashion. Thus, an mRNA that contains a riboswitch is directly involved in regulating its own activity, in response to the concentrations of its target molecule. Some riboswitches are "self-targeting", which means that can regulate their own expression. The switch includes an RNA element that can adapt to one of two mutually exclusive secondary structures. One of these structures is a signal for gene expression to be "on" and the other conformation turns the gene "off."

However, often toxic concentrations of ligand are necessary to "flip the switch" to turn on or off gene expression. Consequently, a goal of current research is to improve these regulatory devices toward efficiency, improved regulatory parameters, and clinical applicability. The subject of this invention are riboswitches that can turn on or off gene expression in the retina for use in ocular gene therapy.

SUMMARY OF THE INVENTION

The present invention overcomes the aforementioned drawbacks by providing constructs, kits and methods of regulating a transgene expression using a modified riboswitch which works by a dual mechanism of gene silencing. The invention provides a distinct and improved design over prior riboswitches with its dual mechanism for gene silencing, thereby allowing for better control of expression of the transgene. Novel modified riboswitches are described in more detail herein, including a self-targeting ligand inactivating microRNA (SLIM) switch which is an ON-type switch that mediates an increase in gene expression in the presence of the ligand. Compositions and methods of using this technology to treat AMD are provided herein. Specifically, this SLIM switch can be used to intermittently switch on expression of transgene, for example, a VEGF inhibitor. Further embodiments of SLIM switches that can be used to treat glaucoma. Compositions and method of use of this technology are contemplated for the treatment of glaucoma, where it would be beneficial to intermittently turn off, or decrease expression of the prostaglandin in the eye of a patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B is a schematic showing the design and functioning of a SLIM switch with and without ligand.

FIG. 2C is a schematic representing the rAAV vector encoding Aflibercept (a VEGF inhibitor), with the modified switch (smiRNA) and target miRNA sequences (miRT).

FIG. 3 is a schematic of on-type aptamers that can be used in the design of SLIM switches.

FIG. 4 depicts the components of a Theo-SLIM construct.

FIG. 5 is a sequence of an exemplary construct containing Aflibercept (a VEGF inhibitor), Theo-SLIM and three miRNA target sites.

FIGS. 14A, 14B, 14C, 14D, 14E, 14F, 14G, 14H, 14I, 14J, 14K, and 14L are representative fluorescein angiography images of CNV lesions. Leakage from CNV lesions was assessed 7 days following laser injury. Representative FA images taken 5 minutes after fluorescein injection for mice injected with either (A-C) rAAV2[MAX].smCBA-Eylea, (D-F) rAAV2[MAX].smCBA-Eylea-1×-TC45+standard diet, (G-I) rAAV2[MAX].smCBA-Eylea-1×-TC45+tetracycline diet or PBS (n=16-20 lesions per group). Images of 3 mice per group with red arrows indicating site of the laser injury.

FIG. 16 are exemplary sequences of the recombinant VEGF inhibitor cDNA (SEQ ID NO:18), and complete AAV vector comprising SLIM Eylea (SEQ ID NO:19).

FIG. 18 are exemplary 6-S-Folinic Acid-responsive miRNA Switches (Eylea CDS target) (SEQ ID NOs:21-25), Theophylline-responsive miRNA switches (Eylea CDS target) (SEQ ID NOs:26-30), tetracycline-responsive miRNA switches (Eylea CDS target) (SEQ ID NO:31-35), and the soluble fms-like tyrosine kinase 1 (sFLT1) VEGF inhibitor cDNA (SEQ ID NO:36) that can be used with the SLIM switches to treat AMD.

FIG. 19 shows exemplary sequences for 6S-Folinic Acid-responsive miRNA SLIM Switches (sFLT1 CDS target) including SEQ ID NOs:37-41, theophylline-responsive miRNA SLIM switches (sFLT1-CDS target) including SEQ ID NOs:42-46, and tetracycline-responsive miRNA switches (sFLT1-CDS target) SEQ ID NOs:47-51.

FIG. 23 are exemplary sequences for use in the present invention, including a codon optimized PTGS2 sequence (SEQ ID NO:52), a codon optimized PTGFR (SEQ ID NO:53), PTGS2-P2-PTGFR sequence (SEQ ID NO:54), and complete AAV expression cassette for PDG2alpha biosynthesis (SEQ ID NO:58). Also included are additional riboswitches that can be used in the practice of the present invention (SEQ ID NO:64-67).

DETAILED DESCRIPTION OF THE INVENTION

The present disclosure provides modified riboswitches (e.g., modified miRNA switches) and systems containing said modified riboswitches for use in the treatment of diseases, specifically eye diseases, and more specifically AMD and glaucoma. The present invention aims to provide novel systems to regulate gene expression in the eye, using novel modified microRNA (riboswitches) as a regulatory tool. Such genetic constructs, and kits or methods utilizing same, may be of use in controlling gene expression, for example in the production of recombinant proteins or transgenes involved in the regulation of specific compounds, for example, prostaglandins in the eye.

Such RNA-based systems (riboswitches) offer three distinct advantages over inducible promoter systems. First, they have a small genetic footprint (~100 bp) and so can be easily incorporated within the rAAV vector genome without sacrificing significant amounts of coding capacity. Second, these devices act in cis, limiting the likelihood of an immune response as no protein cofactors are required for functionality. Last, the aptamer domain of a riboswitch can be engineered to respond to almost any activating ligand, including proteins, small molecule drugs or ions.

One embodiment of this technology is to modulate expression of transgenes involved in prostaglandin F2α synthesis in the eye to regulate intraocular pressure in glaucoma patients. A second embodiment is to modulate the expression of an anti-VEGF recombinant fusion protein in the eye, namely Aflibercept (Eylea) in order to prevent choroidal neovascularization (CNV).

The technology in some embodiments uses constructs including modified riboswitches, which are ligand-controlled gene regulatory elements that allow for either switching on or off a transgene of interest in order to regulate transgene expression. The mechanisms by which riboswitches function include, without limitation, the ability to function as a ribozyme and cleave itself if a sufficient concentration of its ligand is present, the ability to fold the mRNA in such a way the ribosomal binding site is inaccessible and prevents translation from occurring, and/or the ability to affect the splicing of the pre-mRNA molecule. Embodiments comprising the modified riboswitches and constructs or cassettes containing such riboswitches are contemplated herein.

MicroRNAs are a class of non-coding RNAs that play key roles in the regulation of gene expression. Acting at the post-transcriptional level, microRNA (miRNA) genes are transcribed by RNA polymerase II as large primary transcripts (pri-mRNA) that are processed by a protein complex containing the RNase III enzyme Drosha, to form a precursor microRNA (pre-microRNA). In the present invention, the pri-microRNA have been designed to be processed into a pre-mRNA that can act as a silencing RNA to silence gene expression.

Figure 1:
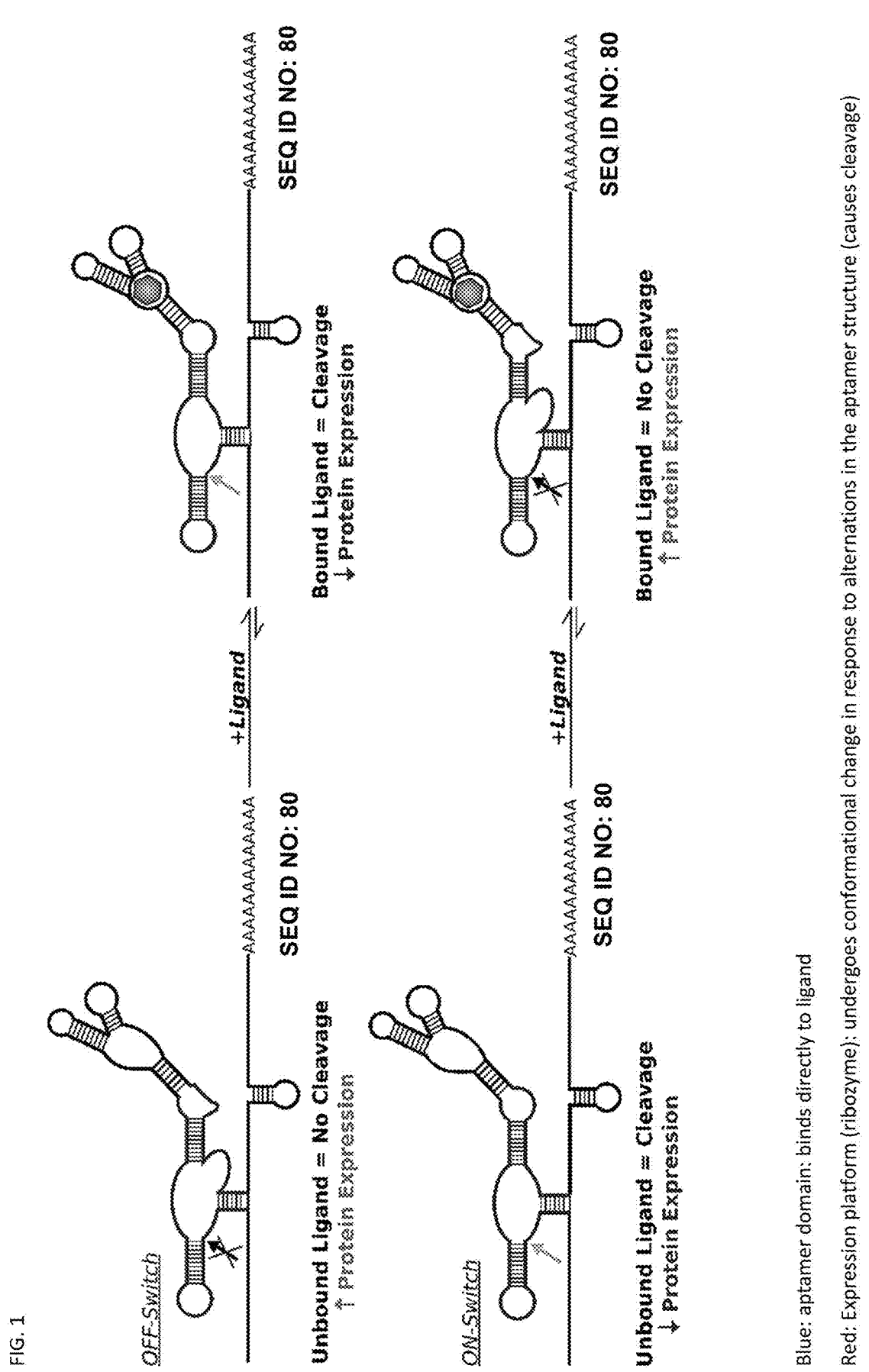
FIG. 1 is a schematic demonstrating the OFF-Switch and ON-Switch riboswitches.

Riboswitches are divided into two parts: an aptamer and an expression platform. The aptamer is a "sensor" to which a target small molecule ligand binds; the expression platform undergoes structural changes in response to the changes in the aptamer sensor. Binding of the aptamer domain causes conformational changes within the expression platform, this conformational change regulates gene expression by turning the gene off or on. This is illustrated in FIG. 1. The aptamer is shown in blue; the expression platform, in red; the ligand in green. Often toxic concentrations of ligand are necessary to "flip the switch". However, the present invention provides modified riboswitches that can turn on or off gene expression in the retina for use in ocular gene therapy using non-toxic levels of ligand.

A number of exemplary riboswitches are described herein, namely a self-targeting ligand inactivating microRNA (SLIM) embodiments. A self-targeting ligand inactivating microRNA (SLIM) is an ON-type switch that mediates an increase in gene expression in the presence of the ligand (See, e.g., FIGS. 2A and 2B). Compositions and methods of using this technology to treat AMD and Glaucoma are provided herein. Specifically, this SLIM system can be used to intermittently switch on expression of the VEGF inhibitor. Compositions and methods of use of this technology are contemplated for the treatment of glaucoma, where it would be beneficial to intermittently turn off or lower expression of the prostaglandin in the eye of a patient are contemplated. Both are described in more detail below.

SLIM: ON-Type Modified Riboswitch for Modifying Gene Expression

The present invention in one embodiment provides a self-targeting ligand inactivating microRNA (SLIM) switch which is an ON type riboswitch that can be incorporated into an expression construct to regulate expression of a transgene of interest. The SLIM switch (smiRNA in FIGS. 2A and B) requires the basal region of a pri-miRNA to be replaced with an aptamer that can bind to a target ligand. This sequence is cloned into either the 3'- or 5' untranslated region of an expression construct. Binding of the ligand alters the conformation of the aptamer and pri-miRNA, resulting in non-cleavage of the pri-miRNA by Drosha. A target miRNA sequence is cloned into either the 3' or 5' untranslated region which allows for a second level of regulation, in which the pri-miRNA when cleaved in the absence of ligand is processed into a miRNA that can bind to the target miRNA sequence and prevent transcription. Once the SLIM switch is incorporated within an expression construct, the transgene expression is turned off when ligand is not present, and is turned on once the ligand binds to the aptamer.

SLIM switches function by regulating gene expression at the post-transcriptional level. In conditions in which the activating ligand is absent, the pri-miRNA will be cleaved by Drosha from the nascent transcript. This miRNA will be processed and act as a second mechanism of gene silencing, through binding of the complementary target sites. When the activating ligand is present, gene expression is unaltered and the gene is expressed.

In one embodiment, an exogenous nucleic acid construct for regulating expression of a transgene is provided. The construct encodes (a) a transgene, (b) a smiRNA switch (SLIM switch) located within the untranslated region of the transgene, wherein the smiRNA switch comprises an aptamer domain capable of binding to a ligand and a pri-miRNA sequence, and (c) at least one miRNA target sequence complementary to at least a portion of the pri-miRNA. The miRNA switch regulates expression of the transgene by both (1) regulation of the cleavage of the mRNA (which removes either the poly-A tail or 5'-cap destabilizing the RNA), and (2) regulating cleavage of the pri-miRNA from the smiRNA, wherein at least a portion of the cleaved pri-miRNA is processed and binds to the at least one miRNA target sequences silencing the transgene expression.

As discussed above, in the absence of ligand, the pri-miRNA is cleaved from the transcript and binds to the at least one miRNA target sequence which silences the transgene. This is depicted in FIG. 2B. In some embodiments, the at least one miRNA target sequence complementary to at least a portion of the pri-miRNA (c) discussed above is encompassed in the transgene (as depicted in the bottom figure of FIG. 2B). In other words, the SLIM switch can be generated toward the transgene itself.

In a preferred embodiment, the heterologous self-targeting ligand inactivating microRNA (SLIM) switch comprises (a) a target gene of interest, (b) at least one smiRNA switch located within the untranslated region of the transgene, wherein the smiRNA switch comprises an aptamer domain capable of binding to a ligand and a pri-miRNA, wherein the smiRNA switch regulates expression of the transgene by both (1) regulation of the cleavage of the mRNA of the transgene, and (b) regulating cleavage of the pri-miRNA from the smiRNA, wherein at least a portion of the cleaved pri-miRNA binds to a portion of the transgene (in other words, a portion of the transgene acts as the miRNA targeting sequence) silencing the transgene expression. Suitable riboswitches are described in FIGS. 18 and 19, which also include the portion of the Eylea transgene or Flt1 transgene each riboswitch targets (e.g. SLIM switch for Eylea Target 1 (e.g., SEQ ID NO: 21, or 26 or 31) targets a portion of Eylea found in Eylea target 1 (SEQ ID NO:70), SLIM switch for Target 2 (e.g. SEQ ID NO:22, 27, 32) target Eylea Target 2 (SEQ ID NO:71) and so forth (e.g. SLIM switch for Eylea 3 targets Eylea Target 3, SLIM switch for Eylea 4 targets Eylea Target 4, SLIM switch for Eylea Target 5 targets Eylea Target 5, SLIM switch for Flt1 Target 1 targets Flt1 Target 1, etc.). One or more SLIM switches can be combined within the exogenous expression constructs for use in the methods described herein (e.g., SLIM switch for Target 1, Target 2, Target 3, Target 4, and Target 5 of Elyea or Sflt1 can be combined in any combination for a construct to target (e.g. SLIM 1 and 2; SLIM 1 and 3; SLIM 1 and 4; SLIM 1 and 5; SLIM 2 and 3; SLIM 2 and 4; SLIM 2 and 5; SLIM 3 and 4; SLIM 3 and 5; SLIM 4 and 5; SLIM 1, 2, and 3; SLIM 1, 2 and 4; SLIM 1, 2 and 5; SLIM 1, 3, and 4; SLIM 1, 3 and 5; SLIM 1, 4 and 5; SLIM 2, 3 and 4; SLIM 2, 3 and 5; SLIM 2, 4 and 5; SLIM 3, 4 and 5; SLIM 1, 2, 3, and 4; SLIM 1, 2, 3 and 5; SLIM 2, 3, 4 and 5; and SLIM 1, 2, 3, 4 and 5) of the SLIM found in FIGS. 18-19.

In one embodiment, an exogenous nucleic acid construct for regulating expression of a transgene by modulating the mRNA of the transgene is provided. The nucleic acid encoding: (a) a target gene of interest, (b) at least one smiRNA switch located within the untranslated region of the transgene, wherein the smiRNA switch comprises an aptamer domain capable of binding to a ligand and a pri-miRNA, wherein the smiRNA switch regulates expression of the transgene by both (1) regulation of the cleavage of the mRNA of the transgene, and (b) regulating cleavage of the pri-miRNA from the smiRNA, wherein at least a portion of the cleaved pri-miRNA binds to a portion of the transgene (as a miRNA targeting sequence) silencing the transgene expression. In a preferred embodiment, the exogenous nucleic acid construct is a AAV viral vector.

In some embodiments, the SLIM switch generated against Eylea or sFlt1 are used for the treatment of AMD as shown in the sequences described in FIGS. 18 and 19.

Figure 2A:
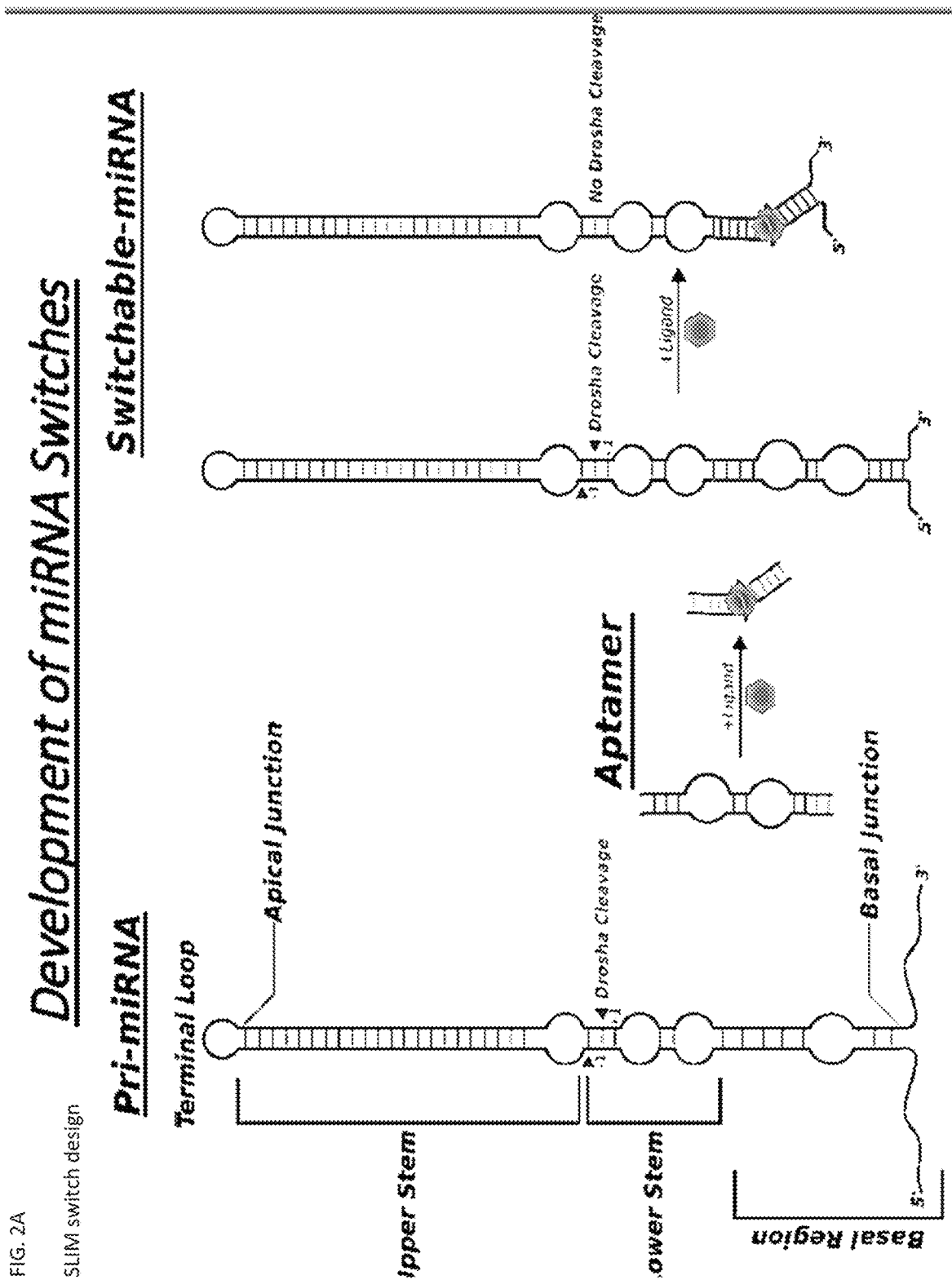
FIG. 2A is a schematic representing the development of a SLIM switch (e.g. switchable miRNA) using a pri-miRNA and an aptamer.

In one embodiment, an exogenous nucleic acid construct encodes: the SLIM switch, transgene, and at least one target miRNA sequence. Design of such SLIM switches is depicted in FIG. 2A. In one example, a suitable SLIM switch (smiRNA) encodes an aptamer domain and a pri-miRNA. Suitable aptamer domain is adapted from the aptamer domain of an ON-type riboswitch known in the art, and include but are not limited to, for example, L2Bulge18tc (for example, but not limited to, SEQ ID NO:12), K19 (For example, SEQ ID NO:15), L2Bulge9 (for example, SEQ ID NO:11), among others. Suitable aptamer domains are depicted in FIG. 3 and described in the specification below.

Suitable SLIM switches include, but are not limited to our developed Theo-SLIM (SEQ ID NO: 1) which is depicted in FIG. 3 (smiRNA), and Tet-SLIM (SEQ ID NO:17) as described herein. These SLIM switches have been engineered as to not cross-react with any genes in the human genome, and thus should not cause any off-target effects.

Additional SLIM switches are depicted in FIGS. 18-23.

The term "exogenous" as it refers to nucleic acid is foreign to (not normally found in nature in) the prokaryotic host cell, or a recombinant nucleic acid that is not normally found in the prokaryotic host cell. In some embodiments, the exogenous nucleic acid sequence is a heterologous sequence comprising sequences from a number of different sources or organisms. The term exogenous also encompasses a construct that include sequences from a different species than the species the construct will be used. For example, a rAAV construct of the present invention will include not only endogenous AAV sequences, but exogenous sequences from human or other sources that are not native to the AAV virus.

The nucleic acid constructs provided herein are synthetic engineered constructions containing non-naturally occurring sequences.

The term "transgene" and "target gene of interest" are used interchangeably to refer to an exogenous gene which is to be expressed in the desired cell by use of the constructs of the present invention.

Further, suitable aptamers can be designed against various ligands and incorporated into the SLIM switches by linking the aptamer to a pri-miRNA sequence (See, e.g., FIG. 2A).

In some embodiments, the constructs comprise a transgene and a SLIM switch. In some of these embodiments, the transgene acts as the miRNA target sequence for the SLIM switch. In other embodiments, the constructs further comprises the SLIM switch which also contain at least one target miRNA sequence, preferably from about 1-4 target miRNA sequences in the 3' or 5' UTR. For example, FIG. 2B (top figure) shows a suitable design of such construct. Suitable ligands are discussed more below, and specifically include ligands that are able to cross the blood retinal barrier, for example, tetracycline, theophylline and guanine.

In some embodiments, the construct comprises at least one target miRNA sequence, alternatively at least two, alternatively at least three, alternatively at least 4 target miRNA sequences. The number of target miRNA sequences added may depend on the vector used, for example, in the use of a rAAV vector, a suitably number of target miRNA include, for example, from 1-5. Adding more target sites would limit the available coding sequences as there is a limit to the size of the rAAV vectors, thus depending on the size and sequence of the transgene may also alter the number of target miRNA sequences added.

In one embodiment, when the smiRNA is SEQ. ID NO. 1, the target miRNA sequence is encoded in SEQ ID NO: 10 (GAGAGAATCTTCTTTCTGTCTATAAAA). In one suitable embodiment, the construct contains at least three target miRNA sequence, for example, as found in SEQ ID NO: 2.

In one embodiment, the construct comprises a suitable transgene in which the expression of the transgene can be induced by administration of the ligand. For example, as described in more detail below, the transgene may be a VEGF inhibitor, specifically a VEGF inhibitor which can be induced to be expressed in the eye for the treatment of AMD. Specifically, a suitable VEGF inhibitor is aflibercept, which is encoded by the cDNA found in SEQ ID NO: 8.

In another embodiment, the aptamer domain and the pri-miRNA are encoded within SEQ ID NO:1. In some embodiments, the construct contains other sequences found within constructs, for example, promoters, enhancers, WPRE elements, and the like. One skilled in the art would be able to incorporate other known elements necessary for transgene expression from a nucleic acid construct.

In some embodiments, the construct is an adeno-associated virus (rAAV), a lentivirus, an adnovirus, a plasmid, a herpes simplex virus, a baculovirus, a bacteriophage, among others. Preferably, the construct is an adeno-associated virus. A suitable rAAV construct is demonstrated in FIG. 2 which incorporates the transgene for aflibercept, a Theo- SLIM switch and 3 miRNA target sequences, for example, the sequence encoded in SEQ ID NO:9 or SEQ ID NO:19.

In some embodiments, the SLIM switch requires the basal region of a pri-miRNA to be replaced with an aptamer. This sequence is cloned into either the 3'- or 5' untranslated region of an expression cassette. Additionally, miRNA target sites that are complementary to the sequence of the mature miRNA can be included in one or multiple copies at either the 5' or 3' untranslated region of the cassette.

Self-targeting Ligand Inactivated miRNAs (SLIM) switches function by regulating gene expression at the post-transcriptional level. In conditions when the activating ligand is absent, the pri-miRNA will be cleaved by drosha from the nascent transcript. This miRNA will be processed and act as the second mechanism of gene silencing, through binding of the complementary target sites. When the activating ligand is provided, gene expression is unaltered.

Multiple copies of each riboswitch can be included into the 3'-untranslated region of the gene of interest. Each riboswitch appears to have an optimal number of copies as shown in Table 1. Furthermore, in some embodiments, multiple copies of miRNA target sites can be included in the 3' or 5' untranslated region. The synthetic riboswitches comprise an aptamer and an expression platform and rely on changes in the expression platform activity for regulating gene expression. The miRNA target sites are sequences in the therapeutic cassette (construct) that are recognized by the mature miRNA/siRNA. As discussed more below, the miRNA target sites may be encompassed within the transgene. In other words, the cleaved and processed siRNA from the riboswitch binds to the transgene and inhibits its expression.

Alternatively, the SLIM switch can be generated towards the transgene itself, with Eylea and sFlt1 for the treatment of AMD, the sequences are found in FIGS. 16-18, 19 and 23.

In one embodiment, the nucleic acid construct comprises a target gene of interest, for example, a VEGF inhibitor (e.g. Eylea (SEQ ID NO:20) or sFLT1 (SEQ ID NO:36) and at least one miRNA SLIM switch located within the untranslated region of the target gene (e.g. at least one selected from SEQ ID NO:21-35 or SEQ ID NO:37-51, respectively of the VEGF inhibitors).

In some embodiments, the nucleic acid construct is an rAAV vector comprising the Eylea gene (e.g. SEQ ID NO:19). For example, SEQ ID NO:19 provides a complete AAV expression vector for the expression of Eylea using a SLIM switch. Within SEQ ID NO:19, X marks positions in which a SLIM sequence may be inserted. Suitable SLIM sequences that may be inserted can be found in FIG. 18, and include, but are not limited to, 6S-Folinic Acid-responsive SLIM (miRNA) switches, including, for example, SEQ ID NO: 21, 22, 23, 24, and 25 (activated by the ligand 6S-Folinic acid), Theophylline-responsive SLIM, for example, SEQ ID NO:26, 27, 28, 29 and 30 (activated by ligand theophylline), or Tetracycline-responsive SLIM, for example, SEQ ID NO:31, 32, 33, 34, and 35 (activated by ligand tetracycline). In some embodiments, from 1-5 SLIM sequences are inserted within the AAV expression vector, alternatively from 1-3 SLIM sequences. For example, SEQ ID NO:19 may incorporate 1-5 copies of SEQ ID NO:21, alternatively 1-5 copies of SEQ ID NO:22, alternatively 1-5 copies of SEQ ID NO: 23, alternatively 1-5 copies of SEQ ID NO:24, alternatively 1-5 copies of SEQ ID NO:25, alternatively 1-5 copies of SEQ ID NO:26, alternatively 1-5 copies of SEQ ID NO:27, alternatively 1-5 copies of SEQ ID NO:28, alternatively 1-5 copies of SEQ ID NO:29, alternatively 1-5 copies of SEQ ID NO:30, alternatively 1-5 copies of SEQ ID NO:31, alternatively 1-5 copies of SEQ ID NO:32, alternatively 1-5 copies of SEQ ID NO:33, alternatively 1-5 copies of SEQ ID NO:34, alternatively 1-5 copies of SEQ ID NO:35.

In another embodiment, the nucleic acid construct comprises a target gene of interest, for example, a VEGF inhibitor sFLT1 (SEQ ID NO:36) and at least one smiRNA SLIM switch located within the untranslated region of the target gene (e.g. at least one selected from SEQ ID NO:37-51).

In some embodiments, the nucleic acid construct comprises the sFLT1 gene (SEQ ID NO:36). sFLT1 may be inserted within a vector, for example a rAAV vector, and flanked by X which marks positions in which a SLIM sequence may be inserted. Suitable SLIM sequences that may be inserted can be found in FIG. 18, and include, but are not limited to, 6S-Folinic Acid-responsive SLIM (miRNA) switches, including, for example, SEQ ID NO: 37, 38, 39, 40, 41 (activated by the ligand 6S-Folinic acid), Theophylline-responsive SLIM, for example, SEQ ID NO:42, 43, 44, 45, 46 (activated by ligand theophylline), or Tetracycline-responsive SLIM, for example, SEQ ID NO:47, 48, 49, 50, and 51 (activated by ligand tetracycline). In some embodiments, from 1-5 SLIM sequences are inserted within the construct, alternatively from 1-3 SLIM sequences. For example, SEQ ID NO:36 may incorporate as X from 1-5 copies of SEQ ID NO:37, alternatively from 1-5 copies of SEQ ID NO:38, alternatively from 1-5 copies of SEQ ID NO:39, alternatively from 1-5 copies of SEQ ID NO:40, alternatively from 1-5 copies of SEQ ID NO:41, alternatively from 1-5 copies of SEQ ID NO:42, alternatively from 1-5 copies of SEQ ID NO:43, alternatively from 1-5 copies of SEQ ID NO:44, alternatively from 1-5 copies of SEQ ID NO:45, alternatively from 1-5 copies of SEQ ID NO:46, alternatively from 1-5 copies of SEQ ID NO:47, alternatively from 1-5 copies of SEQ ID NO:48, alternatively from 1-5 copies of SEQ ID NO:49, alternatively from 1-5 copies of SEQ ID NO:50, or alternatively from 1-5 copies of SEQ ID NO:51. Alternative combinations of SLIM sequences are contemplated (e.g. for example from 1-5 SLIM sequences selected from SEQ ID NO:36, 37, 38, 39, 40, and 41). Suitable, one would preferably use SLIM sequences activated by the same ligand in the construct, for example 1-5 SLIM sequences that are active by the tetracycline ligand.

Figure 21:
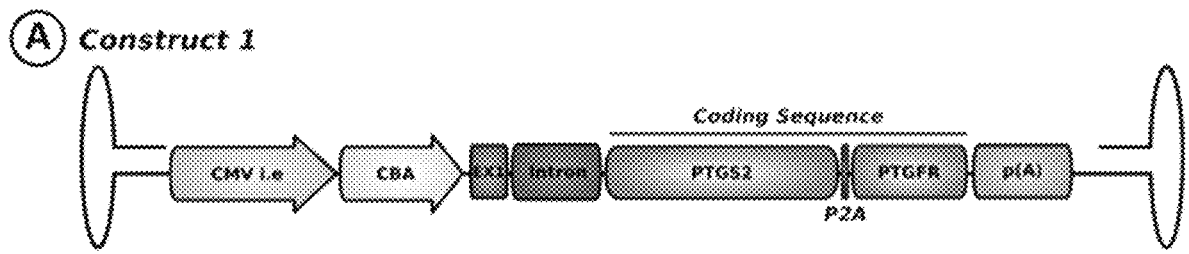
FIG. 21 is a depiction of a vector construct of a vector (e.g. AAV vector) comprising prostaglandin endoperoxide synthase 2 (PTGS2) and PTGFR.
Figure 22:
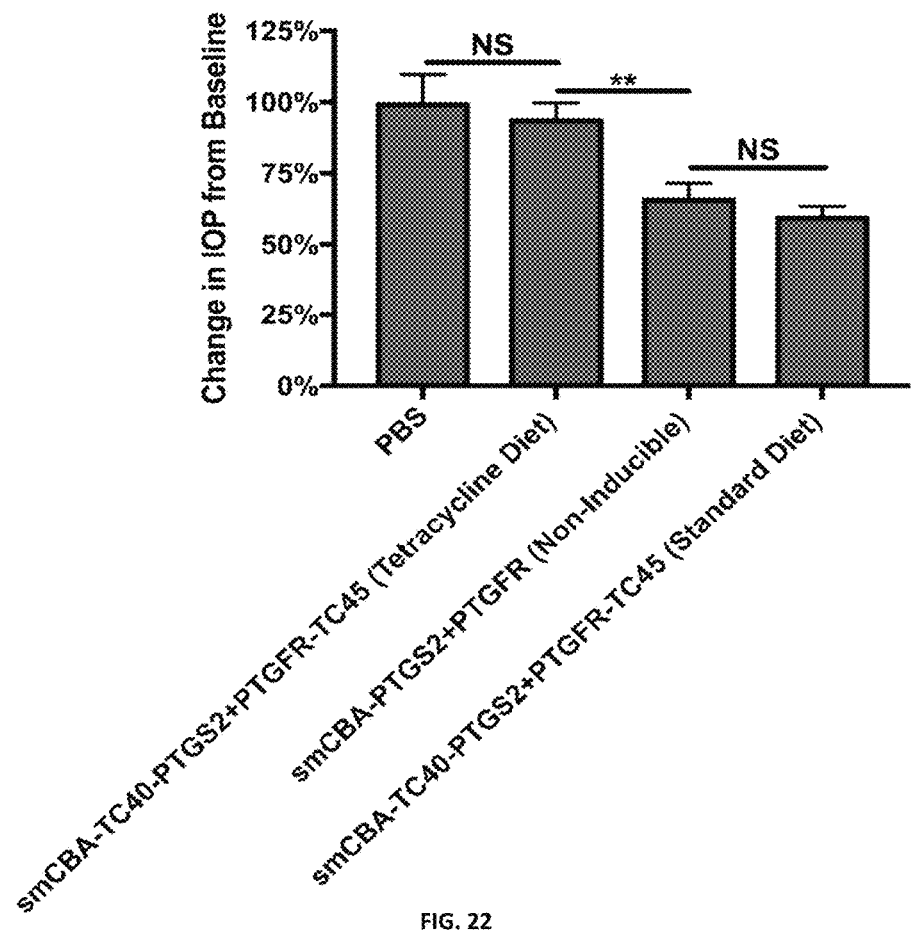
FIG. 22 is a graph depicting the change in intraocular pressure (TOP) from baseline in mice after treatment with an AAV with SLIM riboswitch and administration of the ligand tetracycline.

In another embodiment depicted in FIG. 21, a nucleic acid construct comprises PTGS2 (SEQ ID NO:52) and PTGFR (SEQ ID NO:53) (depicted in combination in SEQ ID NO:54 as PTGS2-P2A-PTGFR). Suitable nucleic acid construct is depicted in FIG. 23 as SEQ ID NO:58, a AAV expression vector comprising PGF2alpha biosynthesis regulatory genes (PTGS2 (SEQ ID NO:60) and PTGFR (SEQ ID NO:62) including two synthetic riboswitches TC40 (SEQ ID NO:59) and TC45 (SEQ ID NO:63). Suitable use of such construct is for the treatment of glaucoma.

Ligands

The specific ligand to be used depends on the specific application and aptamer incorporated into the SLIM switches. For the treatment of eye diseases and disorders, ligands that are able to cross the blood retinal barrier are preferred. Suitable aptamers that can cross the blood retinal barrier include, but are not limited to, for example, tetracycline, theophylline, guanine, galactitol, progesterone, mannitol, estradiol, dopamine, quinidine, urea, digoxin, uracil, verapamil, thiourea, moxifloxacin, thymine, levofloxin, corticosterone, acetazolamide, testosterone, doxycycline, and combinations thereof.

In a preferred embodiment, the ligand is selected from the group consisting of tetracycline, theophylline and guanine.

Suitable routes of administration of the ligands are known in the art and include, oral administering, administering via the eye (e.g., eyedrops) and the like.

Treatment of Eye Diseases

The constructs of the present technology are particularly useful for gene therapy for the treatment of eye diseases. The eye is a particularly good target for this type of gene therapy for a number of reasons. The eye is a highly specialized organ which has evolved to transduce light stimuli into electrical signals and to relay those signals to the visual cortex. Light sensation and image formation is mediated through the activation of photoreceptor cells located in the outermost layer of the neurosensory retina, where incident light focused by the cornea and lens results in the activation of a signaling cascade and the propagation of an electrical impulse. Despite its complexity the eye has many traits which make it an attractive organ for gene therapy: it is relatively immune privileged, has a small compartment size, is easily visualized and examined, and readily accessible with minimal risk to patients undergoing surgery. The retina (AMD) or the cornea (Glaucoma) are the primary targets for gene therapy treatments. Vector delivery is usually achieved through injection of a fluid suspension containing the therapeutic particles into the anatomically constrained space adjacent to the target cells. A rAAV.SLIM.αVEGF or rAAV.SLIM.sFLT1 vector would be most beneficial if targeted towards cells of the inner retina, including retinal ganglion cells and Müller glia, and as such would be administered via intravitreal injection. The rAAV.S-LIM.PTGS2-P2-PTGFR vector would be most beneficial if targeted towards cells of the cornea and anterior chamber, including corneal endothelial cells, and as such would be administered via intracameral injection. Numerous rAAV clinical trials using rAAV for ocular gene therapy applications have been successfully completed; however, all trials to date have utilized a sub-retinal delivery approach designed to target photoreceptors. A current phase I/II clinical trial (NCT01494805) is underway utilizing rAAV-mediated overexpression of soluble fms-like tyrosine kinase-1 (sFLT), a soluble receptor of VEGF, for the treatment of AMD. Expression of sFLT in this trial is constitutive, and cannot be regulated, unlike the proposed rAAV.SLIM.αVEGF and rAAV.SLIM.sFLT1 technology described herein. No rAAV-based gene therapy clinical trials are underway for the treatment of glaucoma.

Treatment of AMD

The present invention provides methods of treating age-related macular degeneration by inhibiting, reducing or alleviating at least one symptom of AMD. AMD is a disease involving multiple tissue layers within the eye, including the choroid, retinal pigment epithelium and the neurosensory retina, and occurs in two forms. Dry AMD is a non-proliferative disease state characterized by progressive geographic atrophy of the central retina. In approximately 10-15% of patients the disease progresses to a wet form, characterized by abnormal growth of blood vessels from the choroid into the subretinal space. Choroidal neovascularization (CNV) results primarily as a result of increased intraocular concentrations of VEGF and is the major vision-threatening symptom of AMD. Administration of anti-VEGF agents is known to significantly reduce the incidence of CNV and is the current gold-standard treatment AMD. The treatment regimen is invasive, however, requiring repetitive (e.g. monthly or bimonthly) intravitreal injection of purified recombinant anti-VEGF protein.

The proposed rAAV.SLIM.αVEGF technology would act to significantly reduce the incidence of CNV formation in AMD patients, and consequently prevent vision loss. Critically, the inclusion of the SLIM technology would allow for anti-VEGF expression to be controlled through dosing of the activating ligand.

The rAAV.SLIM.αVEGF vector technology of the present invention would act to significantly reduce the incidence of CNV formation in AMD patients, and consequently prevent vision loss. Critically, the inclusion of the SLIM technology would allow for anti-VEGF expression to be controlled through dosing of the activating ligand.

The present invention provides methods of treating, reducing, alleviating or inhibiting at least one symptom of AMD comprising administering to the eye of a subject a construct comprising a VEGF inhibitor and a SLIM riboswitch as described herein (including, e.g., rAAV.SLIM.αVEGF or rAAV.SLIM.sFLT1 vector), and further administering a therapeutically effective amount of the ligand. The SLIM riboswitch can determine which ligand is used as described in more detail herein. Suitably, the treatment results in the reduction, alleviation or inhibition of one or more symptom of AMD, for example, a reduction or inhibition of the development of CNV.

In one embodiment, the method of treating, inhibiting or reducing at least one symptom of AMD comprises administering a construct comprising one or more ON-type riboswitch operably connected to a transgene encoding a VEGF inhibitor and administering a therapeutically effective amount of the ligand. Suitable ON-type riboswitches are known in the art and include, but are not limited to, for example, L2Bulge18tc (SEQ ID NO:12), K19 (SEQ ID NO:15), and L2Bulge 9 (SEQ ID NO:11). Further, the construct may encode an optimal copy number of the ON-type riboswitches which can be incorporated into the construct. The optimal copy number of the riboswitch is detailed in Table. 1. For example a construct for the treatment of AMD may comprise from 1-3 L2Bulge18tc riboswitches and a VEGF inhibitor.

TABLE 1

ON-TYPE Switches and SLIM switches

| Riboswitches | Activating Ligand | Optimal Copy number | Dynamic Range | SEQ ID NO: |
|---|---|---|---|---|
| L2Bulge18tc | Tetracycline | 3 | 12.5 | 4.3-fold | 12 |
| K19 | Tetracycline | 1 | 39.1 | 1.5-fold | 15 |
| L2Bulge9 | Theophylline | 3 | 37.9 | 1.7-fold | 11 |
| Theo-SLIM | Theophylline | 1 | 7.2 | 10.9-fold | 1 |
| Tet-SLIM | Tetracycline | 1 | 36.4 | 2.3-fold | 17 |

The SLIM riboswitches can be incorporated into constructs of the present invention to alter gene expression of the transgene by administration of a therapeutically effective amount of the ligand. By "therapeutically effective amount" we mean an amount or dosage of the ligand that is able to alter the expression level of the transgene product in a cell. One skilled in the art will be able to titrate and determine a therapeutically effective amount to produce the proper response and result in a reduction of the symptoms of the desired disease to be treated. A therapeutically effective amount also maintains that the level of ligand is in a non-toxic dose to the subject. Suitably, the dosage may be given daily, weekly or monthly depending on the particular requirements for expression in the subject.

Treatment of Glaucoma

The present invention provides for the first time higher functioning genetic switches in a retinal model which can be used to regulate transgenes within the eye to treat eye diseases. The SLIM switches described above have the potential to have an increased dynamic range over traditional riboswitches and can be used for the treatment, inhibition or amelioration of one or more symptom of glaucoma, including high intraocular pressure. Prostaglandin synthesis will be regulated by orally ingesting the activating ligand. The dose of the activating ligand will be determined by intraocular pressure (TOP) readings of the patient through the use of a rebound tonometer.

The present disclosure provides methods of treating glaucoma comprising gene therapy using an adeno-associated virus encoding the construct comprising a SLIM switch and one or more genes that regulate prostaglandin synthesis as described herein. In another embodiment, the disclosure provides a method of treating glaucoma comprising administering an adeno-associated virus encoding a construct comprising one or more genes that regulate prostaglandin synthesis and at least one ON-type riboswitch (SLIM). FIGS. 21 and 23 provide one such example of the AAV vector encoding genes necessary for regulation of prostaglandin synthesis and suitable SLIM riboswitches for use in the present invention.

Glaucoma is typified by elevated intra-ocular pressure (TOP) leading to progressive loss of retinal ganglion cells and, ultimately severe visual impairment. Increased IOP results from an imbalance between the production of aqueous humour by the ciliary body in the eye's posterior chamber and its drainage through the trabecular meshwork in the anterior chamber. Glaucoma can be categorized based on whether the drainage through the trabecular meshwork is completely (closed angle) or partially (open angle) blocked. Open angel glaucoma is most common and usually presents with no symptoms other than slow progressive vision loss. Closed angle glaucoma is loss common and is considered to be a medical emergency, presenting with acute eye pain, headaches, blurred vision, excessive lacrimation nausea and vomiting.

Due to its chronic nature, the proposed rAAV.S-LIM.PTGS2-P2-PTGFR (SEQ ID NO:58) technology would be appropriate for the treatment of glaucoma.

In one embodiment, a method of reducing, inhibiting or ameliorating at least one symptom of glaucoma is provided. The method comprises administering an exogenous nucleic acid construct to the eye of the subject. In one embodiment, the exogenous nucleic acid construct encodes a transgene that regulates prostaglandin 2α synthesis and at least one smiRNA riboswitch. In another embodiment, the exogenous nucleic acid construct encodes: (i) a transgene that regulates prostaglandin synthesis (e.g., prostaglandin endoperoxide synthase 2 (PTGS2); (ii) a smiRNA switch located within the untranslated region of the transgene, wherein the smiRNA switch comprises at least two riboswitches flanking a pri-miRNA, each riboswitch comprising an aptamer operably linked to an expression platform, and (iii) at least one miRNA target sequence complementary to at least a portion of the pri-miRNA, wherein the transgene is incorporated into cells of the subject and express the transgene, and (b) administering a therapeutically effective amount of the ligand that is able to bind to the aptamer in order to regulate expression of the transgene within the eye to reduce, inhibit or ameliorate at least one symptom of glaucoma. In one embodiment, the symptom is high intraocular pressure.

Suitable ligands include ligands that can cross the blood retinal barrier, as described herein.

Suitably, the transgene that regulates prostaglandin 2α synthesis includes, but is not limited to, for example, PTGS2 (SEQ ID NO:52) among others. Other suitable transgenes are known in the art.

Kits

This disclosure provides kits. The kits can be suitable for use in the methods described herein. In one aspects, a kit can include a rAAV vector comprising the constructs as described herein, for example, a SLIM switch containing construct. In some aspects, the kit can include a construct comprising rAAV vector encoding a VEGF inhibitor as described herein. In other aspects, the kit can include a construct comprising a rAAV vector encoding one or more genes involved in the regulation of prostaglandin synthesis as described herein. Further, the kits may comprise one or more doses of the ligand to be administered after initial administration of the rAAV vector. Instructions on the timing of the dosages and proper administration methods may be provided.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "treating" or "treatment" includes, but is not limited to, reducing, inhibiting or preventing one or more signs or symptoms associated with the disease or disorder. For example, treating glaucoma include, for example, reduction in the intraocular eye pressure (e.g. the symptom of glaucoma being treated is high intraocular pressure).

The terms "effective amount" or "therapeutically effective amount" refer to an amount sufficient to effect beneficial or desirable biological and/or clinical results.

"Expression platform" Within the context of the disclosure, the portion of the modified riboswitch which mediates the effect on the nucleic acid expression is known as the expression platform. Preferably, the expression platform is operably linked to the aptamer domain of the riboswitch, preferably structurally linked, most preferably by a nucleic acid linker. Most preferred is that the aptamer domain is linked to the expression platform by a nucleic acid sequence. Preferably, the stem configuration of the portion of the expression platform changes configuration upon binding of a ligand, such that a change in the configuration of the stem structure results in a corresponding change in the structure of the expression platform, between a first configuration which enhances expression of the nucleic acid sequence and a second configuration which inhibits expression of the nucleic acid sequence.

"Genetic construct" can include nucleic acid sequences that permit it to replicate in the host cell. Examples include, but are not limited to a plasmid, cosmid, bacteriophage, or virus that carries exogenous DNA into a cell. A genetic construct can also include additional selectable marker genes and other genetic elements known in the art. A genetic construct can preferably transduce, transform or infect a cell, thereby causing the cell to express the nucleic acids and/or proteins encoded by the vector.

"Operably linked" a first element is operably linked with a second element when the first element is placed in a functional relationship with functional relationship with the second element. For instance, a aptamer is operably linked to an expression platform when the binding of the aptamer to its ligand causes conformational changes to the expression platform which alters the function of the expression platform (for example, if the expression platform is a ribozyme, binding of the aptamer to the ligand can activate the ribozyme activity). Generally, operably linked DNA sequences are contiguous and, where necessary to join two protein coding regions, in the same reading frame.

It is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Ability to Regulate Gene Expression In Vivo in the Eye

This Example demonstrates that six riboswitches respond to a ligand in cell culture and in vivo when deliver to the mouse retina.

Six small (~100 bp) riboswitches (K19, Tc40×45, GuaM8HDV, L2Bulge18tc, L2Bulge9 and Theo6HDV) responded to a ligand in cell culture, and in vivo when delivered to the mouse retina using a rAAV2 vector.

The riboswitches were evaluated in HEK293T cells to determine optimal copy number (largest dynamic range) and dose-responsiveness to its activating ligand using a dual luciferase assay. The ligand used were tetracycline and theophylline.

Cell culture experiments revealed significant changes in firefly luminescence in response to dosing of the appropriate ligand ($p<0.01$, One-way ANOVA, N=4 all groups).

Next, the optimal copy number of each riboswitch was cloned into a rAAV GFP reporter cassette and packaged in an AAV2 capsid. Each GFP-riboswitch cassette was injected intravitreally into C57Bl/6j mice in combination with an AAV2 control vector harboring a non-inducible mCherry reporter gene. Four weeks post-injection, mCherry and GFP fluorescence levels were quantified in vivo using a custom 'Multiline' confocal scanning laser ophthalmoscope (cSLO). Mice subsequently received a dose of 1000 mg/kg of its activating ligand (tetracycline, theophylline), and fluorescence levels were quantified 2 and 24 hours post-gavage.

Figure 6B:
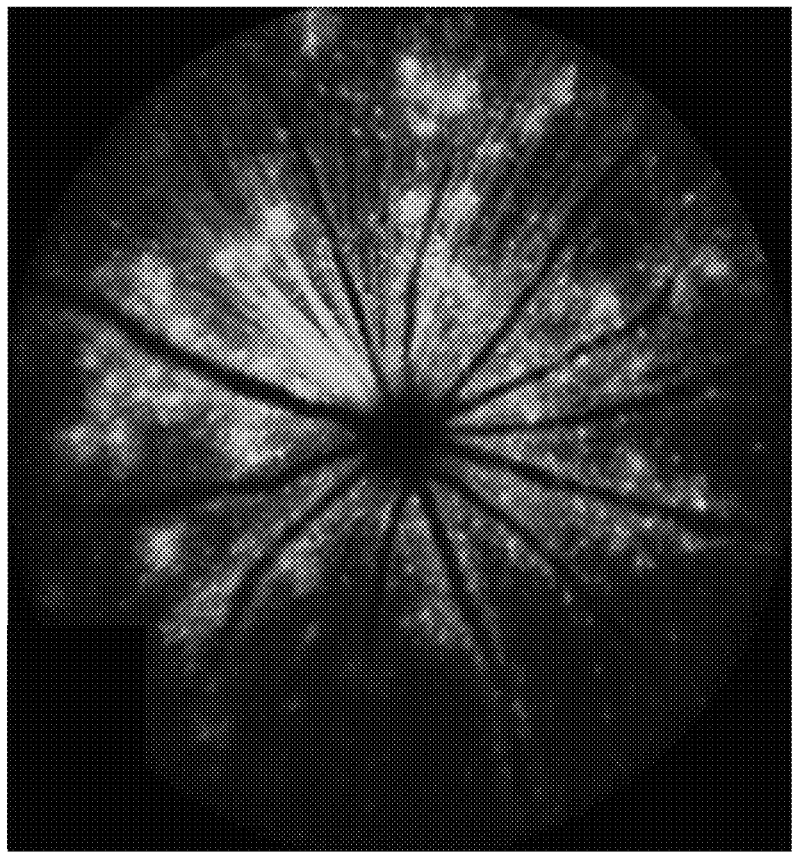
FIG. 6B is fluorescent imaging of GFP two hours post-gavage @ 10 mg/kg of theophylline (activating ligand).
Figure 6A:
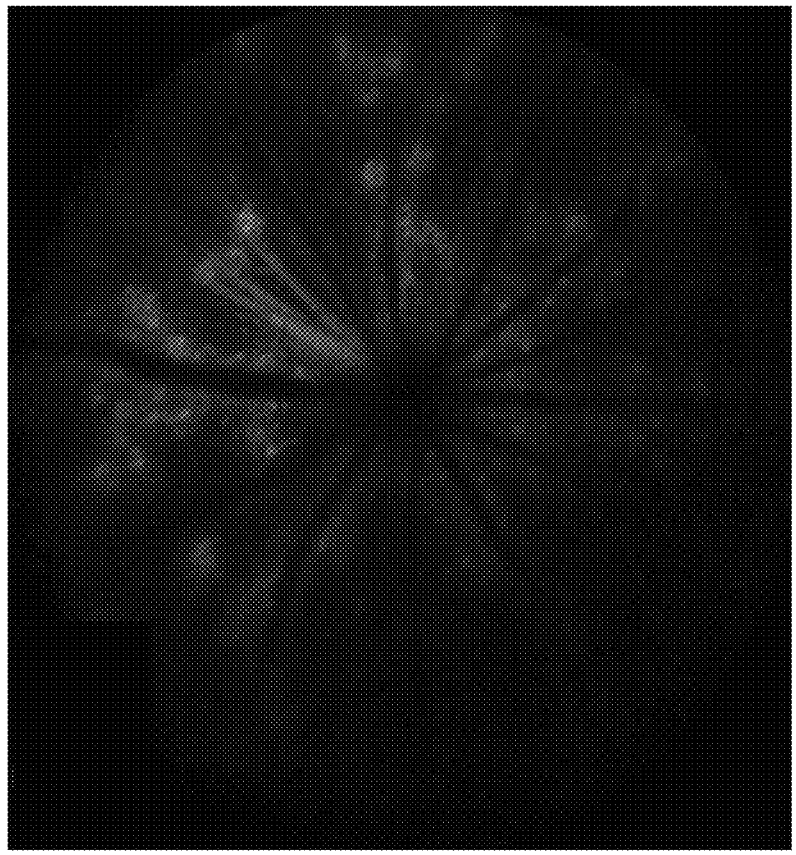
FIG. 6A is fluorescent imaging depicting GFP expression in the retina of a 10 mouse 4 weeks post infection. C57BL6/J mouse injected intravitreally with $1.0 \times 10^{10}$ vector genomes (vg) of rAAV2.smCBA-hGFP-3×-L2Bulge9.
Figure 7:
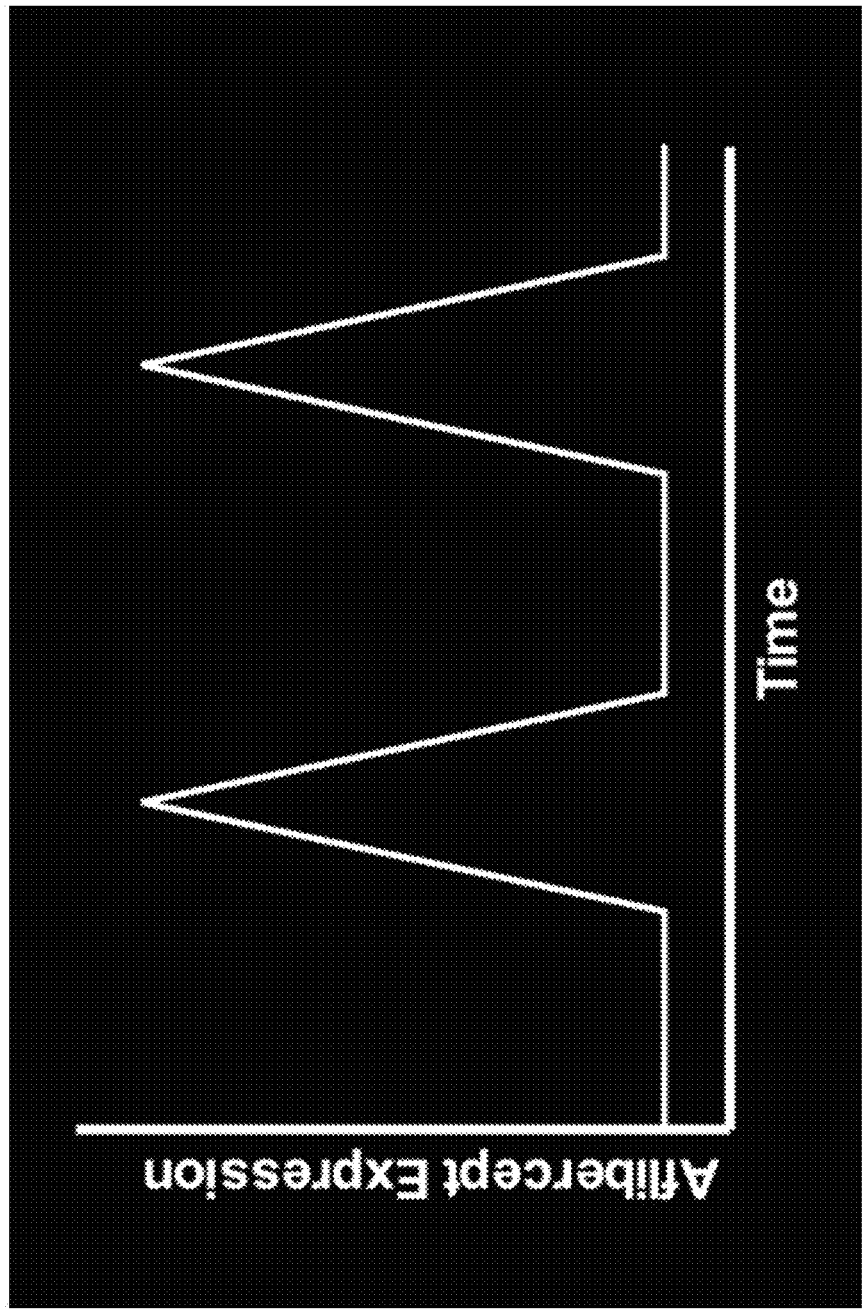
FIG. 7 is proposed response of using a SLIM switch (constitutively off transgene), showing monthly administration of ligand results in a spike in expression level of the transgene (e.g. aflibercept).

In vivo results demonstrated dosing mice with the activating ligand of each riboswitch could achieve a highly significant change in GFP fluorescence at 2 hours post-gavage compared to pre-treatment levels ($p<0.01$, paired t test, N=6) (FIGS. 6A and 6B). Importantly, GFP fluorescence was recovered to pre-treatment levels 24 hours after receiving the activating ligand. This shows that genes can be delivered and expressed in the retina of the eye.

Example 2: Evaluation of Optimal Copy Number of Riboswitches and Dynamic Range

Example 2A: Testing of Known Riboswitches

Figure 8A:
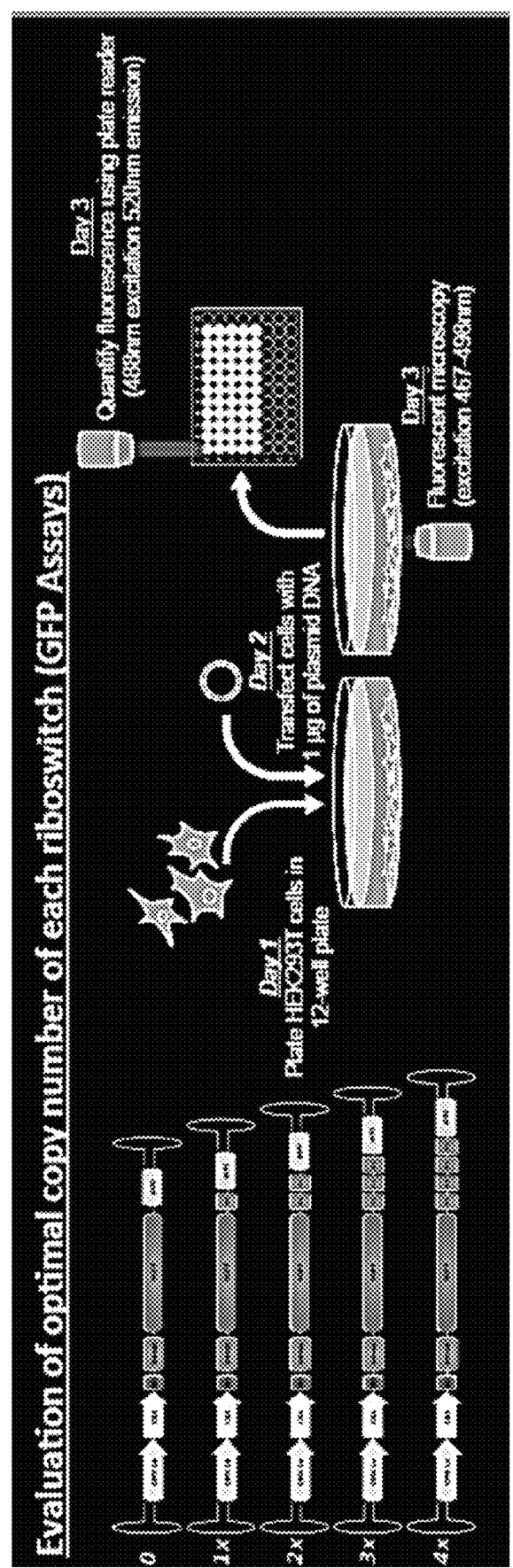
FIG. 8A is a schematic of the testing protocol for determining the optimal copy number of each riboswitch.
Figure 8B:
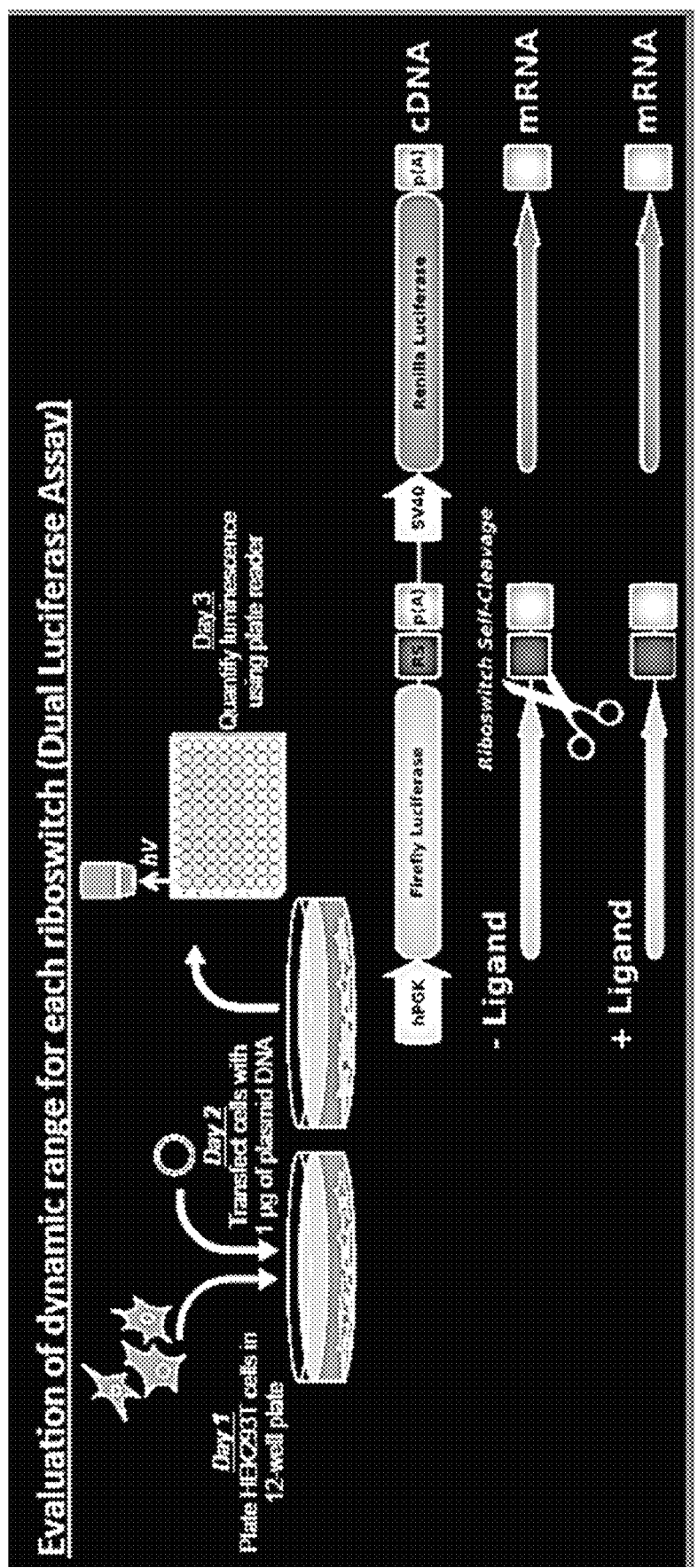
FIG. 8B is a schematic of the testing protocol for evaluation of dynamic range for each riboswitch.

This Example demonstrates the optimal number of riboswitches that can be used in a construct and the related dynamic ranges. The protocol for both assays are outlined in FIGS. 8A and 8B. For determining optimal copy numbers, plasmids containing 0-4 copies of each riboswitch were created with the transgene as green fluorescence protein (GFP) for readout. HEK293T cells were plated in a 12-well plate and on day 2 transfected with 1 µg of each plasmid DNA. On day 3, cells were observed by fluorescent microscopy (excitation 467-498 nm) and fluorescence was quantified using a plate reader (488 nm excitation 520 nm emission).

For determining dynamic range, constructs containing firefly luciferase containing the optimal copy number of the riboswitch were made. HEK293T cells were plated on day 1, and transfected on day 2 with 1 µg of plasmid DNA. Cells were treated with 0-100 µM of the ligand corresponding to the riboswitch and the luminescence was quantified on day 3 using plate reader. Results are shown in Table 2.

Figure 9A:
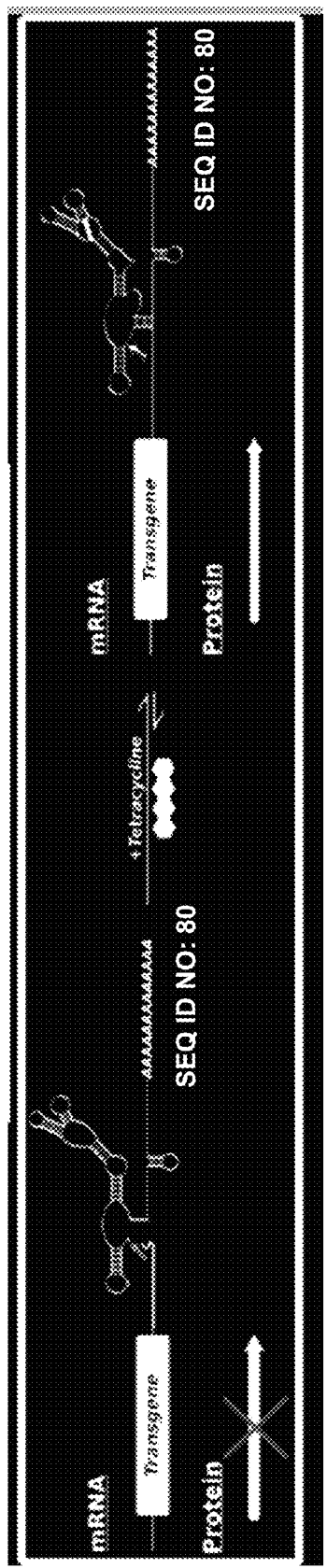
FIG. 9A is a schematic representation of the mRNA of a L2Bulge18tc riboswitch construct.
Figure 9B:
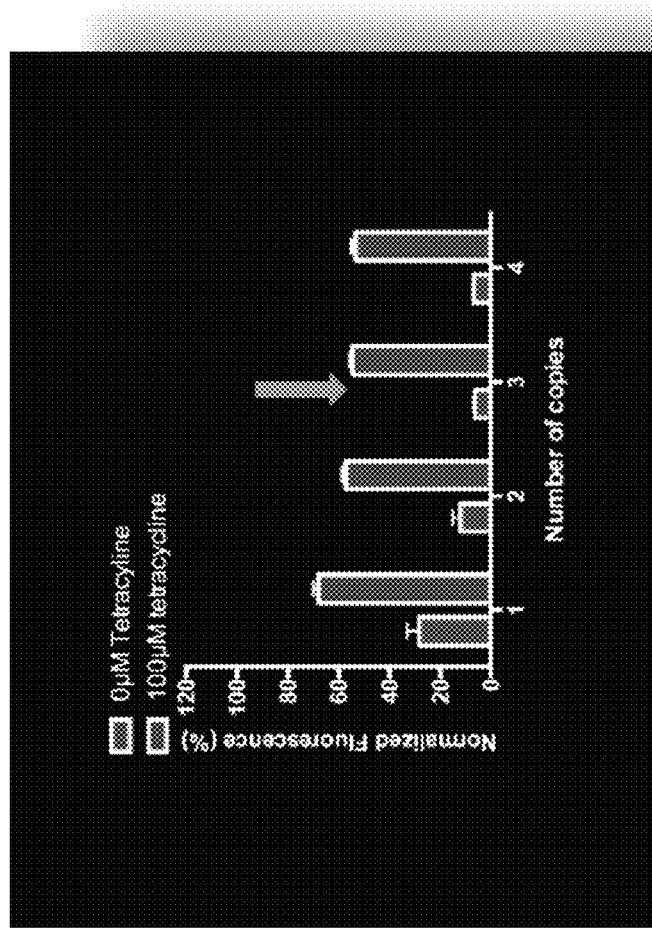
FIG. 9B is a bar graph depicting the results of different copy numbers of the L2Bulge18tc riboswitch on expression levels of a transgene (GFP).
Figure 9C:
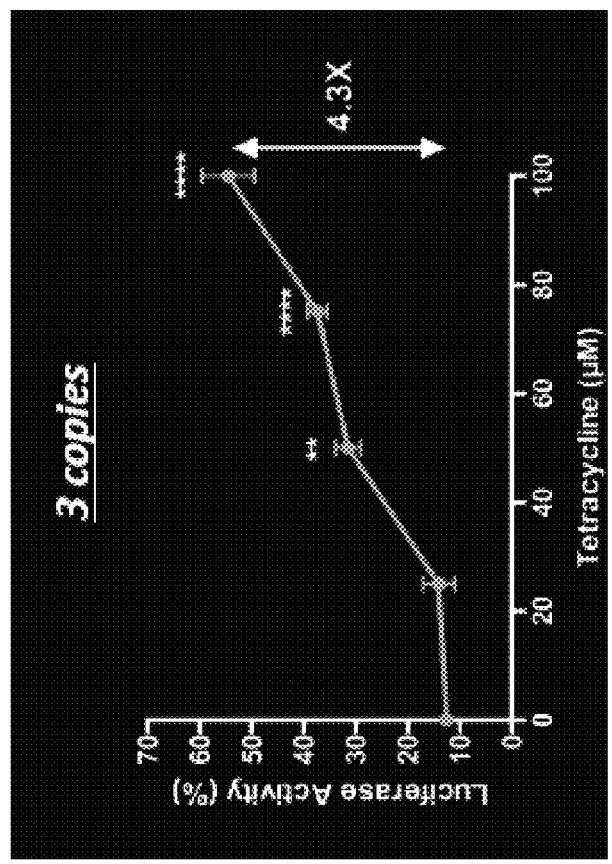
FIG. 9C is a line graph depicting the dynamic range of a construct comprising 3 copies of the L2Bulge18tc riboswitch.
Figure 9D:
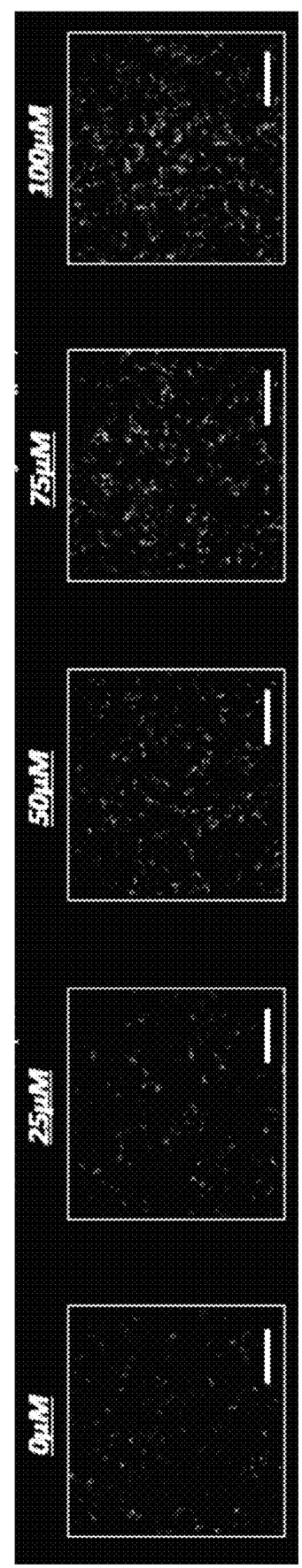
FIG. 9D are fluorescent imaging of cells treated with 0-100 μM tetracycline.
Figure 10A:
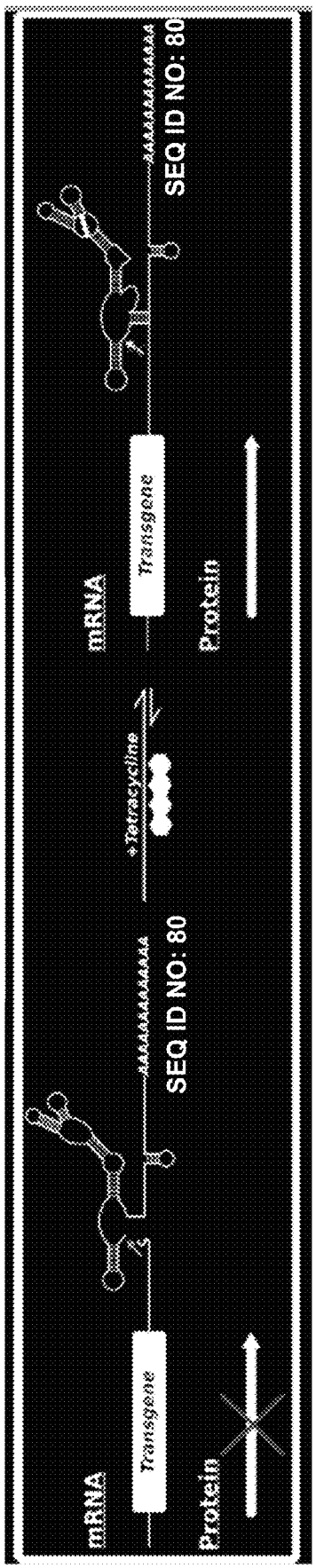
FIG. 10A a schematic representation of the mRNA of a construct containing a K19 riboswitch.
Figure 10B:
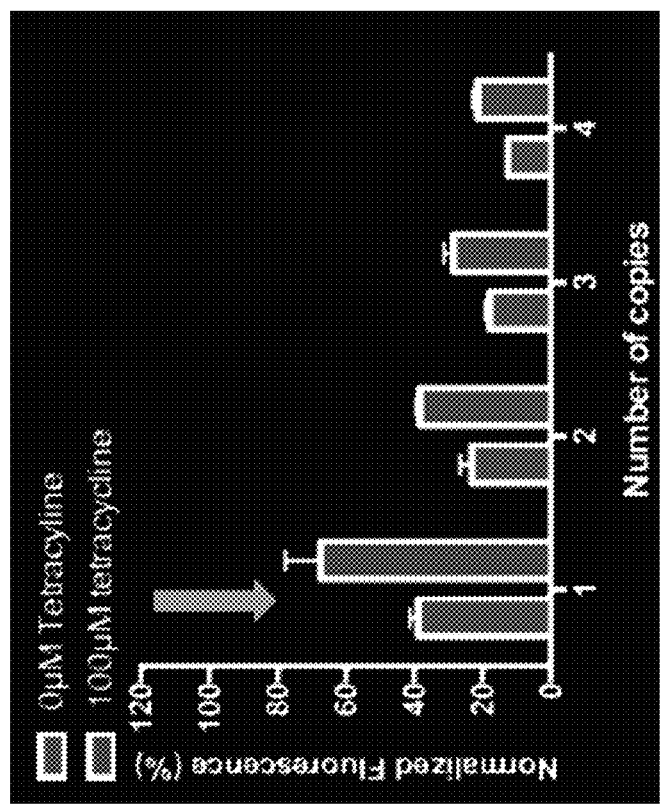
FIG. 10B is a bar graph depicting the results of different copy numbers of the K19 riboswitch on transgene expression levels.
Figure 10C:
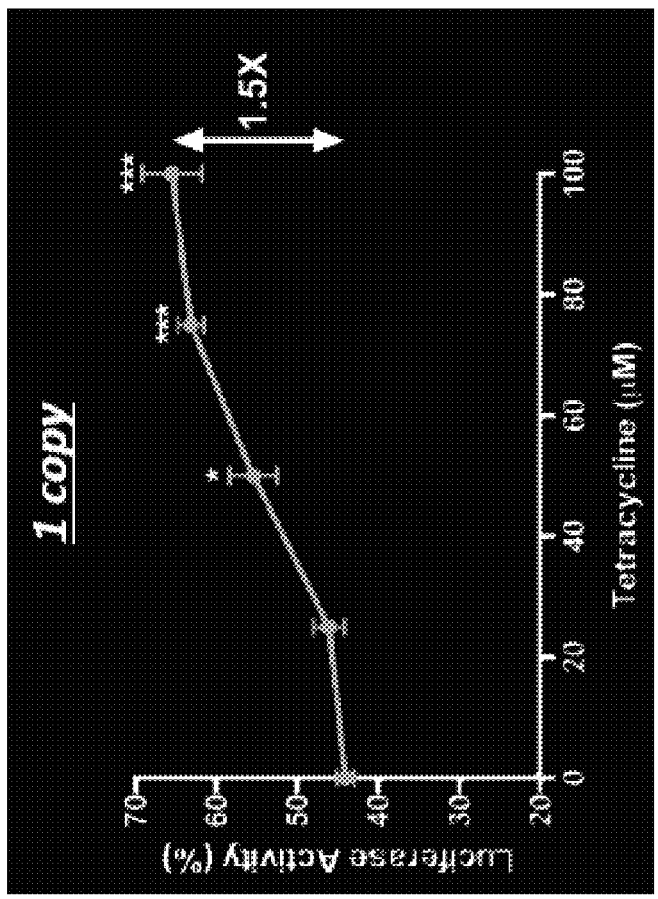
FIG. 10C is a line graph depicting the dynamic range of the optimal copy number of K19 riboswitch.
Figure 10D:
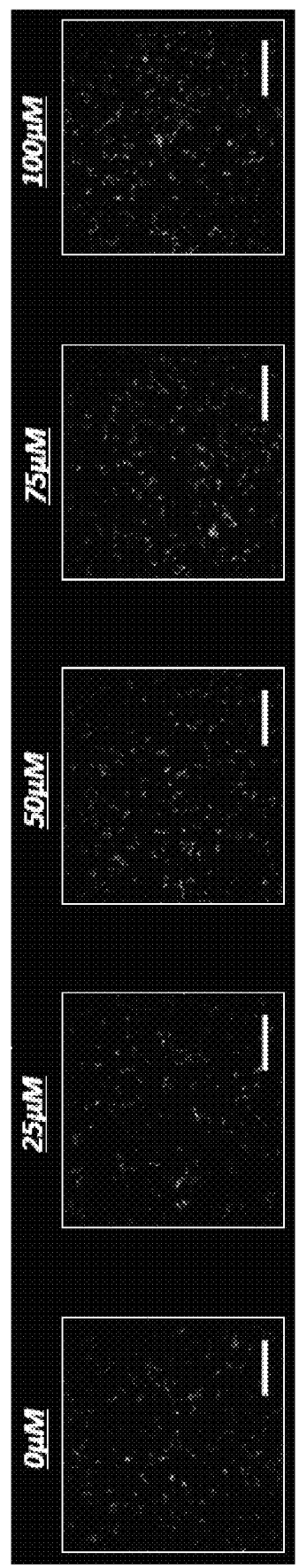
FIG. 10D are fluorescent imaging of cells treated with 0-100 μM of tetracycline which were transduced with the K19 riboswitch construct of 10A.
Figure 11A:
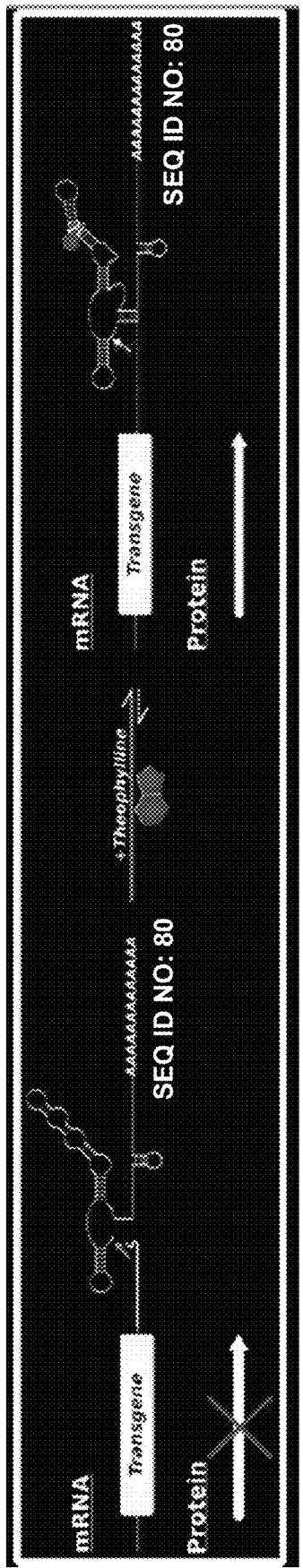
FIG. 11A depicts the mRNA of a construct comprising the L2Bulge9 riboswitch.
Figure 11B:
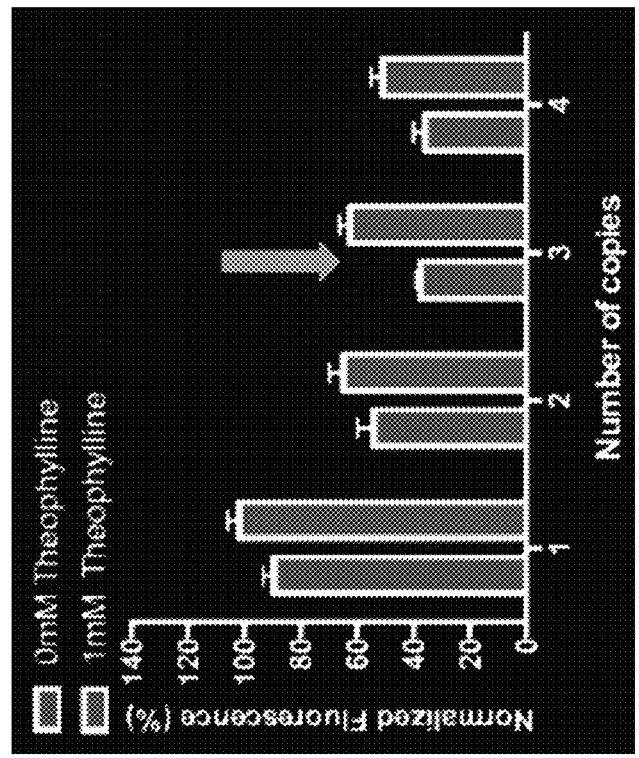
FIG. 11B is a bar graph depicting the results of different copy numbers of the L2Bulge9 riboswitch on transgene expression levels.
Figure 11C:
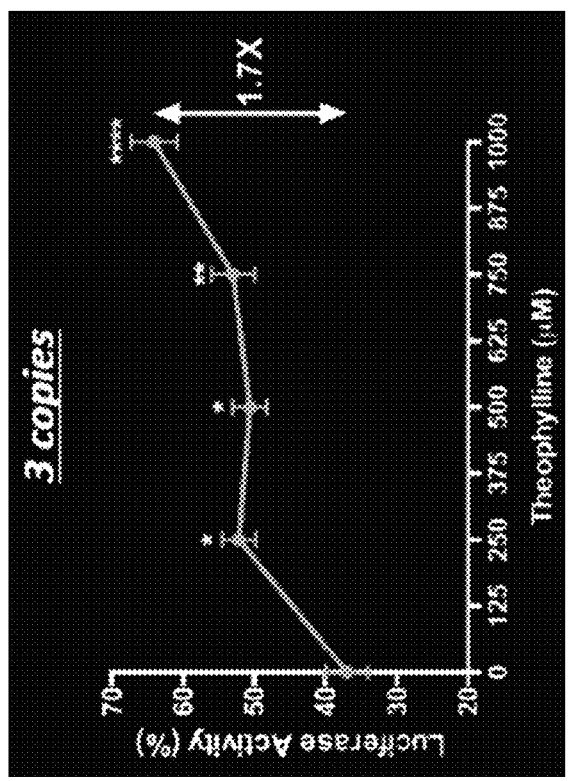
FIG. 11C is a line graph depicting the dynamic range of the optimal copy number of L2Bulge9 riboswitch.
Figure 11D:
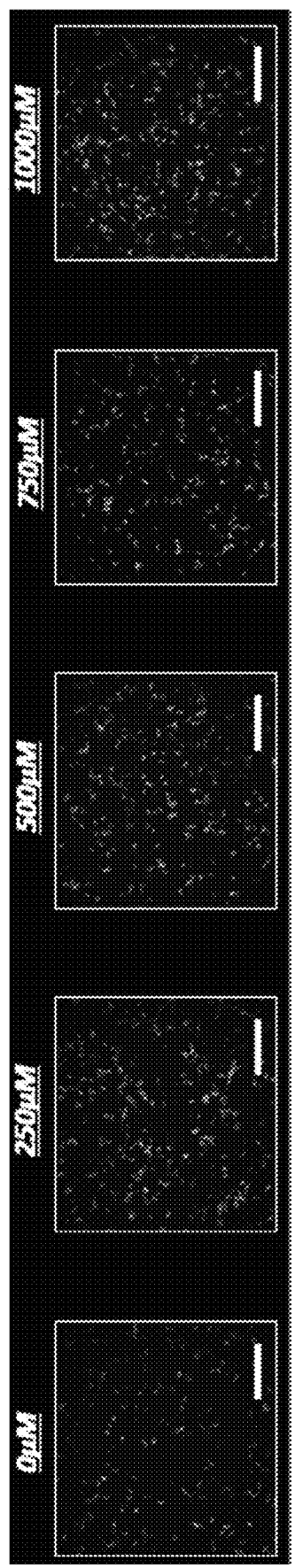
FIG. 11D are fluorescent imaging of cells treated with 0-100 μM of theophylline which were transduced with the L2Bulge9 riboswitch construct of 11A.

As depicted in FIG. 9A, L2Bulge18tc riboswitch was one ON-type riboswitch tested. The cells were treated with 0 µM, 25 µM, 50 µM, 75 µM, and 100 µM of tetracycline (ligand), with the fluorescent microscopy results shown in FIG. 9D. Fluorescence was quantified and results are demonstrated in FIG. 9B, demonstrating 3 copies provides optimal dynamic range, as depicted in FIG. 9C.

K19 riboswitch was also tested (FIG. 10) as described above, and the results are shown in FIG. 9B-D, demonstrating that 1 copy is the optimal copy number.

L2Bulge 9 was also tested (using activating ligand Theophylline), and the optimal copy number was determined to be 3.

Results for a number of ON-type riboswitches are summarized in Table 1 above.

Example 2B: Testing of New SLIM Switches

Figure 12A:
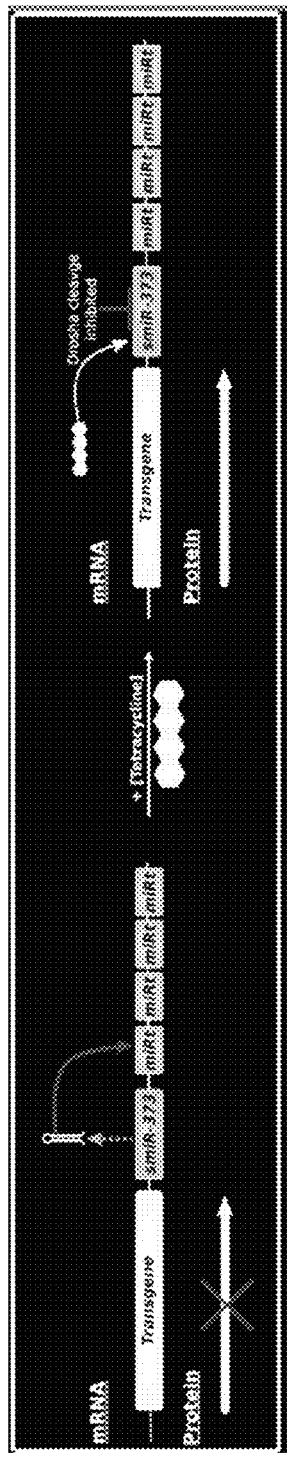
FIG. 12A depicts the mRNA of a construct comprising the tetracycline SLIM switch (ON-type switch).
Figure 12B:
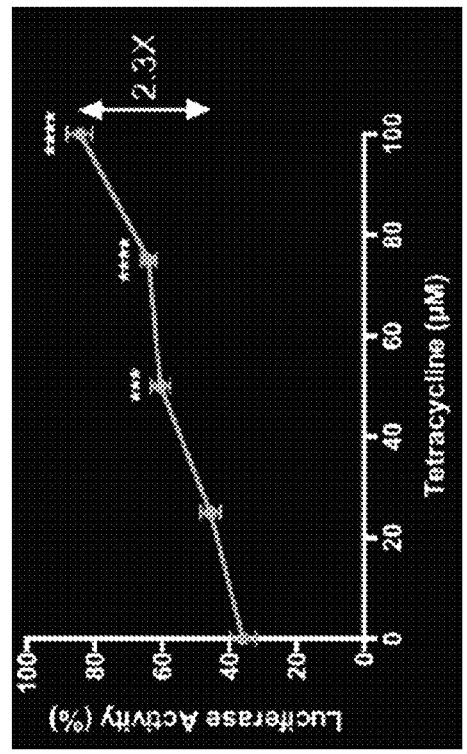
FIG. 12B depicts the dynamic range of the tet-SLIM switch of FIG. 12A.
Figure 12C:
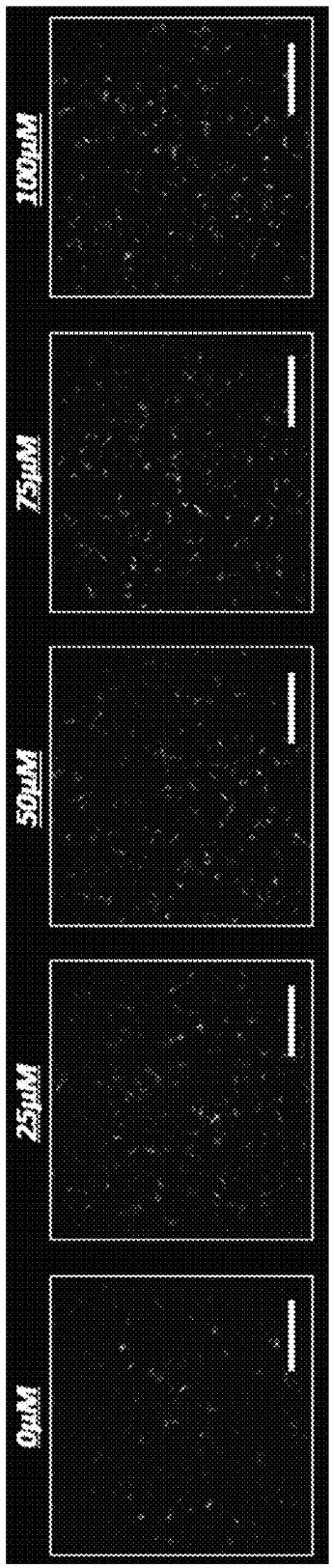
FIG. 12C are fluorescent imaging of cells treated with 0-100 μM of tetracycline which were transduced with the tet-SLIM switch construct of 12A.
Figure 13A:
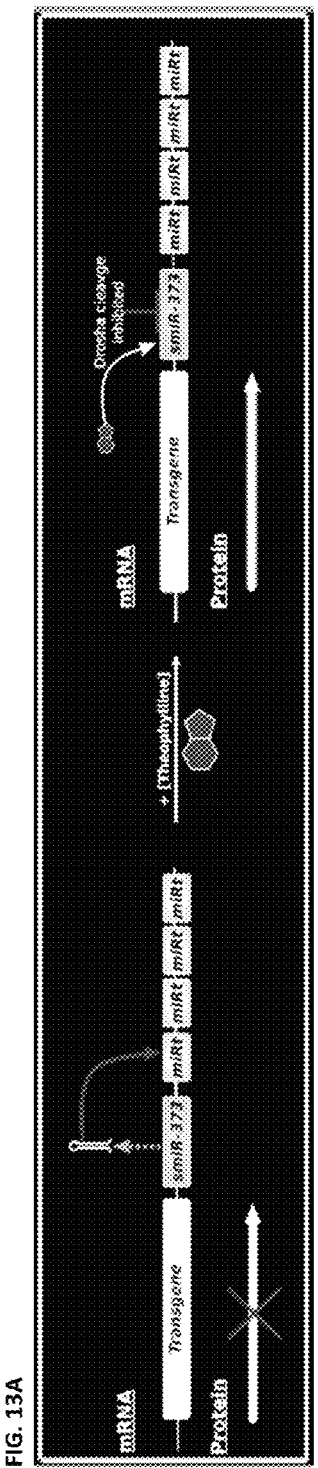
FIG. 13A depicts the mRNA of a construct comprising the theophylline SLIM switch (ON-type switch).
Figure 13B:
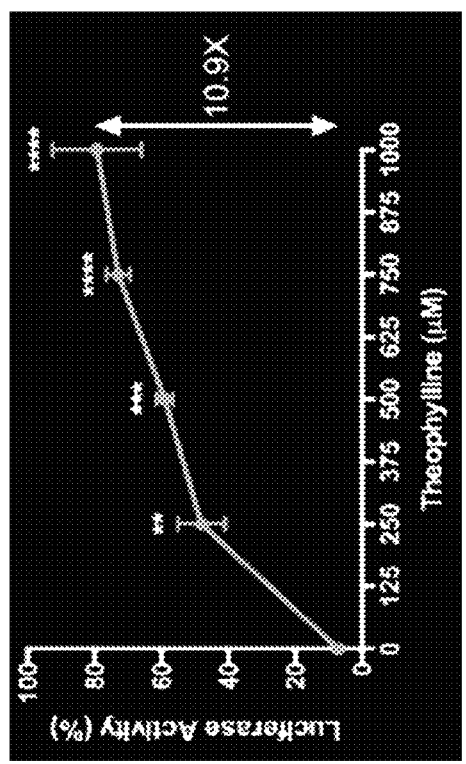
FIG. 13B depicts the dynamic range of the theo-SLIM switch of FIG. 13A.
Figure 13C:
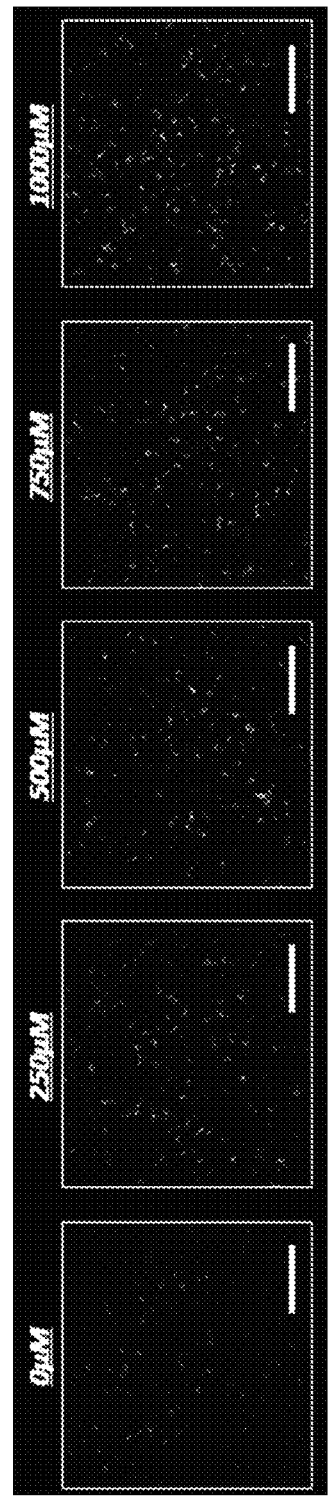
FIG. 13C are fluorescent imaging of cells treated with 0-100 μM of theophylline which were transduced with the theo-SLIM switch construct of 13A.

Experiments as described in Example 2A were also carried out using the newly designed Tet-SLIM and Theo-SLIM switches including target miRNA sequence, as depicted in FIGS. 12A and 13A, respectively. FIGS. 12B and 13B show the dynamic range for both switches, while FIGS. 12C and 13C depict fluorescence as seen in the cells treated with 0-100 µM of their respective ligands. Both SLIM riboswitches had an increased dynamic range over similar riboswitches known in the art.

Example 3: Mouse Study Using SLIM Containing Anti-VEGF Compound

Adult (>2 months old) wild-type (e.g. C57Bl/6 j strain) mice (n=20) will be purchased from an approved supplier (e.g. Jackson Laboratories) and group housed at the Medical College of Wisconsin in standard conditions. After a period of acclimatization, each animal will undergo bilateral intravitreal injections. One eye will receive 2 µl sterile buffer (HBSS+0.014% tween-20) containing purified recombinant adeno-associated virus (rAAV) packaging the cDNA sequences required for biosynthesis of a vascular endothelial growth factor (VEGF) inhibitor (e.g. Aflibercept (Eylea)) under control the SLIM gene-switch (named herein, rAAV.SLIM.αVEGF). The contralateral eye will receive an injection of buffer only to control for the effects of the surgical intervention. Four weeks will be allowed for incorporation of the rAAV.SLIM.αVEGF vector into cells of the retina; based on preliminary data we expect ganglion cells and Müller glia be effectively transduced. All eyes will be imaged by fluorescein angiography (FA) using a confocal scanning laser ophthalmoscope to establish the baseline integrity of the retinal and choroidal blood vessels. Animals will subsequently be assigned randomly to either the treatment (receives activating ligand) or control (no activating ligand) group. Acute choroidal neovascularization (CNV) will be induced in all eyes by making a small hole in Bruch's membrane with a focused infrared laser beam. The extent of CNV formation will be assessed seven and 14 days thereafter by FA.

It is anticipated that animals of the control group (no ligand=low-level αVEGF expression) will demonstrate CNV formation in the rAAV. SLIM. αVEGF injected eyes that is similar in extent to the contralateral buffer injected eyes. By contrast, it is anticipated that animals of the experimental group (with ligand=high-level αVEGF expression) will exhibit significantly reduced CNV formation in rAAV.SLIM.αVEGF injected eyes compared to the contralateral buffer injected eyes. This will serve to demonstrate that rAAV-mediated over-expression of a VEGF inhibitor is an effect method for preventing CNV formation, and that the expression levels of the VEGF inhibitor can be modulated (i.e. increased) through supplementation of the activating ligand, leading to a reduction in CNV formation. All animals will subsequently be euthanized to allow collection of the eyes for biochemical analysis, allowing direct quantification of αVEGF protein levels within treated (with ligand) and control (no ligand) eyes.

Example 4: Treatment of AMD Using rAAV.SLIM.αVEGF Vector

Due to the slowly progressing nature of AMD, a therapeutic window exists between initial diagnosis and the onset of severe visual impairment in which to intervene. Following diagnosis, patients would receive a single intravitreal injection of the rAAV.SLIM.αVEGF vector suspended in a physiologically relevant buffer. The current treatment paradigm for AMD patients involves monthly or bimonthly intravitreal injections of anti-VEGF protein; a single-dose administration rAAV.SLIM.αVEGF would therefore represent a significantly less invasive treatment alternative. Intravitreal injections of anti-VEGF protein are currently performed under local anesthesia as an outpatient procedure; it is anticipated that this would also be the case for intravitreal administration of the rAAV.SLIM.αVEGF vector. Four to eight weeks would be allowed for incorporation of the rAAV.SLAM.F2α vector into cells of the inner retina. The patient could continue to receive conventional anti-VEGF therapy during this time. The SLIM technology is an ON-type switch; as such anti-VEGF protein will not be expressed in the patient's eye until the activating ligand is provided. Anti-VEGF protein expression levels in the patient eye will be regulated through oral administration of the activating ligand (e.g. in tablet form). The SLIM technology is dose-dependent, allowing the patient/physician to precisely modulate anti-VEGF expression levels within the eye. The retinal cells targeted as part of this procedure do not divide. As a consequence, following incorporation of the vector into those cells, it is anticipated that the rAAV.SLIM.αVEGF vector will persist throughout the patient's lifetime. Anti-VEGF expression can therefore be induced at any time throughout the patient's lifetime by administration of the activating ligand, negating the need for repetitive intra-ocular injections.

Example 5: AAV-Riboswitch for Treating AMD

Current treatment methodologies for treating AMD focus on the administration soluble receptors or neutralizing antibodies raised against VEGF-A protein in order to inhibit its pro-angiogenic function. Eylea (aflibercept), a recombinant fusion VEGF trap licensed by the Food and Drug Administration for the treatment of wet AMD in 2011, has been found to be highly effective at treating CNV in patients with wet AMD. Although this approach has been largely successful at preventing CNV formation, it requires a monthly high-dose intravitreal injection of anti-VEGF agents throughout a patient's lifetime, resulting in a substantial financial and economic burden. Moreover, continuous bolus administration of both Eylea and Lucentis over multiple years has been shown to accelerate the rate of retinal and choroidal atrophy. Patients are also at an increased risk for injection related complications such as endophthalmitis and cataract formation. In this Example, we combine several technologies developed within our laboratory to create an inducible rAAV-based gene therapy approach to treat wet AMD following a single intravitreal administration.

We assessed whether rAAV-mediated over-expression of Eylea is capable of preventing CNV formation following laser injury to Bruch's membrane. By incorporating a tetracycline-responsive riboswitch (1×TC45) riboswitch in the 3'-UTR of the expression cassette, we were also able to address whether modulating the intraocular concentration of Eylea led to an alteration in the severity of CNV lesions observed. To this end, age-matched C57BL/6J mice were unilaterally injected with either PBS (n=10), $1.0 \times 10^{10}$ vg of rAAV2/2[MAX].smCBA-Eylea (n=10) or $1.0 \times 10^{10}$ vg rAAV2/2[MAX].smCBA-Eylea-1×-TC45 (n=20). Immediately following injections, half of the mice (n=10) injected with rAAV2/2[MAX].smCBA-Eylea-1×-TC45 were placed on diet containing 50 mg/g tetracycline. Six weeks post-injection, CNV formation was initiated by rupturing Bruch's membrane using an infrared laser diode (see methods). Seven days following laser injury, neovascular lesion size and leakage was assessed via fluorescein angiography using cSLO imaging. The majority of mice ubiquitously expressing Eylea (smCBA-Eylea) either did not develop lesions at the site of laser injury, or developed small grade 1 or 2A type lesions that leaked minimal fluorescein, even after a 5-minute period. (FIG. 14A-C). Mice injected with the 'OFF-type' smCBA-Eylea-1×-TC45 vector and placed on regular diet also predominantly developed only minor lesions, though a small increase in the number of 2B lesions were observed compared to the non-inducible Eylea construct (FIG. 14D-F). Lowering Eylea expression through activation of the TC45 riboswitch greatly increased the severity of CNV lesions (FIG. 14G-I) to the extent that they were similar in extent to PBS-sham injected mice (FIG. 14L-J).

Lesion images were graded by three blinded scientists using the grading system described by Krzystolik et al. (see methods for details). Importantly, grade distribution was significantly different for each treatment group Mice receiving a sham injection had the highest incidence of clinically significant 'Grade 2B' lesions, while mice ubiquitously over-expressing Eylea (smCBA-Eylea) had the lowest incidence of 'Grade 2B' lesions.

Figures 15A, 15B:
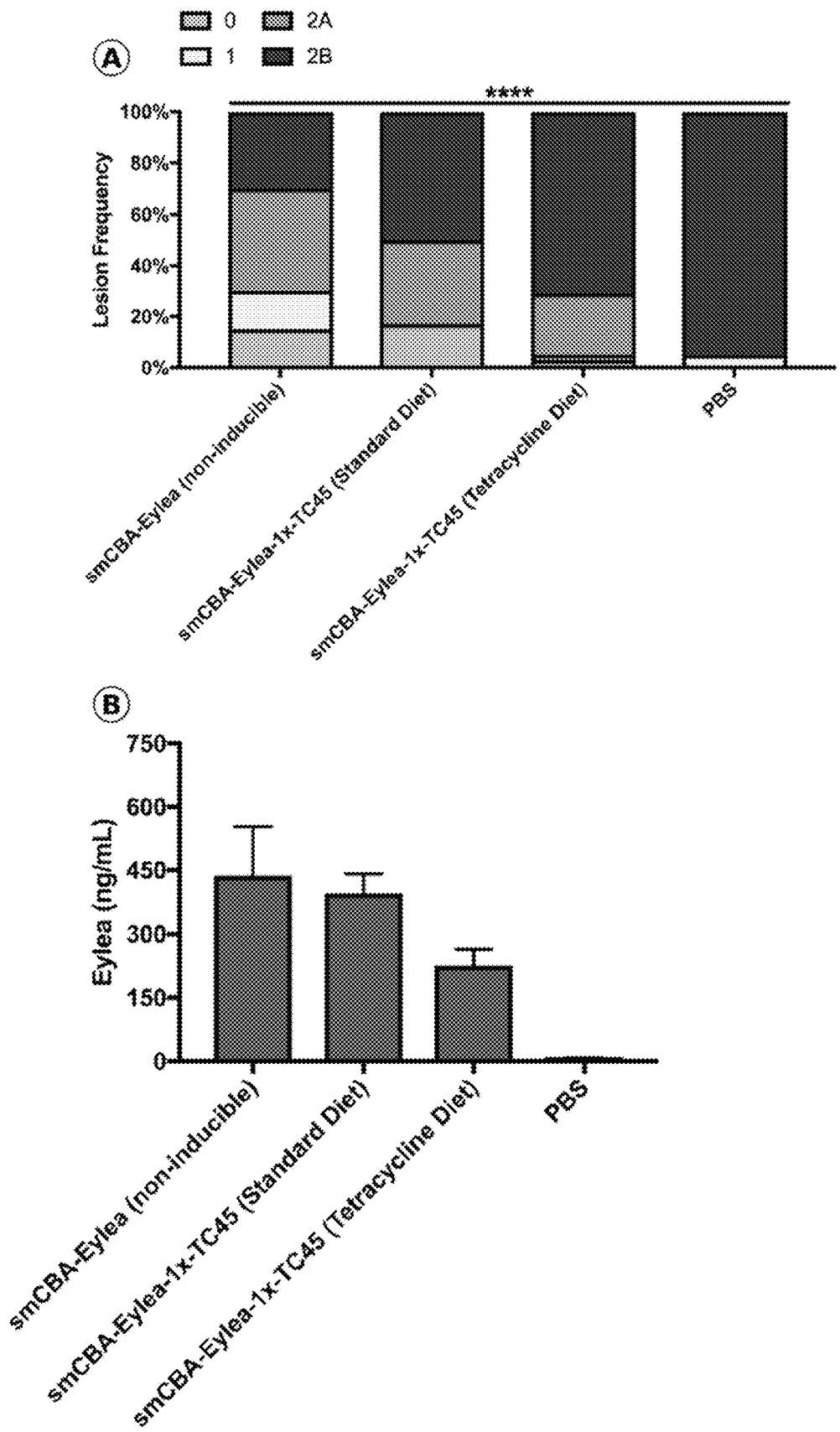
FIGS. 15A-15B demonstrate intraocular concentration of Eylea correlated strongly with severity of CNV lesions. (A) Distribution of lesions graded independently by three blinded scientists. N=16-20 lesions per group, p<0.0001, Chi-squared test). (B) Intraocular levels of non-complexed Eylea assayed by ELISA. N=5 eyes per group.
Figure 17A:
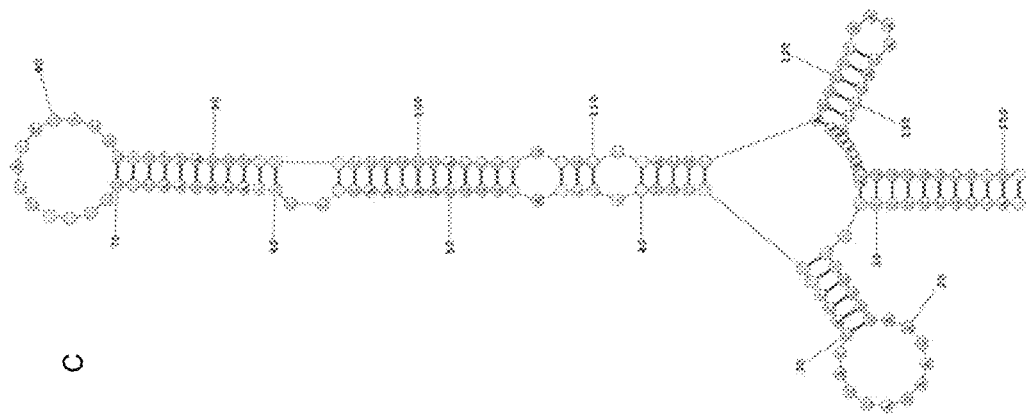
FIGS. 17A-17C are schematic representations of 6S-folini acid-responsive SLIM (A) (SEQ ID NO:21), theophylline-responsive SLIM (B) (SEQ ID NO:26) and tetracycline-responsive SLIM (C) (SEQ ID NO:31).
Figure 17B:
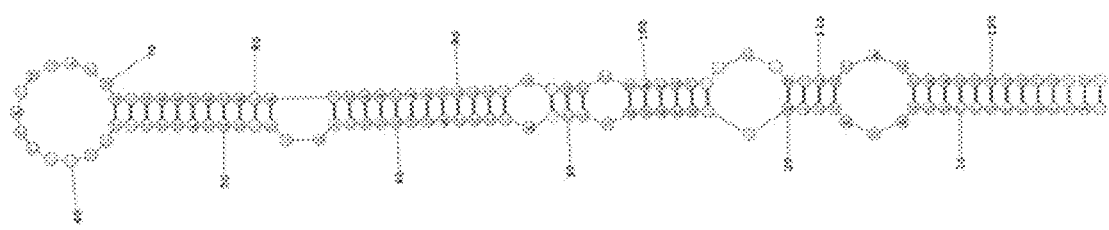
Figure 17C:
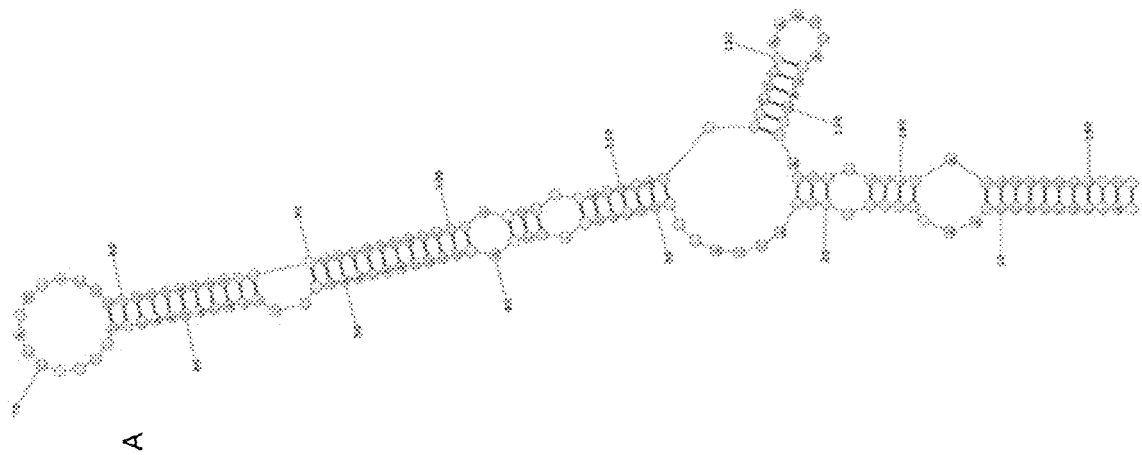
Figure 20:
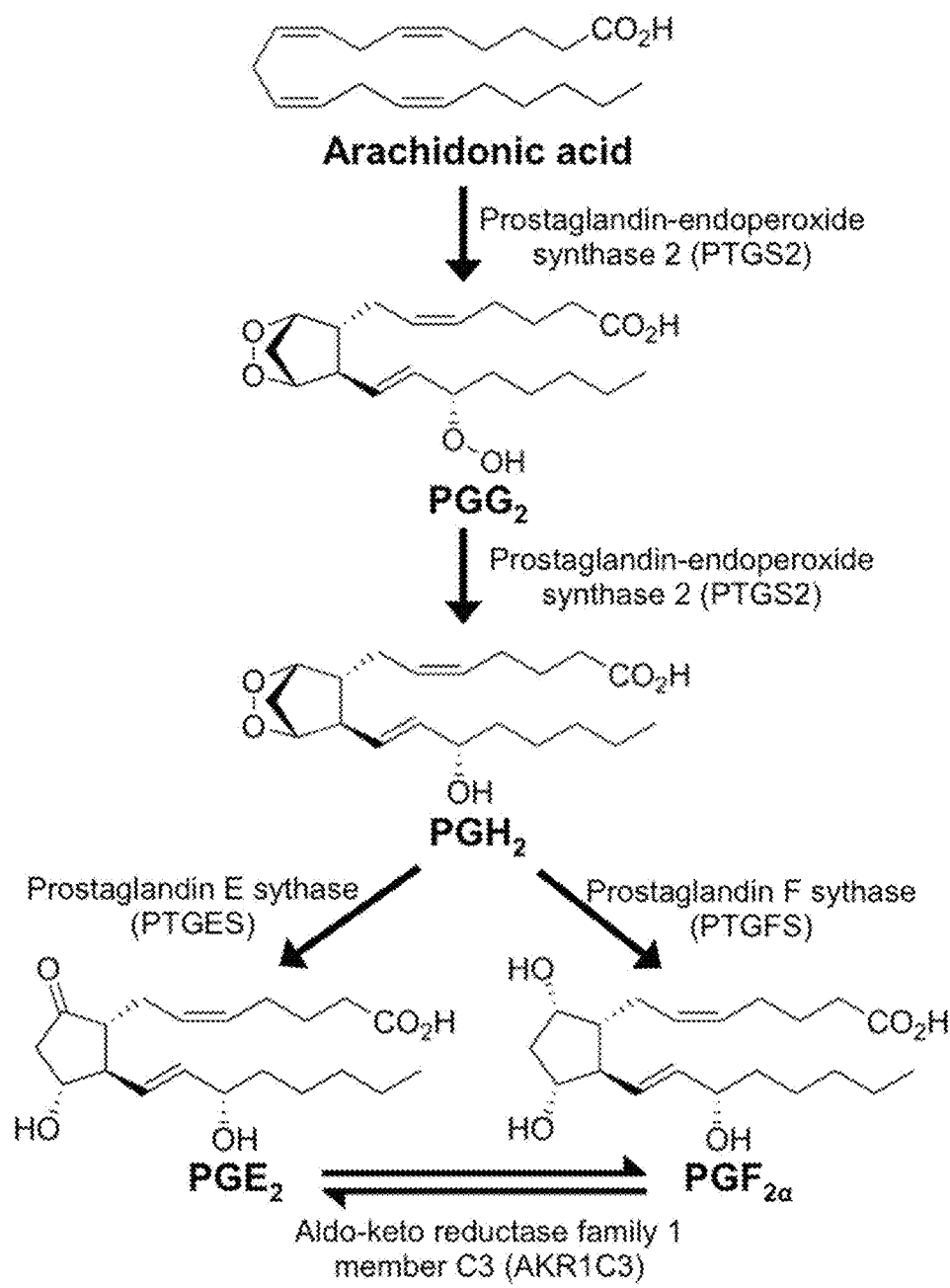
FIG. 20 demonstrates the enzymes of the PGF2α biosynthesis pathway.

Notably, downregulating Eylea expression through activation of the TC45 riboswitch resulted in a considerable increase in the incidence of 'Grade 2B' lesions compared to rAAV2[MAX].smCBA-Eylea-1×-TC45 injected mice receiving standard diet (FIG. 15A). Finally, we determined the levels of non-complexed Eylea in each sample using an Eylea-specific ELISA (Eagle Biosciences). As expected, eyes injected with the non-inducible construct (smCBA-Eylea) contained the highest levels of free Eylea (438 ng/mL). Moreover, high levels of free Eylea were detected in animals injected with vector containing the tunable construct (395 ng/mL), though levels were lower than animals injected with the non-inducible construct. Importantly, tetracycline-mediated activation of the TC45 riboswitch resulted in a significant 1.75-fold decrease in non-complexed Eylea ($p<0.05$). (FIG. 15B) The levels of free Eylea correlated strongly with the occurrence of clinically significant lesions.

Example 6: Self-Targeting Ligand Inactivating miRNAs for AMD Treatment in Humans A SLIM switch requires the basal region of a pri-miRNA to be replaced with an aptamer. This sequence is cloned into either the 3'- or 5' untranslated region of an expression cassette. Additionally, miRNA target sites that are complementary to the sequence of the mature miRNA can be included in one or multiple copies at either the 5' or 3' untranslated region of the cassette.

Self-targeting Ligand Inactivated miRNAs (SLIM) switches function by regulating gene expression at the post-transcriptional level. In conditions when the activating ligand is absent, the pri-miRNA will be cleaved by drosha from the nascent transcript. This miRNA will be processed and act as the second mechanism of gene silencing, through binding of the complementary target sites. When the activating ligand is provided, gene expression is unaltered.

Multiple copies of each riboswitch (SLIM) can be included into the 3'-untranslated region of the gene of interest. Each riboswitch appears to have an optimal number of copies as shown in Table 2. Furthermore, multiple copies of miRNA target sites can be included in the 3' or 5' untranslated region.

Due to the slowly progressing nature of AMD, a therapeutic window exists between initial diagnosis and the onset of severe visual impairment in which to intervene. Following diagnosis, patients would receive a single intravitreal injection of the rAAV.SLIM.αVEGF vector suspended in a physiologically relevant buffer. The current treatment paradigm for AMD patients involves monthly or bimonthly intravitreal injections of anti-VEGF protein. Thus, a single-dose administration rAAV.SLIM.αVEGF would therefore represent a significantly less invasive treatment alternative. Intravitreal injections of anti-VEGF protein are currently performed under local anaesthesia as an outpatient procedure; it is anticipated that this would also be the case for intravitreal administration of the rAAV.SLIM.αVEGF vector. The patient could continue to receive conventional anti-VEGF therapy during this time. The SLIM technology is an ON-type switch; as such anti-VEGF protein will not be expressed in the patient's eye until the activating ligand is provided. Anti-VEGF protein expression levels in the patient eye will be regulated through oral administration of the activating ligand (e.g. in tablet form). The SLIM technology is dose-dependent, allowing the patient/physician to precisely modulate anti-VEGF expression levels within the eye. The retinal cells targeted as part of this procedure do not divide. As a consequence, following incorporation of the vector into those cells, it is anticipated that the rAAV.SLIM.αVEGF vector will persist throughout the patient's lifetime. Anti-VEGF expression can therefore be induced at any time throughout the patient's lifetime by administration of the activating ligand, negating the need for repetitive intra-ocular injections.

Treating Glaucoma with Vectors Comprising Riboswitches

Primary open angle glaucoma (POAG) is the second leading cause of irreversible blindness worldwide and is characterized by progressive loss of retinal ganglion cells and atrophy of the optic nerve, leading to visual field deficits. The major risk factor for POAG is increased intraocular pressure (IOP) resulting from decreased aqueous humor outflow. The gold standard clinical therapy for glaucoma is to reduce TOP through a combination of topical drug administration, and in late-stage disease, surgery. Unfortunately, due to the largely asymptomatic (i.e. non-painful) nature of glaucoma and the necessity to maintain a lifelong daily treatment regimen, patient compliance with drug therapies is extremely poor (<20%), leading to the development of severe sight-threatening complications, even in patients diagnosed early.

AAV-Riboswitch Experiments—A Model for Treating Glaucoma

Prostaglandin analogs (e.g. Latanprost) are administered clinically as esterified pro-drugs that are absorbed across the corneal epithelium and are hydrolyzed into their active form as they pass through the stroma and corneal endothelium before diffusing into the aqueous humor. Binding of soluble $PGF_{2\alpha}$ analog to PTGFR triggers up-regulation of matrix metaloprotinase (MMP) production within the ciliary muscle that promotes remodelling of the extracellular matrix and increased uveosderal aqueous outflow. Native $PGF_{2\alpha}$ is enzymatically derived from aracadonic acid, which is present in the cornea at high levels, via a multistep process.

De novo biosynthesis and secretion of $PGF_{2\alpha}$ from the cornea into the anterior chamber promises to be an effective strategy for lowering IOP that improves upon the current gold-standard clinical treatment approach. We have demonstrated that over-expression of prostaglandin endoperoxide synthase 2 (PTGS2), the rate limiting enzyme in $PGF_{2\alpha}$ biosynthesis, and PTGFR, causes a significant decrease in IOP over a period of three months. THe cDNA sequences (below) for both enzymes were incorporated into a AAV expression construct (complete sequence below) incorporating either no riboswitch (non-inducible) or with a 3' TC40 and 5' TC45 tetracycline inducible riboswitch. Mice received intracamereal injections of PBS (N=10), rAAVsniCBA-PTGFR.P2A.PTGFR (N=10, non-inducible) or rAAV.smCBA-TC40-PTGER.P2A.PTGFR-TC45 (inducible). TOP was measured by rebound tonometry before and 12 weeks following injection. Half of the inducible mice were placed on tetracycline containing diet for that period. Mice placed on diet (PGF2alpha Expression OFF) showed no decreased in intraocular pressure over the 12 week period. Mice on normal diet (PGF2alpha expression ON) showed a highly significant decrease in IOP, similar to when PGF2alpha is constitutively expressed (no switch).

Sequence Listing Statement

The application includes the sequence listing through-out the specification and in the attached sequence listing. The content of the ASCII text file of the sequence listing named "650053_00630_ST25.txt" which is 60,547 bytes in size was created on Jan. 27, 2023, and electronically submitted via EFS-Web and is incorporated herein by reference in its entirety. A few sequences are listed below, but are not to be considered a full listing.

```
L2bulge9 (Theophylline OFF switch)
                                       (SEQ ID NO: 11)
CTCGAGGCGATCGCAAACAAACAAAGCTGTCACCGGATGTGCTTTCCG

GTCTGATGAGTCCGTTGTCCAATACCAGCATCGTCTTGATGCCCTTGG

CAGTGGATGGGACGGAGGACGAAACAGCAAAAGAAAAATAAAAATT

TTTTTTTTAATTAATCTTGGGCCC

L2bulgel8tc (Tetracycline ON switch)
                                       (SEQ ID NO: 12)
CTCGAGGCGATCGCAAACAAACAAAGCTGTCACCGGATGTGCTTTCCG

GTCTGATGAGTCCGTTGTCCAAAACATACCAGATTTCGATCTGGAGAG

GTGAAGAATTCGACCACCTGGACGAGGACGGAGGACGAAACAGCAAAA

AGAAAAATAAAAATTAATTAATCTTGGGCCC

Theo6HDV (Theophylline OFF switch)
                                       (SEQ ID NO: 13)
ATGGCCGGCATGGTCCCAGCCTCCTCGCTGGCGCCGGCTGGGCAACCA

CATACCAGCCGAAAGGCCCTTGGCAGGTGGGCGAATGGGACGCACAAA

TCTCTCTAGCTTCCCAGAGAGAAGCGAGAGAAAAGTGGCTCTC

GuaM8HDV (Guanine OFF switch)
                                       (SEQ ID NO: 14)
ATGGCCGGCATGGTCCCAGCCTCCTCGCTGGCGCCGGCTGGGCAATGC

TATAATCGCGTGGATATGGCACGCAAGTTTCTACCGGGCACCGTAAAT

GTCCGACTAGTAGCGAATGGGACGCACAAATCTCTCTAG

K19 (Tetracycline ON switch)
                                       (SEQ ID NO: 15)
CAAACAAACAAAGGCGCGTCCTGGATTCGTGGTAAAACATACCAGATT

TCGATCTGGAGAGGTGAAGAATACGACCACCTGTAGTATCCAGCTGAT

GAGTCCCAAATAGGACGAAACGCGCTAAACAAACAAAC

TC40 (Tetracycline OFF switch)
                                       (SEQ ID NO: 16)
CTGAGGTGCAGGTACATCCAGCTGACGAGTCCCAAATAGGACGAAAGG

GAGAGGTGAAGAATACGACCACCTAGGCTCGAAAGAGCCTAAAACATA

CCTTTCCTGGATTCCACTGCTATCCAC

Tet-SLIM
                                       (SEQ ID NO: 17)
CTAGCACGGGTCCCTAAAACATACCGTGAGCGCGAAAGCGCCCCATT

TTGAGTTAGTGAAGCCACAGATGTAACTCAAAATGGGGCGCTTTCCC

GCCTACGGAGAGGTGAAGAATACGACCACCTAGAAGCTTATTGGTACA

TGATAACACCCCAAAATCGAAGCACTTCAAAAACACCCCAAAATCGAA

GCACTTCAAAAACACCCCAAAATCGAAGCACTTCAAAAACACCCCAAA

ATCGAAGCACTTCAGTCTCAGGCATCGTACGATGTCGACCTGCAGG
```

The invention claimed is:

1. An exogenous nucleic acid construct for regulating expression of a transgene by modulating the mRNA of the transgene, the nucleic acid encoding:

(a) a target gene, (b) at least one smiRNA switch selected from the group consisting of SEQ ID NOs: 1, 21-35, and 37-51, located within the untranslated region of the transgene, wherein the at least one smiRNA switch comprises an aptamer domain capable of binding to a ligand and a pri-miRNA, (c) at least one miRNA target sequence complementary to at least a portion of the pri-miRNA, wherein the at least one smiRNA switch regulates expression of the transgene by both (1) regulation of the cleavage of the mRNA of the transgene, and (2) regulating cleavage of the pri-miRNA from the smiRNA, wherein at least a portion of the cleaved pri-miRNA binds to at least one miRNA target sequence silencing the transgene expression.

2. The construct of claim 1, wherein in the absence of ligand, the pri-miRNA is cleaved from the transcript and binds to the at least one miRNA target sequence, wherein binding of the portion of the pri-mRNA to the at least one miRNA target sequence silences the transgene.

3. The construct of claim 1, wherein binding of the ligand to the aptamer domain alters the conformation of the smiRNA, wherein the conformation change inhibits the ability of the pri-miRNA to be cleaved from the transcript, and wherein the transgene is able to be translated.

4. The construct of claim 1, wherein the smiRNA switch is encoded by the nucleic acid sequence of SEQ ID NO:1.

5. The construct of claim 1, wherein the at least one miRNA target sequence is encoded by the nucleic acid sequence (SEQ ID NO: 10)
GAGAGAATCTTCTTTCTGTCTATAAAA.

6. The construct of claim 1, wherein the construct encodes at least three miRNA target sequences, wherein the at least three miRNA target sequences are encoded by SEQ ID NO: 2.

7. The construct of claim 1, wherein the construct comprises one or more smiRNA switches selected from the group consisting of SEQ ID NOs: 21-35 and 37-51.

8. The construct of claim 1, wherein the smiRNA is located within the 3' UTR and the at least one miRNA target sequence is located in the 5'UTR.

9. The construct of claim 1, wherein the construct comprises at least two miRNA target sequences.

10. The construct of claim 1, wherein the at least one miRNA target sequence complementary to at least a portion of the pri-miRNA of (c) is a portion of the transgene within the construct to which at least a portion of the cleaved pri-miRNA binds.

11. The construct of claim 1, wherein the transgene encodes a VEGF inhibitor.

12. The construct of claim 11, wherein the VEGF inhibitor is aflibercept and encoded by SEQ ID NO: 8.

13. The construct of claim 11, wherein the VEGF inhibitor is sFLT1 encoded by SEQ ID NO:36.

14. The construct of claim 1, wherein the aptamer binds to a ligand that is able to cross the blood retinal barrier.

15. The construct of claim 14, wherein the ligand is selected from the group consisting of tetracycline, theophylline, guanine, galactitol, progesterone, mannitol, estradiol, dopamine, quinidine, urea, digoxin, uracil, verapamil, thiourea, mixiflaxacin, thymine, levofloxin, corticosterone, acetazolamide, testosterone, doxycycline, and combinations thereof.

16. The construct of claim 12, wherein the ligand is selected from the group consisting of tetracycline, theophylline, and guanine.

17. The construct of claim 1, wherein the transgene comprises a gene involved in prostaglandin synthesis.

18. The construct of claim 17, wherein the transgene comprises prostaglandin endoperoxide synthase 2 (PTGS2) encoded by SEQ ID NO:52.

19. The construct of claim 18 further comprising PTGFR encoded by SEQ ID NO:53.

20. The construct of claim 17 further comprising SEQ ID NO:54.

21. The construct of claim 1, wherein the construct is an adeno-associated virus (AAV) vector.

* * * * *

SEQUENCE LISTING

<160> NUMBER OF SEQ ID NOS: 80

<210> SEQ ID NO 1
<211> LENGTH: 215
<212> TYPE: DNA
<213> ORGANISM: Artificial Sequence
<220> FEATURE:
<223> OTHER INFORMATION: synthetic

<400> SEQUENCE: 1
cgtatcagca ggtcccataa gctttcgaca attaacgagt gtgtactcgt tctatcatct      60
cacagttaaa gtcgggagaa taggagccgc acgggtcctg ataccagcgt gagcggagag     120

```
aatcttcttt ctgtctatta gtgaagccac agatgtaata gacagaaaga agattctctc    180
cgcctacgcc cttggcagca ccgtacggtt cgatc                              215
```

<210> SEQ ID NO 2
<211> LENGTH: 121
<212> TYPE: DNA
<213> ORGANISM: Artificial Sequence
<220> FEATURE:
<223> OTHER INFORMATION: synthetic

<400> SEQUENCE: 2

```
ctagcgagag aatcttcttt ctgtctataa aagagagaat cttctttctg tctataaaag    60
agagaatctt ctttctgtct ataaaagaga gaatcttctt tctgtctatg tcgaccctgc   120
a                                                                  121
```

<210> SEQ ID NO 3
<211> LENGTH: 286
<212> TYPE: DNA
<213> ORGANISM: Artificial Sequence
<220> FEATURE:
<223> OTHER INFORMATION: synthetic

<400> SEQUENCE: 3

```
ggttggccac tccctctctg cgcgctcgct cgctcactga ggccgggcga ccaaaggtcg    60
cccgacgccc gggctttgcc cgggcggcct cagtgagcga gcgagcgcgc agagagggag   120
tggccaactc catcactagg ggtacccta gtgatggagt tggccactcc ctctctgcgc    180
gctcgctcgc tcactgaggc cgcccgggca agcccgggc gtcgggcgac ctttggtcgc    240
ccggcctcag tgagcgagcg agcgcgcaga gagggagtgg ccaacc                 286
```

<210> SEQ ID NO 4
<211> LENGTH: 236
<212> TYPE: DNA
<213> ORGANISM: Artificial Sequence
<220> FEATURE:
<223> OTHER INFORMATION: synthetic

<400> SEQUENCE: 4

```
tcgactagag ctcgctgatc agcctcgact gtgccttcta gttgccagcc atctgttgtt    60
tgcccctccc ccgtgccttc cttgaccctg gaaggtgcca ctcccactgt cctttcctaa   120
taaaatgagg aaattgcatc gcattgtctg agtaggtgtc attctattct ggggggtggg   180
gtggggcagg acagcaaggg ggaggattgg gaagacaata gcaggcatgc tgggga       236
```

<210> SEQ ID NO 5
<211> LENGTH: 202
<212> TYPE: DNA
<213> ORGANISM: Artificial Sequence
<220> FEATURE:
<223> OTHER INFORMATION: synthetic

<400> SEQUENCE: 5

```
ggtgagcggg cgggacggcc cttctcctcc gggctgtaat tagcgcttgg tttaatgacg    60
gcttgtttct tttctgtggc tgcgtgaaag ccttgagggg ctccgggagc tagagcctct   120
gctaaccatg ttcatgcctt cttctttttc ctacagctcc tgggcaacgt gctggttatt   180
gtgctgtctc atcatttttgg ca                                          202
```

<210> SEQ ID NO 6
<211> LENGTH: 255

```
<212> TYPE: DNA
<213> ORGANISM: Artificial Sequence
<220> FEATURE:
<223> OTHER INFORMATION: synthetic

<400> SEQUENCE: 6
catggtcgag gtgagcccca cgttctgctt cactctcccc atctcccccc cctcccacc      60 cccaattttg tatttattta tttttaatt attttgtgca gcgatggggg cggggggggg     120
gggggggcgc gcgccaggcg gggcggggcg gggcgagggg cggggcgggg cgaggcggag     180
aggtgcggcg gcagccaatc agagcggcgc gctccgaaag tttcctttta tggcgaggcg     240
gcggcggcgg cggcc                                                     255

<210> SEQ ID NO 7
<211> LENGTH: 255
<212> TYPE: DNA
<213> ORGANISM: Artificial Sequence
<220> FEATURE:
<223> OTHER INFORMATION: synthetic

<400> SEQUENCE: 7
aattcggtac ccctagttat taatagtaat caattacggg gtcattagtt catagcccat      60
atatggagtt ccgcgttaca taacttacgg taaatggccc gcctggctga ccgcccaacg     120 accccgccc attgacgtca ataatgacgt atgttcccat agtaacgcca atagggactt     180
tccattgacg tcaatgggtg gactatttac ggtaaactgc ccacttggca gtacatcaag     240
tgtatcatat gccaa                                                     255

<210> SEQ ID NO 8
<211> LENGTH: 1374
<212> TYPE: DNA
<213> ORGANISM: Artificial Sequence
<220> FEATURE:
<223> OTHER INFORMATION: synthetic

<400> SEQUENCE: 8
atggtatcat attgggacac aggagtcctc ctgtgcgccc ttttgagctg tcttttgctg      60
acgggttctt cttcaggttc tgataccggg agaccattcg ttgaaatgta tagtgagata     120
cccgaaatta tacatatgac tgaagggcgc gagctcgtca taccctgtcg ggtaacaagt     180
ccaaacataa cagtgaccct gaagaagttc cctttgata ctctcattcc cgacgggaag     240
cgaataattt gggactcaag gaagggatt tcatatcta atgcaacata taaggaaata      300
gggctcctca catgcgaagc cacagtcaac gggcacctct acaaaactaa ttacctgacc     360
catcgacaga caaataccat cattgatgtg ttctgagtc catctcatgg aatagagttg      420
agtgtagggg agaagcttgt tctcaattgc acagctagaa ccgagttgaa cgtgggtatc     480
gattttaact gggaataccc atctagtaag caccaacaca aaaaacttgt caatcgagat     540
ttgaaaactc aatctggtag cgagatgaaa aagttcctgt caactcttac aatcgatggc     600
gtgacccgga gtgatcaagg attgtatacc tgcgccgcca gctctggcct gatgactaaa     660
aagaacagca cctttgtacg agtgcatgaa aaggataaga ctcatacatg ccctccttgt     720
cccgctccag agctgctggg aggtcccagt gttttcctct ccccaccaaa gcccaaagat     780
actctgatga ttagccggac ccctgaggtg acttgcgtcg tggtggatgt tcacatgaa      840 gatccagaag tgaagttcaa ttggtacgtt gatggtgtgg aggtacacaa tgccaagact     900
aaacctcggg aggaacagta taacagcact tacagagttg tcagcgtact cacagtgctt     960
```

```
catcaggact ggttgaatgg taaggagtat aagtgcaaag tgagtaataa ggctctgcca    1020
gcacccatag agaagacaat ctcaaaggcc aaaggccagc cccgagaacc acaagtatac    1080
acactgccac ctagtagaga cgagttgaca aaaaatcagg tcagcctcac ctgtctcgtg    1140
aaaggcttct accctagcga cattgccgta gaatgggaaa gcaacgggca accagaaaac    1200
aattataaga caacacctcc cgttctcgat agtgacggaa gtttcttcct gtatagcaaa    1260
cttaccgtgg ataaatcaag atggcagcaa ggtaatgtgt ttagctgttc agtaatgcac    1320
gaagctctgc ataaccacta cacccaaaaa tctttgtctc tgtctccagg gtga          1374

<210> SEQ ID NO 9
<211> LENGTH: 3325
<212> TYPE: DNA
<213> ORGANISM: Artificial Sequence
<220> FEATURE:
<223> OTHER INFORMATION: synthetic

<400> SEQUENCE: 9
ggttggccac tccctctctg cgcgctcgct cgctcactga ggccgggcga ccaaaggtcg      60
cccgacgccc gggctttgcc cgggcggcct cagtgagcga gcgagcgcgc agagagggag     120
tggccaactc catcactagg ggttcctaga tctgaattcg gtaccctag ttattaatag      180 taatcaatta cggggtcatt agttcatagc ccatatatgg agttccgcgt tacataactt     240
acggtaaatg gcccgcctgg ctgaccgccc aacgaccccc gcccattgac gtcaataatg     300
acgtatgttc ccatagtaac gccaataggg actttccatt gacgtcaatg ggtggactat     360
ttacggtaaa ctgcccactt ggcagtacat caagtgtatc atatgccaag tacgccccct     420
attgacgtca atgacggtaa atggcccgcc tggcattatg cccagtacat gaccttatgg     480
gactttccta cttggcagta catctacgta ttagtcatcg ctattaccat ggtcgaggtg     540
agccccacgt tctgcttcac tctccccatc tcccccccct ccccaccccc aattttgtat     600
ttatttattt tttaattatt ttgtgcagcg atggggggg gggggggggg ggggcgcgcg     660
ccaggcgggg cggggcgggg cgaggggcgg ggcggggcga ggcggagagg tgcggcggca     720
gccaatcaga gcggcgcgct ccgaaagttt ccttttatgg cgaggcggcg gcggcggcgg     780
ccctataaaa agcgaagcgc gcggcgggcg ggagtcgctg cgacgctgcc ttcgccccgt     840
gccccgctcc gccgccgcct cgcgccgccc gccccggctc tgactgaccg cgttactccc     900
acaggtgagc gggcgggacg gcccttctcc tccgggctgt aattagcgct tggtttaatg     960
acggcttgtt tcttttctgt ggctgcgtga aagccttgag gggctccggg agctagagcc    1020
tctgctaacc atgttcatgc cttcttcttt ttcctacagc tcctgggcaa cgtgctggtt    1080
attgtgctgt ctcatcattt tggcaaagaa ttcctcgaag atctaggcaa cgcgtattgg    1140
gatctcgagg cggccgcgcc gccacccctag cgagagaatc ttctttctgt ctataaaaga    1200
gagaatcttc tttctgtcta taaaagagag aatcttcttt ctgtctataa agagagaat    1260 cttctttctg tctatgtcga ccctgcaatg gtatcatatt gggacacagg agtcctcctg    1320
tgcgcccttt tgagctgtct tttgctgacg ggttcttctt caggttctga taccgggaga    1380
ccattcgttg aaatgtatag tgagataccc gaaattatac atatgactga agggcgcgag    1440
ctcgtcatac cctgtcgggt aacaagtcca acataacag tgaccctgaa gaagttccct    1500
ttggatactc tcattcccga cgggaagcga ataatttggg actcaaggaa gggatttatc    1560
atatctaatg caacatataa ggaaataggg ctcctcacat gcgaagccac agtcaacggg    1620
cacctctaca aaactaatta cctgacccat cgacagacaa ataccatcat tgatgtggtt    1680
```

```
ctgagtccat ctcatggaat agagttgagt gtaggggaga agcttgttct caattgcaca    1740
gctagaaccg agttgaacgt gggtatcgat tttaactggg aatacccatc tagtaagcac    1800
caacacaaaa aacttgtcaa tcgagatttg aaaactcaat ctggtagcga gatgaaaaag    1860
ttcctgtcaa ctcttacaat cgatggcgtg acccggagtg atcaaggatt gtatacctgc    1920
gccgccagct ctggcctgat gactaaaaag aacagcacct ttgtacgagt gcatgaaaag    1980
gataagactc atacatgccc tccttgtccc gctccagagc tgctgggagg tcccagtgtt    2040
ttcctcttcc caccaaagcc caaagatact ctgatgatta gccggacccc tgaggtgact    2100
tgcgtcgtgg tggatgtttc acatgaagat ccagaagtga agttcaattg gtacgttgat    2160
ggtgtggagg tacacaatgc caagactaaa cctcgggagg aacagtataa cagcacttac    2220
agagttgtca gcgtactcac agtgcttcat caggactggt tgaatggtaa ggagtataag    2280
tgcaaagtga gtaataaggc tctgccagca cccatagaga agacaatctc aaaggccaaa    2340
ggccagcccc gagaaccaca agtatacaca ctgccaccta gtagagacga gttgacaaaa    2400
aatcaggtca gcctcacctg tctcgtgaaa ggcttctacc ctagcgacat tgccgtagaa    2460
tgggaaagca cgggcaacc agaaaacaat tataagacaa cacctcccgt tctcgatagt    2520
gacggaagtt tcttcctgta tagcaaactt accgtggata aatcaagatg gcagcaaggt    2580
aatgtgttta gctgttcagt aatgcacgaa gctctgcata accactacac ccaaaaatct    2640
ttgtctctgt ctccagggtg agcgtatcag caggtcccat aagctttcga caattaacga    2700
gtgtgtactc gttctatcat ctcacagtta aagtcgggag aataggagcc gcacgggtcc    2760
tgataccagc gtgagcggag agaatcttct ttctgtctat tagtgaagcc acagatgtaa    2820
tagacagaaa gaagattctc tccgcctacg cccttggcag caccgtacgg ttcgatcagc    2880
ttattggtac atgataagtc tcaggcatcg tacgatgtcg acctgcagga gtcggtcgac    2940
tagagctcgc tgatcagcct cgactgtgcc ttctagttgc cagccatctg ttgtttgccc    3000
ctcccccgtg ccttccttga ccctggaagg tgccactccc actgtccttt cctaataaaa    3060
tgaggaaatt gcatcgcatt gtctgagtag gtgtcattct attctggggg gtggggtggg    3120
gcaggacagc aagggggagg attgggaaga caatagcagg catgctgggg agagatctag    3180
gaacccctag tgatggagtt ggccactccc tctctgcgcg ctcgctcgct cactgaggcc    3240
gcccgggcaa agcccgggcg tcgggcgacc tttggtcgcc cggcctcagt gagcgagcga    3300
gcgcgcagag agggagtggc caacc                                          3325

<210> SEQ ID NO 10
<211> LENGTH: 27
<212> TYPE: DNA
<213> ORGANISM: Artificial Sequence
<220> FEATURE:
<223> OTHER INFORMATION: synthetic

<400> SEQUENCE: 10
gagagaatct tctttctgtc tataaaa                                           27

<210> SEQ ID NO 11
<211> LENGTH: 168
<212> TYPE: DNA
<213> ORGANISM: Artificial Sequence
<220> FEATURE:
<223> OTHER INFORMATION: synthetic

<400> SEQUENCE: 11
```

```
ctcgaggcga tcgcaaacaa acaaagctgt caccggatgt gctttccggt ctgatgagtc      60
cgttgtccaa taccagcatc gtcttgatgc ccttggcagt ggatggggac ggaggacgaa     120
acagcaaaaa gaaaaataaa aatttttttt ttaattaatc ttgggccc                  168
```

```
<210> SEQ ID NO 12
<211> LENGTH: 175
<212> TYPE: DNA
<213> ORGANISM: Artificial Sequence
<220> FEATURE:
<223> OTHER INFORMATION: synthetic

<400> SEQUENCE: 12
```

```
ctcgaggcga tcgcaaacaa acaaagctgt caccggatgt gctttccggt ctgatgagtc      60
cgttgtccaa aacataccag atttcgatct ggagaggtga agaattcgac cacctggacg     120
aggacggagg acgaaacagc aaaagaaaa ataaaaatta ttaatcttg ggccc            175
```

```
<210> SEQ ID NO 13
<211> LENGTH: 139
<212> TYPE: DNA
<213> ORGANISM: Artificial Sequence
<220> FEATURE:
<223> OTHER INFORMATION: synthetic

<400> SEQUENCE: 13
```

```
atggccggca tggtcccagc ctcctcgctg gcgccggctg ggcaaccaca taccagccga      60
aaggcccttg gcaggtgggc gaatgggacg cacaaatctc tctagcttcc cagagagaag     120
cgagagaaaa gtggctctc                                                  139
```

```
<210> SEQ ID NO 14
<211> LENGTH: 135
<212> TYPE: DNA
<213> ORGANISM: Artificial Sequence
<220> FEATURE:
<223> OTHER INFORMATION: synthetic

<400> SEQUENCE: 14
```

```
atggccggca tggtcccagc ctcctcgctg gcgccggctg ggcaatgcta taatcgcgtg      60
gatatggcac gcaagtttct accgggcacc gtaaatgtcc gactagtagc gaatgggacg     120
cacaaatctc tctag                                                      135
```

```
<210> SEQ ID NO 15
<211> LENGTH: 134
<212> TYPE: DNA
<213> ORGANISM: Artificial Sequence
<220> FEATURE:
<223> OTHER INFORMATION: synthetic

<400> SEQUENCE: 15
```

```
caaacaaaca aaggcgcgtc ctggattcgt ggtaaaacat accagatttc gatctggaga      60
ggtgaagaat acgaccacct gtagtatcca gctgatgagt cccaaatagg acgaaacgcg     120
ctaaacaaac aaac                                                       134
```

```
<210> SEQ ID NO 16
<211> LENGTH: 123
<212> TYPE: DNA
<213> ORGANISM: Artificial Sequence
<220> FEATURE:
<223> OTHER INFORMATION: synthetic

<400> SEQUENCE: 16
```

```
ctgaggtgca ggtacatcca gctgacgagt cccaaatagg acgaaaggga gaggtgaaga      60
atacgaccac ctaggctcga aagagcctaa aacatacctt tcctggattc cactgctatc     120
cac                                                                   123
```

<210> SEQ ID NO 17
<211> LENGTH: 286
<212> TYPE: DNA
<213> ORGANISM: Artificial Sequence
<220> FEATURE:
<223> OTHER INFORMATION: synthetic

<400> SEQUENCE: 17

```
ctagcacggg tccctaaaac ataccgtgag cgcgaaagcg cccccatttt gagttagtga      60
agccacagat gtaactcaaa atgggggcgc tttcccgcct acggagaggt gaagaatacg     120
accacctaga agcttattgg tacatgataa cacccccaaaa tcgaagcact tcaaaaacac    180
cccaaaatcg aagcacttca aaaacacccc aaaatcgaag cacttcaaaa acaccccaaa    240
atcgaagcac ttcagtctca ggcatcgtac gatgtcgacc tgcagg                   286
```

<210> SEQ ID NO 18
<211> LENGTH: 1376
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: SLIM regulatory element
<220> FEATURE:
<221> NAME/KEY: modified_base
<222> LOCATION: (1376)..(1376)
<223> OTHER INFORMATION: SLIM regulatory element

<400> SEQUENCE: 18

```
aatgtccatg ttgttctaca ctctgatcac agcttttctg atcggcatac aggcggaacc      60
acactcagtc tgataccggg agaccattcg ttgaaatgta tagtgagata cccgaaatta    120
tacatatgac tgaagggcgc gagctcgtca taccctgtcg ggtaacaagt ccaaacataa    180
cagtgaccct gaagaagttc cctttggata ctctcattcc cgacgggaag cgaataattt    240
gggactcaag gaagggattt atcatatcta atgcaacata taaggaaata gggctcctca    300
catgcgaagc cacagtcaac gggcacctct acaaaactaa ttacctgacc catcgacaga    360
caaataccat cattgatgtg gttctgagtc catctcatgg aatagagttg agtgtagggg    420
agaagcttgt tctcaattgc acagctagaa ccgagttgaa cgtgggtatc gattttaact    480
gggaataccc atctagtaag caccaacaca aaaaacttgt caatcgagat ttgaaaactc    540
aatctggtag cgagatgaaa aagttcctgt caactcttac aatcgatggc gtgacccgga    600
gtgatcaagg attgtatacc tgcgccgcca gctctggcct gatgactaaa agaacagca    660 ccttttgtacg agtgcatgaa aaggataaga ctcatacatg ccctccttgt cccgctccag    720
agctgctggg aggtcccagt gttttcctct tcccaccaaa gcccaaagat actctgatga    780
ttagccggac ccctgaggtg acttgcgtcg tggtggatgt ttcacatgaa gatccagaag    840
tgaagttcaa ttggtacgtt gatggtgtgg aggtacacaa tgccaagact aaacctcggg    900
aggaacagta taacagcact tacagagttg tcagcgtact cacagtgctt catcaggact    960
ggttgaatgg taaggagtat aagtgcaaag tgagtaataa ggctctgcca gcacccatag    1020
```

| | |
|---|---|
| agaagacaat ctcaaaggcc aaaggccagc cccgagaacc acaagtatac acactgccac | 1080 |
| ctagtagaga cgagttgaca aaaaatcagg tcagcctcac ctgtctcgtg aaaggcttct | 1140 |
| accctagcga cattgccgta gaatgggaaa gcaacgggca accagaaaac aattataaga | 1200 |
| caacacctcc cgttctcgat agtgacggaa gtttcttcct gtatagcaaa cttaccgtgg | 1260 |
| ataaatcaag atggcagcaa ggtaatgtgt ttagctgttc agtaatgcac gaagctctgc | 1320 |
| ataaccacta cacccaaaaa tctttgtctc tgtctccagg gtgaaaacaa acaaaa | 1376 |

```
<210> SEQ ID NO 19
<211> LENGTH: 2960
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1157)..(1157)
<223> OTHER INFORMATION: SLIM regulatory element
<220> FEATURE:
<221> NAME/KEY: modified_base
<222> LOCATION: (2550)..(2550)
<223> OTHER INFORMATION: SLIM regulatory element
```

<400> SEQUENCE: 19

| | |
|---|---|
| ggttggccac tccctctctg cgcgctcgct cgctcactga ggccgggcga ccaaaggtcg | 60 |
| cccgacgccc gggctttgcc cgggcggcct cagtgagcga gcgagcgcgc agagagggag | 120 |
| tggccaactc catcactagg ggttcctaga tctgaattcg gtaccctag ttattaatag | 180 |
| taatcaatta cggggtcatt agttcatagc ccatatatgg agttccgcgt tacataactt | 240 |
| acggtaaatg gcccgcctgg ctgaccgccc aacgaccccc gcccattgac gtcaataatg | 300 |
| acgtatgttc ccatagtaac gccaataggg actttccatt gacgtcaatg ggtggactat | 360 |
| ttacggtaaa ctgcccactt ggcagtacat caagtgtatc atatgccaag tacgccccct | 420 |
| attgacgtca atgacggtaa atggcccgcc tggcattatg cccagtacat gaccttatgg | 480 |
| gactttccta cttggcagta catctacgta ttagtcatcg ctattaccat ggtcgaggtg | 540 |
| agccccacgt tctgcttcac tctccccatc tcccccccct ccccacccc aattttgtat | 600 |
| ttatttattt tttaattatt ttgtgcagcg atggggcgg gggggggggg gggcgcgcg | 660 |
| ccaggcgggg cggggcgggg cgaggggcgg ggcggggcga ggcggagagg tgcggcggca | 720 |
| gccaatcaga gcggcgcgct ccgaaagttt cctttatgg cgaggcggcg gcggcggcgg | 780 |
| ccctataaaa agcgaagcgc gcggcgggcg ggagtcgctg cgacgctgcc ttcgccccgt | 840 |
| gccccgctcc gccgccgcct cgcgccgccc gccccggctc tgactgaccg cgttactccc | 900 |
| acaggtgagc gggcgggacg gcccttctcc tccgggctgt aattagcgct tggtttaatg | 960 |
| acggcttgtt tcttttctgt ggctgcgtga aagccttgag gggctccggg agctagagcc | 1020 |
| tctgctaacc atgttcatgc cttcttcttt ttcctacagc tcctgggcaa cgtgctggtt | 1080 |
| attgtgctgt ctcatcattt tggcaaagaa ttcctcgaag atctaggcaa cgcgtctcga | 1140 |
| ggcggccgcc gccaccaatg gtatcatatt gggacacagg agtcctcctg tgcgcccttt | 1200 |
| tgagctgtct tttgctgacg ggttcttctt caggttctga taccgggaga ccattcgttg | 1260 |
| aaatgtatag tgagataccc gaaattatac atatgactga agggcgcgag ctcgtcatac | 1320 |
| cctgtcgggt aacaagtcca aacataacag tgaccctgaa gaagttccct ttggatactc | 1380 |
| tcattcccga cgggaagcga ataatttggg actcaaggaa gggatttatc atatctaatg | 1440 |
| caacatataa ggaaataggg ctcctcacat gcgaagccac agtcaacggg cacctctaca | 1500 |

```
aaactaatta cctgacccat cgacagacaa ataccatcat tgatgtggtt ctgagtccat    1560
ctcatggaat agagttgagt gtaggggaga agcttgttct caattgcaca gctagaaccg    1620
agttgaacgt gggtatcgat tttaactggg aatacccatc tagtaagcac caacacaaaa    1680
aacttgtcaa tcgagatttg aaaactcaat ctggtagcga gatgaaaaag ttcctgtcaa    1740
ctcttacaat cgatggcgtg acccggagtg atcaaggatt gtatacctgc gccgccagct    1800
ctggcctgat gactaaaaag aacagcacct ttgtacgagt gcatgaaaag gataagactc    1860
atacatgccc tccttgtccc gctccagagc tgctgggagg tcccagtgtt ttcctcttcc    1920
caccaaagcc caaagatact ctgatgatta gccggacccc tgaggtgact tgcgtcgtgg    1980
tggatgtttc acatgaagat ccagaagtga agttcaattg gtacgttgat ggtgtggagg    2040
tacacaatgc caagactaaa cctcgggagg aacagtataa cagcacttac agagttgtca    2100
gcgtactcac agtgcttcat caggactggt tgaatggtaa ggagtataag tgcaaagtga    2160
gtaataaggc tctgccagca cccatagaga agacaatctc aaaggccaaa ggccagcccc    2220
gagaaccaca agtatacaca ctgccaccta gtagagacga gttgacaaaa atcaggtca    2280 gcctcacctg tctcgtgaaa ggcttctacc ctagcgacat tgccgtagaa tgggaaagca    2340
acgggcaacc agaaaacaat tataagacaa cacctcccgt tctcgatagt gacggaagtt    2400
tcttcctgta tagcaaactt accgtggata atcaagatg gcagcaaggt aatgtgttta    2460
gctgttcagt aatgcacgaa gctctgcata accactacac ccaaaaatct ttgtctctgt    2520
ctccagggtg agcggccgca tcggctagca aagcttcctg caggagtcgg tcgactagag    2580
ctcgctgatc agcctcgact gtgccttcta gttgccagcc atctgttgtt tgcccctccc    2640
ccgtgccttc cttgaccctg gaaggtgcca ctcccactgt cctttcctaa taaaatgagg    2700
aaattgcatc gcattgtctg agtaggtgtc attctattct ggggggtggg gtggggcagg    2760
acagcaaggg ggaggattgg gaagacaata gcaggcatgc tggggagaga tctaggaacc    2820
cctagtgatg gagttggcca ctccctctct gcgcgctcgc tcgctcactg aggccgcccg    2880
ggcaaagccc gggcgtcggg cgacctttgg tcgcccggcc tcagtgagcg agcgagcgcg    2940
cagagaggga gtggccaacc                                                2960
```

<210> SEQ ID NO 20
<211> LENGTH: 1374
<212> TYPE: DNA
<213> ORGANISM: Artificial Sequence
<220> FEATURE:
<223> OTHER INFORMATION: synthetic

<400> SEQUENCE: 20

```
atggtatcat attgggacac aggagtcctc ctgtgcgccc ttttgagctg tcttttgctg     60
acgggttctt cttcaggttc tgataccggg agaccattcg ttgaaatgta tagtgagata    120
cccgaaatta tacatatgac tgaagggcgc gagctcgtca tacccgtgcg ggtaacaagt    180
ccaaacataa cagtgacccc tgaagaagttc cctttggata ctctcattcc cgacgggaag    240
cgaataattt gggactcaag gaagggattt atcatatcta atgcaacata taggaaaata    300
gggctcctca catgcgaagc cacagtcaac gggcacctct acaaaactaa ttacctgacc    360
catcgacaga caaataccat cattgatgtg ttctgagtc catctcatgg aatagagttg    420
agtgtagggg agaagcttgt tctcaattgc acagctagaa ccgagttgaa cgtgggtatc    480
gattttaact gggaataccc atctagtaag caccaacaca aaaaacttgt caatcgagat    540
```

```
ttgaaaactc aatctggtag cgagatgaaa aagttcctgt caactcttac aatcgatggc    600
gtgacccgga gtgatcaagg attgtatacc tgcgccgcca gctctggcct gatgactaaa    660
aagaacagca cctttgtacg agtgcatgaa aaggataaga ctcatacatg ccctccttgt    720
cccgctccag agctgctggg aggtcccagt gttttcctct tcccaccaaa gcccaaagat    780
actctgatga ttagccggac ccctgaggtg acttgcgtcg tggtggatgt tcacatgaa     840 gatccagaag tgaagttcaa ttggtacgtt gatggtgtgg aggtacacaa tgccaagact    900
aaacctcggg aggaacagta taacagcact tacagagttg tcagcgtact cacagtgctt    960
catcaggact ggttgaatgg taaggagtat aagtgcaaag tgagtaataa ggctctgcca   1020
gcacccatag agaagacaat ctcaaaggcc aaaggccagc ccgagaacc acaagtatac    1080 acactgccac ctagtagaga cgagttgaca aaaaatcagg tcagcctcac ctgtctcgtg   1140
aaaggcttct accctagcga cattgccgta aatgggaaa gcaacgggca accagaaaac    1200
aattataaga caacacctcc cgttctcgat agtgacggaa gtttcttcct gtatagcaaa   1260
cttaccgtgg ataaatcaag atggcagcaa ggtaatgtgt ttagctgttc agtaatgcac   1320
gaagctctgc ataaccacta cacccaaaaa tctttgtctc tgtctccagg gtga         1374
```

```
<210> SEQ ID NO 21
<211> LENGTH: 153
<212> TYPE: DNA
<213> ORGANISM: Artificial Sequence
<220> FEATURE:
<223> OTHER INFORMATION: synthetic

<400> SEQUENCE: 21
gaacgcctcc taacgtctgg tcacgaccct gcgtgagcga ccccattgtt caggtttgta    60
ttcttttggc cactgactga gaatacaaat gaacaatggg ggcgcctacg cagcccctcg   120
aaatcacgag ggagacgaga taaggggcg ttt                                 153
```

```
<210> SEQ ID NO 22
<211> LENGTH: 155
<212> TYPE: DNA
<213> ORGANISM: Artificial Sequence
<220> FEATURE:
<223> OTHER INFORMATION: synthetic

<400> SEQUENCE: 22
gaacgcctcc taacgtctgg tcacgaccct gcgtgagcga ccctgagttc cttccctaaa    60
tacttttggc cactgactga gtatttagga ggaactcagg ggggcgccta cgcagcccct   120
cgaaatcacg agggagacga gataaggggg cgttt                              155
```

```
<210> SEQ ID NO 23
<211> LENGTH: 155
<212> TYPE: DNA
<213> ORGANISM: Artificial Sequence
<220> FEATURE:
<223> OTHER INFORMATION: synthetic

<400> SEQUENCE: 23
gaacgcctcc taacgtctgg tcacgaccct gcgtgagcga ccaagagtta acgtgtcgat    60
ctcttttggc cactgactga gagatcgacg ttaactcttg ggggcgccta cgcagcccct   120
cgaaatcacg agggagacga gataaggggg cgttt                              155
```

```
<210> SEQ ID NO 24
<211> LENGTH: 155
```

```
<212> TYPE: DNA
<213> ORGANISM: Artificial Sequence
<220> FEATURE:
<223> OTHER INFORMATION: synthetic

<400> SEQUENCE: 24
gaacgcctcc taacgtctgg tcacgaccct gcgtgagcga cccttcccta aatagtatag    60
atcttttggc cactgactga gatctatact ttagggaagg ggggcgccta cgcagcccct   120
cgaaatcacg agggagacga gataagggg cgttt                               155

<210> SEQ ID NO 25
<211> LENGTH: 155
<212> TYPE: DNA
<213> ORGANISM: Artificial Sequence
<220> FEATURE:
<223> OTHER INFORMATION: synthetic

<400> SEQUENCE: 25
gaacgcctcc taacgtctgg tcacgaccct gcgtgagcga ccgtgtcgat cttggctcaa    60
ctcttttggc cactgactga gcgtgtcgat tggctcaact ggggcgccta cgcagcccct   120
cgaaatcacg agggagacga gataagggg cgttt                               155

<210> SEQ ID NO 26
<211> LENGTH: 127
<212> TYPE: DNA
<213> ORGANISM: Artificial Sequence
<220> FEATURE:
<223> OTHER INFORMATION: synthetic

<400> SEQUENCE: 26
gaacgcctcc ttgataccag ctgcgtgagc gaccccattg ttcaggtttg tattcttttg    60
gccactgact gagaatacaa atgaacaatg ggggcgccta cgcgcccttg gcagcaaggg   120
ggcgttt                                                             127

<210> SEQ ID NO 27
<211> LENGTH: 129
<212> TYPE: DNA
<213> ORGANISM: Artificial Sequence
<220> FEATURE:
<223> OTHER INFORMATION: synthetic

<400> SEQUENCE: 27
gaacgcctcc ttgataccag ctgcgtgagc gaccctgagt tccttccctaa atacttttg    60 gccactgact gagtatttag gaggaactca gggggggcgcc tacgcgccct tggcagcaag   120
ggggcgttt                                                           129

<210> SEQ ID NO 28
<211> LENGTH: 129
<212> TYPE: DNA
<213> ORGANISM: Artificial Sequence
<220> FEATURE:
<223> OTHER INFORMATION: synthetic

<400> SEQUENCE: 28
gaacgcctcc ttgataccag ctgcgtgagc gaccaagagt taacgtgtcg atctcttttg    60
gccactgact gagagatcga cgttaactct tggggcgcc tacgcgccct tggcagcaag    120
ggggcgttt                                                           129

<210> SEQ ID NO 29
```

```
<211> LENGTH: 129
<212> TYPE: DNA
<213> ORGANISM: Artificial Sequence
<220> FEATURE:
<223> OTHER INFORMATION: synthetic

<400> SEQUENCE: 29
gaacgcctcc ttgataccag ctgcgtgagc gacccttccc taaatagtat agatcttttg      60
gccactgact gagatctata ctttagggaa ggggggcgcc tacgcgccct tggcagcaag     120
ggggcgttt                                                            129

<210> SEQ ID NO 30
<211> LENGTH: 129
<212> TYPE: DNA
<213> ORGANISM: Artificial Sequence
<220> FEATURE:
<223> OTHER INFORMATION: synthetic

<400> SEQUENCE: 30
gaacgcctcc ttgataccag ctgcgtgagc gaccgtgtcg atcttggctc aactcttttg      60
gccactgact gagcgtgtcg attggctcaa ctggggcgcc tacgcgccct tggcagcaag     120
ggggcgttt                                                            129

<210> SEQ ID NO 31
<211> LENGTH: 151
<212> TYPE: DNA
<213> ORGANISM: Artificial Sequence
<220> FEATURE:
<223> OTHER INFORMATION: synthetic

<400> SEQUENCE: 31
gaacgcctcc tagaggtgaa gaatacgacc accttgcgtg agcgacccca ttgttcaggt      60
ttgtattctt ttggccactg actgagaata caaatgaaca atgggggcgc ctacgcaggc     120
tcgaaagagc ctaaaacata aggggcgtt t                                    151

<210> SEQ ID NO 32
<211> LENGTH: 153
<212> TYPE: DNA
<213> ORGANISM: Artificial Sequence
<220> FEATURE:
<223> OTHER INFORMATION: synthetic

<400> SEQUENCE: 32
gaacgcctcc tagaggtgaa gaatacgacc accttgcgtg agcgaccctg agttccttcc      60
ctaaatactt ttggccactg actgagtatt taggaggaac tcaggggggc gcctacgcag     120
gctcgaaaga gcctaaaaca taaggggggcg ttt                                 153

<210> SEQ ID NO 33
<211> LENGTH: 153
<212> TYPE: DNA
<213> ORGANISM: Artificial Sequence
<220> FEATURE:
<223> OTHER INFORMATION: synthetic

<400> SEQUENCE: 33
gaacgcctcc tagaggtgaa gaatacgacc accttgcgtg agcgaccaag agttaacgtg      60
tcgatctctt ttggccactg actgagagat cgacgttaac tcttggggc gcctacgcag     120 gctcgaaaga gcctaaaaca taaggggggcg ttt                                 153
```

```
<210> SEQ ID NO 34
<211> LENGTH: 153
<212> TYPE: DNA
<213> ORGANISM: Artificial Sequence
<220> FEATURE:
<223> OTHER INFORMATION: synthetic

<400> SEQUENCE: 34
gaacgcctcc tagaggtgaa gaatacgacc accttgcgtg agcgacccct ccctaaatag      60
tatagatctt ttggccactg actgagatct atactttagg aaggggggc gcctacgcag      120 gctcgaaaga gcctaaaaca taaggggcg ttt                                   153

<210> SEQ ID NO 35
<211> LENGTH: 153
<212> TYPE: DNA
<213> ORGANISM: Artificial Sequence
<220> FEATURE:
<223> OTHER INFORMATION: synthetic

<400> SEQUENCE: 35
gaacgcctcc tagaggtgaa gaatacgacc accttgcgtg agcgaccgtg tcgatcttgg      60
ctcaactctt ttggccactg actgagcgtg tcgattggct caactggggc gcctacgcag     120
gctcgaaaga gcctaaaaca taaggggcg ttt                                   153

<210> SEQ ID NO 36
<211> LENGTH: 2077
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: SLIM regulatory element
<220> FEATURE:
<221> NAME/KEY: modified_base
<222> LOCATION: (2077)..(2077)
<223> OTHER INFORMATION: SLIM regulatory element

<400> SEQUENCE: 36
aatggtcagc tactgggaca ccggggtcct gctgtgcgcg ctgctcagct gtctgcttct      60
cacaggatct agttcaggtt caaaattaaa agatcctgaa ctgagtttaa aaggcaccca     120
gcacatcatg caagcaggcc agacactgca tctccaatgc aggggggaag cagcccataa     180
atggtctttg cctgaaatgg tgagtaagga aagcgaaagg ctgagcataa ctaaatctgc     240
ctgtggaaga aatggcaaac aattctgcag tactttaacc ttgaacacag ctcaagcaaa     300
ccacactggc ttctacagct gcaaatatct agctgtacct acttcaaaga agaaggaaac     360
agaatctgca atctatatat ttattagtga tacaggtaga cctttcgtag agatgtacag     420
tgaaatcccc gaattatac acatgactga aggaagggag ctcgtcattc cctgccgggt     480
tacgtcacct aacatcactg ttactttaaa aaagtttcca cttgacactt tgatccctga     540
tggaaaacgc ataatctggg acagtagaaa gggcttcatc atatcaaatg caacgtacaa     600
agaaataggg cttctgacct gtgaagcaac agtcaatggg catttgtata agacaaacta     660
tctcacacat cgacaaacca atacaatcat agatgtccaa ataagcacac acgcccagt     720 caaattactt agaggccata tcttgtcct caattgtact gctaccactc ccttgaacac      780
gagagttcaa atgacctgga gttaccctga tgaaaaaaat aagagagctt ccgtaaggcg     840
acgaattgac caaagcaatt cccatgccaa catattctac agtgttctta ctattgacaa     900
```

```
aatgcagaac aaagacaaag gactttatac ttgtcgtgta aggagtggac catcattcaa    960
atctgttaac acctcagtgc atatatatga taaagcattc atcactgtga aacatcgaaa   1020
acagcaggtg cttgaaaccg tagctggcaa gcggtcttac cggctctcta tgaaagtgaa   1080
ggcatttccc tcgccggaag ttgtatggtt aaaagatggg ttacctgcga ctgagaaatc   1140
tgctcgctat ttgactcgtg gctactcgtt aattatcaag gacgtaactg aagaggatgc   1200
agggaattat acaatcttgc tgagcataaa acagtcaaat gtgtttaaaa acctcactgc   1260
cactctaatt gtcaatgtga aaccccagat ttacgaaaag gccgtgtcat cgtttccaga   1320
cccggctctc tacccactgg gcagcagaca atcctgact  tgtaccgcat atggtatccc   1380
tcaacctaca atcaagtggt tctggcaccc ctgtaaccat aatcattccg aagcaaggtg   1440
tgacttttgt tccaataatg aagagtcctt tatcctggat gctgacagca acatgggaaa   1500
cagaattgag agcatcactc agcgcatggc aataatagaa ggaaagaata agatggctag   1560
caccttggtt gtggctgact ctagaatttc tggaatctac atttgcatag cttccaataa   1620
agttgggact gtgggaagaa acataagctt ttatatcaca gatgtgccaa atgggtttca   1680
tgttaacttg gaaaaaatgc cgacggaagg agaggacctg aaactgtctt gcacagttaa   1740
caagttctta tacagagacg ttacttggat tttactgcgg acagttaata acagaacaat   1800
gcactacagt attagcaagc aaaaaatggc catcactaag gagcactcca tcactcttaa   1860
tcttaccatc atgaatgttt ccctgcaaga ttcaggcacc tatgcctgca gagccaggaa   1920
tgtatacaca ggggaagaaa tcctccagaa gaaagaaatt acaatcagag gtgagcactg   1980
caacaaaaag gctgttttct ctcggatctc caaatttaaa agcacaagga atgattgtac   2040
cacacaaagt aatgtaaaac attaaaaaca aacaaaa                            2077

<210> SEQ ID NO 37
<211> LENGTH: 155
<212> TYPE: DNA
<213> ORGANISM: Artificial Sequence
<220> FEATURE:
<223> OTHER INFORMATION: synthetic

<400> SEQUENCE: 37
gaacgcctcc taacgtctgg tcacgaccct gcgtgagcga ccagacgaag agtgtcctag    60
atcttttggc cactgactga gatctaggac tcttcgtctg ggggcgccta cgcagcccct   120
cgaaatcacg agggagacga gataagggg  cgttt                              155

<210> SEQ ID NO 38
<211> LENGTH: 155
<212> TYPE: DNA
<213> ORGANISM: Artificial Sequence
<220> FEATURE:
<223> OTHER INFORMATION: synthetic

<400> SEQUENCE: 38
gaacgcctcc taacgtctgg tcacgaccct gcgtgagcga ccgctttccg actcgtattg    60
atcttttggc cactgactga gatcaatacg tcggaaagcg ggggcgccta cgcagcccct   120
cgaaatcacg agggagacga gataagggg  cgttt                              155

<210> SEQ ID NO 39
<211> LENGTH: 155
<212> TYPE: DNA
<213> ORGANISM: Artificial Sequence
<220> FEATURE:
<223> OTHER INFORMATION: synthetic
```

```
<400> SEQUENCE: 39
gaacgcctcc taacgtctgg tcacgaccct gcgtgagcga ccaccttctt taccgtttgt    60
tacttttggc cactgactga gtaacaaact aaagaaggtg ggggcgccta cgcagcccct   120
cgaaatcacg agggagacga gataaggggg cgttt                              155

<210> SEQ ID NO 40
<211> LENGTH: 155
<212> TYPE: DNA
<213> ORGANISM: Artificial Sequence
<220> FEATURE:
<223> OTHER INFORMATION: synthetic

<400> SEQUENCE: 40
gaacgcctcc taacgtctgg tcacgaccct gcgtgagcga cccgtttgtt aagacgtcat    60
gacttttggc cactgactga gtcatgacgt taacaaacgg ggggcgccta cgcagcccct   120
cgaaatcacg agggagacga gataaggggg cgttt                              155

<210> SEQ ID NO 41
<211> LENGTH: 155
<212> TYPE: DNA
<213> ORGANISM: Artificial Sequence
<220> FEATURE:
<223> OTHER INFORMATION: synthetic

<400> SEQUENCE: 41
gaacgcctcc taacgtctgg tcacgaccct gcgtgagcga cgcaaatatc tagctgtacc    60
tacttttggc cactgactga gtaggtacat agatatttgc ggggcgccta cgcagcccct   120
cgaaatcacg agggagacga gataaggggg cgttt                              155

<210> SEQ ID NO 42
<211> LENGTH: 129
<212> TYPE: DNA
<213> ORGANISM: Artificial Sequence
<220> FEATURE:
<223> OTHER INFORMATION: synthetic

<400> SEQUENCE: 42
gaacgcctcc ttgataccag ctgcgtgagc gaccagacga agagtgtcct agatcttttg    60
gccactgact gagatctagg actcttcgtc tgggggcgcc tacgcgccct tggcagcaag   120
ggggcgttt                                                           129

<210> SEQ ID NO 43
<211> LENGTH: 129
<212> TYPE: DNA
<213> ORGANISM: Artificial Sequence
<220> FEATURE:
<223> OTHER INFORMATION: synthetic

<400> SEQUENCE: 43
gaacgcctcc ttgataccag ctgcgtgagc gaccgctttc cgactcgtat tgatcttttg    60
gccactgact gagatcaata cgtcggaaag cggggggcgcc tacgcgccct tggcagcaag   120
ggggcgttt                                                           129

<210> SEQ ID NO 44
<211> LENGTH: 129
<212> TYPE: DNA
<213> ORGANISM: Artificial Sequence
<220> FEATURE:
```

<223> OTHER INFORMATION: synthetic

<400> SEQUENCE: 44

```
gaacgcctcc ttgataccag ctgcgtgagc gaccaccttc tttaccgttt gttacttttg      60
gccactgact gagtaacaaa ctaaagaagg tgggggcgcc tacgcgccct tggcagcaag     120
ggggcgttt                                                             129
```

<210> SEQ ID NO 45
<211> LENGTH: 129
<212> TYPE: DNA
<213> ORGANISM: Artificial Sequence
<220> FEATURE:
<223> OTHER INFORMATION: synthetic

<400> SEQUENCE: 45

```
gaacgcctcc ttgataccag ctgcgtgagc gacccgtttg ttaagacgtc atgacttttg      60
gccactgact gagtcatgac gttaacaaac ggggggcgcc tacgcgccct tggcagcaag     120
ggggcgttt                                                             129
```

<210> SEQ ID NO 46
<211> LENGTH: 129
<212> TYPE: DNA
<213> ORGANISM: Artificial Sequence
<220> FEATURE:
<223> OTHER INFORMATION: synthetic

<400> SEQUENCE: 46

```
gaacgcctcc ttgataccag ctgcgtgagc gacgcaaata tctagctgta cctacttttg      60
gccactgact gagtaggtac atagatattt gcggggcgcc tacgcgccct tggcagcaag     120
ggggcgttt                                                             129
```

<210> SEQ ID NO 47
<211> LENGTH: 153
<212> TYPE: DNA
<213> ORGANISM: Artificial Sequence
<220> FEATURE:
<223> OTHER INFORMATION: synthetic

<400> SEQUENCE: 47

```
gaacgcctcc tagaggtgaa gaatacgacc accttgcgtg agcgaccaga cgaagagtgt      60
cctagatctt ttggccactg actgagatct aggactcttc gtctgggggc gcctacgcag     120
gctcgaaaga gcctaaaaca taagggggcg ttt                                  153
```

<210> SEQ ID NO 48
<211> LENGTH: 153
<212> TYPE: DNA
<213> ORGANISM: Artificial Sequence
<220> FEATURE:
<223> OTHER INFORMATION: synthetic

<400> SEQUENCE: 48

```
gaacgcctcc tagaggtgaa gaatacgacc accttgcgtg agcgaccgct ttccgactcg      60
tattgatctt ttggccactg actgagatca atacgtcgga aagcggggc gcctacgcag     120
gctcgaaaga gcctaaaaca taagggggcg ttt                                  153
```

<210> SEQ ID NO 49
<211> LENGTH: 153
<212> TYPE: DNA
<213> ORGANISM: Artificial Sequence

```
<220> FEATURE:
<223> OTHER INFORMATION: synthetic

<400> SEQUENCE: 49
gaacgcctcc tagaggtgaa gaatacgacc accttgcgtg agcgaccacc ttctttaccg      60
tttgttactt ttggccactg actgagtaac aaactaaaga aggtggggc gcctacgcag      120 gctcgaaaga gcctaaaaca taaggggcg ttt                                   153

<210> SEQ ID NO 50
<211> LENGTH: 153
<212> TYPE: DNA
<213> ORGANISM: Artificial Sequence
<220> FEATURE:
<223> OTHER INFORMATION: synthetic

<400> SEQUENCE: 50
gaacgcctcc tagaggtgaa gaatacgacc accttgcgtg agcgacccgt ttgttaagac      60
gtcatgactt ttggccactg actgagtcat gacgttaaca aacggggggc gcctacgcag     120
gctcgaaaga gcctaaaaca taaggggcg ttt                                   153

<210> SEQ ID NO 51
<211> LENGTH: 142
<212> TYPE: DNA
<213> ORGANISM: Artificial Sequence
<220> FEATURE:
<223> OTHER INFORMATION: synthetic

<400> SEQUENCE: 51
gaacgcctcc tagaggtgaa gaatacgacc accttgcgtg agcgacgcaa atatctagct      60
gtacctactt ttggccactg actgagtagg tacatagata tttgcggggc gcctacgcag     120
gctcgaaaga gcctaaaaca ta                                              142

<210> SEQ ID NO 52
<211> LENGTH: 1815
<212> TYPE: DNA
<213> ORGANISM: Artificial Sequence
<220> FEATURE:
<223> OTHER INFORMATION: synthetic

<400> SEQUENCE: 52
atgcttgccc gggccctgct tctgtgtgcg gtattggcac tgagtcacac agccaacccg       60
tgctgctcac acccatgtca gaatcgggga gtttgcatgt cagtagggtt tgaccaatat     120
aagtgcgact gtacccggac aggcttttat ggagaaaatt gttctacacc cgaatttttg     180
acgaggatta agctctttct gaagcctaca ccaaatacag tccattatat cctcacgcac     240
ttcaagggtt tttggaatgt cgtaaacaac attccgtttc tgagaaatgc gataatgtct     300
tacgtcctta catcccggag ccaccttatt gactcacccc caacatacaa cgccgactac     360
ggatacaaaa gttgggaagc tttctccaac ctgtcttact acacgcgagc attgcctcct     420
gtacccgacg attgcccgac gccgttgggg gtgaaaggaa aaagcagct cccggactca      480 aacgaaatag tagagaaatt gttgcttcgc cgaaaattta ccagaccc gcagggtagc       540 aatatgatgt ttgcgttctt cgctcagcac ttcactcacc aattctttaa gacagaccac     600
aagagaggtc ccgcattcac gaatggcctt ggacacggcg tcgacttgaa ccacatatat     660
ggggagacat tggccagaca aaggaaactt cgattgttta aggatgggaa aatgaaatac     720
caaattattg atggcgagat gtatcctcca acagtgaagg atacgcaagc ggagatgatt     780
```

```
tatccaccgc aggtaccaga gcatttgcgg ttcgcggtgg ggcaggaagt atttggactt      840
gttcccggtc tgatgatgta cgccacaata tggctccggg agcataatcg cgtgtgtgac      900
gtacttaagc aagagcaccc ggaatggggc gacgagcaac ttttcaaac gagtcgactg       960 attctcattg gggaaacgat taaaatagtg atcgaagatt atgtgcaaca tctttctggt     1020 taccactttta agttgaagtt cgatcctgag ctgcttttca ataaacaatt ccagtatcaa    1080
aacagaatcg ccgcggagtt caacacgctg tatcattggc atccctgtt gcccgatact      1140 tttcaaatcc atgaccagaa atacaattac cagcaattta tatataataa ctctatcctc    1200
ctggagcatg gcattacaca attcgttgaa agtttcacaa ggcagatcgc aggaagagtt    1260
gcgggtggcc ggaatgtgcc gcctgccgtg caaaaggtat cacaggctag catcgaccaa    1320
tcaaggcaaa tgaagtacca gtcttttaat gagtacagga aaggttcat gctgaagcct     1380 tacgagagct ttgaagaact gacgggcgaa aaggaaatgt ccgcggaact ggaagcgttg    1440
tacggagata ttgatgcggt agagctctac cccgcgcttc tggtcgaaaa gccccggcca    1500
gatgccattt tcggggaaac catggttgaa gtgggcgccc cattcagttt gaaaggtctg    1560
atgggtaatg taatttgcag tccggcgtac tggaagcctt ccacttttgg tggggaagtg    1620
gggtttcaaa ttatcaatac ggcctcaatt cagtctctga tttgtaacaa tgttaaggga    1680
tgtcccttta catctttag tgtaccggac cccgagctta ttaagaccgt gaccataaat     1740
gcttcaagct ctagaagtgg tcttgatgat atcaaccca cagttttgct taaggaaagg     1800
agcacggagc tctaa                                                     1815

<210> SEQ ID NO 53
<211> LENGTH: 894
<212> TYPE: DNA
<213> ORGANISM: Artificial Sequence
<220> FEATURE:
<223> OTHER INFORMATION: synthetic

<400> SEQUENCE: 53
atgagcatga acaactcaaa acagttggtc tccccagcag cggccctttt gtccaacaca       60
acgtgtcaga ctgagaatag actcagtgta tttttagcg tgatttttat gaccgtcggt      120
atcctgtcta actctcttgc catagcaata ttgatgaaag cctatcagcg attccggcaa     180
aagtctaagg cgtcatttt gttgttggca agcgggcttg tcatcacgga cttttcggg      240 cacctcatta acgagccat agccgtgttc gtttatgctt cagacaaaga gtggatacga     300
ttcgatcaga gcaatgtgct ttgcagtatc tttggcatat gtatggtgtt tagtggattg    360
tgtccactct tgcttgggag cgtgatggct attgaaagat gcatcggggt gactaaacct    420
atctttcaca gtaccaaaat tacatctaag cacgtcaaga tgatgttgtc cggggtgtgt    480
ctttttgctg tctttattgc gttgttgcca atactgggcc acagggacta caaaattcag    540
gcctcacgca cttggtgctt ctataacact gaggatatta agactggga ggataggttt      600 tatcttcttc ttttctcatt cctcggtctg ctcgcactgg gggtatccct tttgtgtaac    660
gctatcacag gtatcacctt gttgcgcgtt aaatttaaga gccaacagca tcgccagggg    720
aggtcacatc acctcgaaat ggtaatacag ttgctcgcga tcatgtgtgt tagttgtatc    780
tgctggtcac ccttcttggg atatagaata attctgaatg gaaaagaaaa gtacaaagtc    840
tatgaagaac agagcgattt tctgcatcga ttgcaatggc ccactttgga ataa           894

<210> SEQ ID NO 54
<211> LENGTH: 2771
```

```
<212> TYPE: DNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: SLIM regulatory element
<220> FEATURE:
<221> NAME/KEY: modified_base
<222> LOCATION: (2771)..(2771)
<223> OTHER INFORMATION: SLIM regulatory element

<400> SEQUENCE: 54
aatgcttgcc cgggccctgc ttctgtgtgc ggtattggca ctgagtcaca cagccaaccc    60
gtgctgctca cacccatgtc agaatcgggg agtttgcatg tcagtagggt ttgaccaata   120
taagtgcgac tgtacccgga caggctttta tggagaaaat tgttctacac ccgaattttt   180
gacgaggatt aagctctttc tgaagcctac accaaataca gtccattata tcctcacgca   240
cttcaagggt ttttggaatg tcgtaaacaa cattccgttt ctgagaaatg cgataatgtc   300
ttacgtcctt acatcccgga gccaccttat tgactcaccc ccaacataca acgccgacta   360
cggatacaaa agttgggaag ctttctccaa cctgtcttac tacacgcgag cattgcctcc   420
tgtacccgac gattgcccga cgccgttggg ggtgaaagga aaaagcagc tcccggactc   480
aaacgaaata gtagagaaat tgttgcttcg ccgaaaattt ataccagacc cgcagggtag   540
caatatgatg tttgcgttct tcgctcagca cttcactcac caattcttta agacagacca   600
caagagaggt cccgcattca cgaatggcct tggacacggc gtcgacttga accacatata   660
tggggagaca ttggccagac aaaggaaact tcgattgttt aaggatggga aaatgaaata   720
ccaaattatt gatggcgaga tgtatcctcc aacagtgaag gatacgcaag cggagatgat   780
ttatccaccg caggtaccag agcatttgcg gttcgcggtg gggcaggaag tatttggact   840
tgttcccggt ctgatgatgt acgccacaat atggctccgg gagcataatc gcgtgtgtga   900
cgtacttaag caagagcacc cggaatgggg cgacgagcaa cttttcaaa cgagtcgact   960
gattctcatt ggggaaacga ttaaaatagt gatcgaagat tatgtgcaac atctttctgg  1020
ttaccacttt aagttgaagt tcgatcctga gctgcttttc aataaacaat tccagtatca  1080
aaacagaatc gccgcggagt tcaacacgct gtatcattgg catcccctgt tgcccgatac  1140
ttttcaaatc catgaccaga aatacaatta ccagcaattt atatataata actctatcct  1200
cctggagcat ggcattacac aattcgttga agtttcaca aggcagatcg caggaagagt  1260
tgcgggtggc cggaatgtgc cgcctgccgt gcaaaaggta tcacaggcta gcatcgacca  1320
atcaaggcaa atgaagtacc agtcttttaa tgagtacagg aaaaggttca tgctgaagcc  1380
ttacgagagc tttgaagaac tgacgggcga aaaggaaatg tccgcggaac tggaagcgtt  1440
gtacggagat attgatgcgg tagagctcta ccccgcgctt ctggtcgaaa agccccggcc  1500
agatgccatt ttcggggaaa ccatggttga agtgggcgcc ccattcagtt tgaaaggtct  1560
gatgggtaat gtaatttgca gtccggcgta ctggaagcct tccactttgt gtgggaagt   1620
ggggtttcaa attatcaata cggcctcaat tcagtctctg atttgtaaca atgttaaggg  1680
atgtcccttt acatctttta gtgtaccgga ccccgagctt attaagaccg tgaccataaa  1740
tgcttcaagc tctagaagtg gtcttgatga tatcaacccc acagttttgc ttaaggaaag  1800
gagcacggag ctcggaagcg gagctactaa cttcagcctg ctgaagcagg ctggagacgt  1860
cgaggagaac cctggaccta gcatgaacaa ctcaaaacag ttggtctccc cagcagcggc  1920
```

```
ccttttgtcc aacacaacgt gtcagactga gaatagactc agtgtatttt ttagcgtgat    1980
ttttatgacc gtcggtatcc tgtctaactc tcttgccata gcaatattga tgaaagccta    2040
tcagcgattc cggcaaaagt ctaaggcgtc attttgttg ttggcaagcg ggcttgtcat    2100
cacggacttt tcgggcacc tcattaacgg agccatagcc gtgttcgttt atgcttcaga    2160
caaagagtgg atacgattcg atcagagcaa tgtgctttgc agtatctttg gcatatgtat    2220
ggtgtttagt ggattgtgtc cactcttgct tgggagcgtg atggctattg aaagatgcat    2280
cggggtgact aaacctatct ttcacagtac caaaattaca tctaagcacg tcaagatgat    2340
gttgtccggg gtgtgtcttt tgctgtgtctt tattgcgttg ttgccaatac tgggccacag    2400
ggactacaaa attcaggcct cacgcacttg gtgcttctat aacactgagg atattaaaga    2460 ctggaggat aggttttatc ttcttcttt ctcattcctc ggtctgctcg cactgggggt     2520
atcccttttg tgtaacgcta tcacaggtat caccttgttg cgcgttaaat ttaagagcca    2580
acagcatcgc caggggaggt cacatcacct cgaaatggta atacagttgc tcgcgatcat    2640
gtgtgttagt tgtatctgct ggtcacccctt cttgggatat agaataattc tgaatggaaa    2700
agaaaagtac aaagtctatg aagaacagag cgattttctg catcgattgc aatggcccac    2760
tttggaataa a                                                          2771

<210> SEQ ID NO 55
<211> LENGTH: 1812
<212> TYPE: DNA
<213> ORGANISM: Artificial Sequence
<220> FEATURE:
<223> OTHER INFORMATION: synthetic

<400> SEQUENCE: 55
atgcttgccc gggccctgct tctgtgtgcg gtattggcac tgagtcacac agccaacccg      60
tgctgctcac acccatgtca gaatcgggga gtttgcatgt cagtagggtt tgaccaatat     120
aagtgcgact gtacccggac aggcttttat ggagaaaatt gttctacacc cgaatttttg     180
acgaggatta agctctttct gaagcctaca ccaaatacag tccattatat cctcacgcac     240
ttcaagggtt tttggaatgt cgtaaacaac attccgtttc tgagaaatgc gataatgtct     300
tacgtcctta catcccggag ccaccttatt gactcacccc caacatacaa cgccgactac     360
ggatacaaaa gttgggaagc ttttctccaac ctgtcttact acacgcgagc attgcctcct     420
gtacccgacg attgcccgac gccgttgggg gtgaaaggaa aaagcagct cccggactca      480 aacgaaatag tagagaaatt gttgcttcgc cgaaaattta ccagacccg cagggtagc       540 aatatgatgt ttgcgttctt cgctcagcac ttcactcacc aattctttaa gacagaccac     600
aagagaggtc ccgcattcac gaatggcctt ggacacggcg tcgacttgaa ccacatatat     660
ggggagacat tggccagaca aggaaacctt cgattgttta aggatgggaa atgaaatac      720 caaattattg atggcgagat gtatcctcca acagtgaagg atacgcaagc ggagatgatt     780
tatccaccgc aggtaccaga gcatttgcgg ttcgcggtgg ggcaggaagt atttggactt     840 gttccccggtc tgatgatgta cgccacaata tggctccggg agcataatcg cgtgtgtgac     900
gtacttaagc aagagcaccc ggaatggggc gacgagcaac ttttcaaac gagtcgactg      960 attctcattg gggaaacgat taaaatagtg atcgaagatt atgtgcaaca tctttctggt    1020
taccacttta gttgaagttc gatcctgag ctgcttttca ataaacaatt ccagtatcaa      1080
aacagaatcg ccgcggagtt caacacgctg tatcattggc atcccctgtt gcccgatact    1140
tttcaaatcc atgaccagaa atacaattac cagcaattta tatataataa ctctatcctc    1200
```

```
ctggagcatg gcattacaca attcgttgaa agtttcacaa ggcagatcgc aggaagagtt    1260
gcgggtggcc ggaatgtgcc gcctgccgtg caaaaggtat cacaggctag catcgaccaa    1320
tcaaggcaaa tgaagtacca gtctttaat gagtacagga aaaggttcat gctgaagcct     1380
tacgagagct ttgaagaact gacgggcgaa aaggaaatgt ccgcggaact ggaagcgttg    1440
tacggagata ttgatgcggt agagctctac cccgcgcttc tggtcgaaaa gccccggcca    1500
gatgccattt tcggggaaac catggttgaa gtgggcgccc cattcagttt gaaaggtctg    1560
atgggtaatg taatttgcag tccggcgtac tggaagcctt ccacttttgg tggggaagtg    1620
gggtttcaaa ttatcaatac ggcctcaatt cagtctctga tttgtaacaa tgttaaggga    1680 tgtccctta catcttttag tgtaccggac cccgagctta ttaagaccgt gaccataaat     1740
gcttcaagct ctagaagtgg tcttgatgat atcaaccca cagttttgct taaggaaagg     1800
agcacggagc tc                                                        1812

<210> SEQ ID NO 56
<211> LENGTH: 66
<212> TYPE: DNA
<213> ORGANISM: Artificial Sequence
<220> FEATURE:
<223> OTHER INFORMATION: synthetic

<400> SEQUENCE: 56
ggaagcggag ctactaactt cagcctgctg aagcaggctg agacgtcga ggagaaccct       60 ggacct                                                                66

<210> SEQ ID NO 57
<211> LENGTH: 891
<212> TYPE: DNA
<213> ORGANISM: Artificial Sequence
<220> FEATURE:
<223> OTHER INFORMATION: synthetic

<400> SEQUENCE: 57
agcatgaaca actcaaaaca gttggtctcc ccagcagcgg ccctttttgtc caacacaacg      60 tgtcagactg agaatagact cagtgtattt tttagcgtga ttttttatgac cgtcggtatc    120 ctgtctaact ctcttgccat agcaatattg atgaaagcct atcagcgatt ccggcaaaag    180
tctaaggcgt catttttgtt gttggcaagc gggcttgtca tcacggactt tttcgggcac    240
ctcattaacg gagccatagc cgtgttcgtt tatgcttcag acaaagagtg gatacgattc    300
gatcagagca atgtgctttg cagtatcttt ggcatatgta tggtgtttag tggattgtgt    360
ccactcttgc ttgggagcgt gatggctatt gaaagatgca tcggggtgac taaacctatc    420
tttcacagta ccaaaattac atctaagcac gtcaagatga tgttgtccgg ggtgtgtctt    480
tttgctgtct ttattgcgtt gttgccaata ctgggccaca gggactacaa aattcaggcc    540
tcacgcactt ggtgcttcta taacactgag gatattaaag actgggagga taggttttat    600
cttcttcttt tctcattcct cggtctgctc gcactggggg tatcccttt gtgtaacgct    660 atcacaggta tcaccttgtt gcgcgttaaa tttaagagcc aacagcatcg ccaggggagg    720
tcacatcacc tcgaaatggt aatacagttg ctcgcgatca tgtgtgttag ttgtatctgc    780
tggtcaccct tcttgggata tagaataatt ctgaatggaa agaaaagta caaagtctat    840 gaagaacaga gcgattttct gcatcgattg caatggccca ctttggaata a              891

<210> SEQ ID NO 58
```

<211> LENGTH: 4621
<212> TYPE: DNA
<213> ORGANISM: Artificial Sequence
<220> FEATURE:
<223> OTHER INFORMATION: synthetic

<400> SEQUENCE: 58

| | | | | | |
|---|---|---|---|---|---|
| ggttggccac | tccctctctg | cgcgctcgct | cgctcactga | ggccgggcga | ccaaaggtcg | 60 |
| cccgacgccc | gggctttgcc | cgggcggcct | cagtgagcga | gcgagcgcgc | agagagggag | 120 |
| tggccaactc | catcactagg | ggttcctaga | tctgaattcg | gtaccoctag | ttattaatag | 180 |
| taatcaatta | cggggtcatt | agttcatagc | ccatatatgg | agttccgcgt | tacataactt | 240 |
| acggtaaatg | gcccgcctgg | ctgaccgccc | aacgaccccc | gcccattgac | gtcaataatg | 300 |
| acgtatgttc | ccatagtaac | gccaataggg | actttccatt | gacgtcaatg | ggtggactat | 360 |
| ttacggtaaa | ctgcccactt | ggcagtacat | caagtgtatc | atatgccaag | tacgccccct | 420 |
| attgacgtca | atgacggtaa | atggcccgcc | tggcattatg | cccagtacat | gaccttatgg | 480 |
| gactttccta | cttggcagta | catctacgta | ttagtcatcg | ctattaccat | ggtcgaggtg | 540 |
| agccccacgt | tctgcttcac | tctccccatc | tcccccccct | ccccaccccc | aattttgtat | 600 |
| ttatttattt | tttaattatt | ttgtgcagcg | atggggggcgg | gggggggggg | ggggcgcgcg | 660 |
| ccaggcgggg | cggggcgggg | cgaggggcgg | ggcggggcga | ggcggagagg | tgcggcggca | 720 |
| gccaatcaga | gcggcgcgct | ccgaaagttt | cctttatgg | cgaggcggcg | gcggcggcgg | 780 |
| ccctataaaa | agcgaagcgc | gcggcgggcg | ggagtcgctg | cgacgctgcc | ttcgccccgt | 840 |
| gccccgctcc | gccgccgcct | cgcgccgccc | gccccggctc | tgactgaccg | cgttactccc | 900 |
| acaggtgagc | gggcgggacg | gcccttctcc | tccgggctgt | aattagcgct | tggtttaatg | 960 |
| acggcttgtt | tcttttctgt | ggctgcgtga | aagccttgag | gggctccggg | agctagagcc | 1020 |
| tctgctaacc | atgttcatgc | cttcttcttt | ttcctacagc | tcctgggcaa | cgtgctggtt | 1080 |
| attgtgctgt | ctcatcattt | tggcaaagaa | ttcctcgaag | atctaggcaa | ctcgagaaac | 1140 |
| aaacaaactg | aggtgcaggt | acatccagct | gacgagtccc | aaataggacg | aaagggagag | 1200 |
| gtgaagaata | cgaccaccta | ggctcgaaag | agctaaaaac | ataccttcct | ggattccact | 1260 |
| gctatccaca | aaaagaaaaa | taaaaagcca | ccatgcttgc | ccgggccctg | cttctgtgtg | 1320 |
| cggtattggc | actgagtcac | acagccaacc | cgtgctgctc | acaccatgt | cagaatcggg | 1380 |
| gagtttgcat | gtcagtaggg | tttgaccaat | ataagtgcga | ctgtacccgg | acaggctttt | 1440 |
| atggagaaaa | ttgttctaca | cccgaatttt | tgacgaggat | taagctcttt | ctgaagccta | 1500 |
| caccaaatac | agtccattat | atcctcacgc | acttcaaggg | ttttggaat | gtcgtaaaca | 1560 |
| acattccgtt | tctgagaaat | gcgataatgt | cttacgtcct | tacatcccgg | agccaccta | 1620 |
| ttgactcacc | cccaacatac | aacgccgact | acggatacaa | aagttgggaa | gctttctcca | 1680 |
| acctgtctta | ctacacgcga | gcattgcctc | ctgtacccga | cgattgcccg | acgccgttgg | 1740 |
| gggtgaaagg | aaaaaagcag | ctcccggact | caaacgaaat | agtagagaaa | ttgttgcttc | 1800 |
| gccgaaaatt | tataccagac | ccgcagggta | gcaatatgat | gttcgttc | ttcgctcagc | 1860 |
| acttcactca | ccaattcttt | aagacagacc | acaagagagg | tcccgcattc | acgaatggcc | 1920 |
| ttggacacgg | cgtcgacttg | aaccacatat | atggggagac | attggccaga | caaaggaaac | 1980 |
| ttcgattgtt | taaggatggg | aaaatgaaat | accaaattat | tgatggcgag | atgtatcctc | 2040 |
| caacagtgaa | ggatacgcaa | gcggagatga | tttatccacc | gcaggtacca | gagcatttgc | 2100 |
| ggttcgcggt | ggggcaggaa | gtatttggac | ttgttcccgg | tctgatgatg | tacgccacaa | 2160 |

```
tatggctccg ggagcataat cgcgtgtgtg acgtacttaa gcaagagcac cggaatggg    2220 gcgacgagca acttttttcaa acgagtcgac tgattctcat tggggaaacg attaaaatag   2280
tgatcgaaga ttatgtgcaa catctttctg gttaccactt taagttgaag ttcgatcctg   2340
agctgctttt caataaacaa ttccagtatc aaaacagaat cgccgcggag ttcaacacgc   2400
tgtatcattg gcatccctg ttgcccgata cttttcaaat ccatgaccag aaatacaatt    2460
accagcaatt tatatataat aactctatcc tcctggagca tggcattaca caattcgttg   2520
aaagtttcac aaggcagatc gcaggaagag ttgcgggtgg ccggaatgtg ccgcctgccg   2580
tgcaaaaggt atcacaggct agcatcgacc aatcaaggca aatgaagtac cagtcttttta  2640 atgagtacag gaaaaggttc atgctgaagc cttacgagag ctttgaagaa ctgacgggcg   2700
aaaaggaaat gtccgcggaa ctggaagcgt gtacggaga tattgatgcg gtagagctct    2760
accccgcgct tctggtcgaa aagccccggc cagatgccat tttcggggaa accatggttg   2820
aagtgggcgc cccattcagt ttgaaaggtc tgatgggtaa tgtaatttgc agtccggcgt   2880
actggaagcc ttccactttt ggtggggaag tggggtttca aattatcaat acggcctcaa   2940
ttcagtctct gatttgtaac aatgttaagg gatgtcccct tacatctttt agtgtaccgg   3000
accccgagct tattaagacc gtgaccataa atgcttcaag ctctagaagt ggtcttgatg   3060
atatcaaccc cacagttttg cttaaggaaa ggagcacgga gctcggaagc ggagctacta   3120
acttcagcct gctgaagcag gctggagacg tcgaggagaa ccctggacct agcatgaaca   3180
actcaaaaca gttggtctcc ccagcagcgg ccttttgtc caacacaacg tgtcagactg     3240
agaatagact cagtgtattt tttttagcgtga tttttatgac cgtcggtatc ctgtctaact   3300
ctcttgccat agcaatattg atgaaagcct atcagcgatt ccgcaaaag tctaaggcgt    3360 cattttttgtt gttggcaagc gggcttgtca tcacggactt tttcgggcac ctcattaacg   3420
gagccatagc cgtgttcgtt tatgcttcag acaaagagtg gatacgattc gatcagagca   3480
atgtgctttg cagtatcttt ggcatatgta tggtgtttag tggattgtgt ccactcttgc    3540
ttgggagcgt gatggctatt gaaagatgca tcggggtgac taaacctatc tttcacagta   3600
ccaaaattac atctaagcac gtcaagatga tgttgtccgg ggtgtgtctt tttgctgtct    3660
ttattgcgtt gttgccaata ctgggccaca gggactacaa aattcaggcc tcacgcactt    3720
ggtgcttcta taacactgag gatattaaag actggggagga taggttttat cttcttcttt  3780
tctcattcct cggtctgctc gcactggggg tatccctttt gtgtaacgct atcacaggta   3840
tcaccttgtt gcgcgttaaa tttaagagcc aacagcatcg ccaggggagg tcacatcacc    3900
tcgaaatggt aatacagttg ctcgcgatca tgtgtgttag ttgtatctgc tggtcaccct    3960
tcttgggata tagaataatt ctgaatgaa agaaaagta caaagtctat gaagaacaga     4020 gcgatttttct gcatcgattg caatggccca ctttggaata aaaacaaaca aactgagatg   4080
caggtacatc ccactgatga gtcccaaata ggacgaaagg gagaggtgaa gaatacgacc   4140
acctaggctc gaaagagcct aaaacatacc ttctgggatt ccactgctat ccacaaaaag   4200
aaaaataaaa agcggccgct gcaggagtcg gtcgactaga gctcgctgat cagcctcgac   4260
tgtgccttct agttgccagc catctgttgt ttgcccctcc ccgtgccctt ccttgaccct    4320
ggaaggtgcc actcccactg tcctttccta taaaatgag gaaattgcat cgcattgtct   4380
gagtaggtgt cattctattc tggggggtgg ggtggggcag gacagcaagg gggaggattg    4440
ggaagacaat agcaggcatg ctggggagag atctaggaac ccctagtgat ggagttggcc   4500
```

```
actccctctc tgcgcgctcg ctcgctcact gaggccgccc gggcaaagcc cgggcgtcgg    4560
gcgacctttg gtcgcccggc ctcagtgagc gagcgagcgc gcagagaggg agtggccaac    4620
c                                                                    4621
```

<210> SEQ ID NO 59
<211> LENGTH: 122
<212> TYPE: DNA
<213> ORGANISM: Artificial Sequence
<220> FEATURE:
<223> OTHER INFORMATION: synthetic

<400> SEQUENCE: 59

```
ctgaggtgca ggtacatcca gctgacgagt cccaaatagg acgaaaggga gaggtgaaga     60
atacgaccac ctaggctcga aagagcctaa aacatacctt cctggattcc actgctatcc    120
ac                                                                   122
```

<210> SEQ ID NO 60
<211> LENGTH: 1812
<212> TYPE: DNA
<213> ORGANISM: Artificial Sequence
<220> FEATURE:
<223> OTHER INFORMATION: synthetic

<400> SEQUENCE: 60

```
atgcttgccc gggccctgct tctgtgtgcg gtattggcac tgagtcacac agccaacccg     60
tgctgctcac acccatgtca gaatcgggga gtttgcatgt cagtagggtt tgaccaatat    120
aagtgcgact gtaccggac aggcttttat ggagaaaatt gttctacacc gaatttttg     180 acgaggatta agctctttct gaagcctaca ccaaatacag tccattatat cctcacgcac    240
ttcaagggtt tttggaatgt cgtaaacaac attccgtttc tgagaaatgc gataatgtct    300
tacgtcctta catcccggag ccaccttatt gactcacccc caacatacaa cgccgactac    360
ggatacaaaa gttgggaagc tttctccaac ctgtcttact acacgcgagc attgcctcct    420
gtacccgacg attgcccgac gccgttgggg gtgaaaggaa aaagcagct cccggactca    480 aacgaaatag tagagaaatt gttgcttcgc cgaaaatttta taccagaccc gcagggtagc    540
aatatgatgt ttgcgttctt cgctcagcac ttcactcacc aattcttaa gacagaccac    600 aagagaggtc ccgcattcac gaatggcctt ggacacggcg tcgacttgaa ccacatatat    660
ggggagacat tggccagaca aaggaaactt cgattgttta aggatgggaa aatgaaatac    720
caaattattg atggcgagat gtatcctcca acagtgaagg atacgcaagc ggagatgatt    780
tatccaccgc aggtaccaga gcatttgcgg ttcgcggtgg ggcaggaagt atttggactt    840
gttcccggtc tgatgatgta cgccacaata tggctccggg agcataatcg cgtgtgtgac    900
gtacttaagc aagagcaccc ggaatggggc gacgagcaac ttttcaaac gagtcgactg    960 attctcattg ggaaaacgat aaaatagtg atcgaagatt atgtgcaaca tctttctggt    1020 taccactttta agttgaagtt cgatcctgag ctgcttttca ataaacaatt ccagtatcaa    1080
aacagaatcg ccgcggagtt caacacgctg tatcattggc atcccctgtt gcccgatact    1140
tttcaaatcc atgaccagaa atacaattac cagcaattta tatataataa ctctatcctc    1200
ctggagcatg gcattacaca attcgttgaa agtttcacaa ggcagatcgc aggaagagtt    1260
gcgggtggcc ggaatgtgcc gcctgccgtg caaaaggtat cacaggctag catcgaccaa    1320
tcaaggcaaa tgaagtacca gtcttttaat gagtacagga aaaggttcat gctgaagcct    1380
tacgagagct ttgaagaact gacgggcgaa aaggaaatgt ccgcggaact ggaagcgttg    1440
```

```
tacggagata ttgatgcggt agagctctac cccgcgcttc tggtcgaaaa gccccggcca    1500
gatgccattt tcggggaaac catggttgaa gtgggcgccc cattcagttt gaaaggtctg    1560
atgggtaatg taatttgcag tccggcgtac tggaagcctt ccacttttgg tggggaagtg    1620
gggtttcaaa ttatcaatac ggcctcaatt cagtctctga tttgtaacaa tgttaaggga    1680
tgtcccttta catcttttag tgtaccggac cccgagctta ttaagaccgt gaccataaat    1740
gcttcaagct ctagaagtgg tcttgatgat atcaaccccca cagttttgct taaggaaagg    1800
agcacggagc tc                                                        1812

<210> SEQ ID NO 61
<211> LENGTH: 66
<212> TYPE: DNA
<213> ORGANISM: Artificial Sequence
<220> FEATURE:
<223> OTHER INFORMATION: synthetic

<400> SEQUENCE: 61
ggaagcggag ctactaactt cagcctgctg aagcaggctg agacgtcga ggagaaccct     60 ggacct                                                               66

<210> SEQ ID NO 62
<211> LENGTH: 891
<212> TYPE: DNA
<213> ORGANISM: Artificial Sequence
<220> FEATURE:
<223> OTHER INFORMATION: synthetic

<400> SEQUENCE: 62
agcatgaaca actcaaaaca gttggtctcc ccagcagcgg ccccttttgtc caacacaacg    60 tgtcagactg agaatagact cagtgtattt ttttagcgtga ttttttatgac cgtcggtatc   120 ctgtctaact ctcttgccat agcaatattg atgaaagcct atcagcgatt ccggcaaaag   180
tctaaggcgt cattttttgtt gttggcaagc gggcttgtca tcacggactt tttcgggcac   240
ctcattaacg gagccatagc cgtgttcgtt tatgcttcag acaaagagtg gatacgattc    300
gatcagagca atgtgctttg cagtatcttt ggcatatgta tggtgtttag tggattgtgt   360
ccactcttgc ttgggagcgt gatggctatt gaaagatgca tcggggtgac taaacctatc   420
tttcacagta ccaaaattac atctaagcac gtcaagatga tgttgtccgg ggtgtgtctt   480
tttgctgtct ttattgcgtt gttgccaata ctgggccaca gggactacaa aattcaggcc   540
tcacgcactt ggtgcttcta taacactgag gatattaaag actgggagga taggttttat   600
cttcttcttt tctcattcct cggtctgctc gcactggggg tatcccttt gtgtaacgct    660 atcacaggta tcaccttgtt gcgcgttaaa tttaagagcc aacagcatcg ccaggggagg   720
tcacatcacc tcgaaatggt aatacagttg ctcgcgatca tgtgtgttag ttgtatctgc   780
tggtcaccct tcttgggata tagaataatt ctgaatggaa aagaaaagta caaagtctat   840
gaagaacaga gcgattttct gcatcgattg caatggccca ctttggaata a             891

<210> SEQ ID NO 63
<211> LENGTH: 122
<212> TYPE: DNA
<213> ORGANISM: Artificial Sequence
<220> FEATURE:
<223> OTHER INFORMATION: synthetic

<400> SEQUENCE: 63
```
ctgagatgca ggtacatccc actgatgagt cccaaatagg acgaaaggga gaggtgaaga    60
atacgaccac ctaggctcga aagagcctaa aacataccett ctgggattcc actgctatcc   120
ac                                                                  122

<210> SEQ ID NO 64
<211> LENGTH: 168
<212> TYPE: DNA
<213> ORGANISM: Artificial Sequence
<220> FEATURE:
<223> OTHER INFORMATION: synthetic

<400> SEQUENCE: 64
ctcgaggcga tcgcaaacaa acaaagctgt caccggatgt gctttccggt ctgatgagtc    60
cgttgtccaa taccagcatc gtcttgatgc ccttggcagt ggatggggac ggaggacgaa   120
acagcaaaaa gaaaaataaa aattttttt ttaattaatc ttgggccc                 168

<210> SEQ ID NO 65
<211> LENGTH: 139
<212> TYPE: DNA
<213> ORGANISM: Artificial Sequence
<220> FEATURE:
<223> OTHER INFORMATION: synthetic

<400> SEQUENCE: 65
atggccggca tggtcccagc ctcctcgctg gcgccggctg ggcaaccaca taccagccga    60
aaggcccttg gcaggtgggc gaatgggacg cacaaatctc tctagcttcc cagagagaag   120
cgagagaaaa gtggctctc                                                139

<210> SEQ ID NO 66
<211> LENGTH: 135
<212> TYPE: DNA
<213> ORGANISM: Artificial Sequence
<220> FEATURE:
<223> OTHER INFORMATION: synthetic

<400> SEQUENCE: 66
atggccggca tggtcccagc ctcctcgctg gcgccggctg ggcaatgcta taatcgcgtg    60
gatatggcac gcaagtttct accgggcacc gtaaatgtcc gactagtagc gaatgggacg   120
cacaaatctc tctag                                                    135

<210> SEQ ID NO 67
<211> LENGTH: 134
<212> TYPE: DNA
<213> ORGANISM: Artificial Sequence
<220> FEATURE:
<223> OTHER INFORMATION: synthetic

<400> SEQUENCE: 67
caaacaaaca aaggcgcgtc ctggattcgt ggtaaaacat accagatttc gatctggaga    60
ggtgaagaat acgaccacct gtagtatcca gctgatgagt cccaaatagg acgaaacgcg   120
ctaaacaaac aaac                                                     134

<210> SEQ ID NO 68
<211> LENGTH: 104
<212> TYPE: DNA
<213> ORGANISM: Artificial Sequence
<220> FEATURE:
<223> OTHER INFORMATION: synthetic

<400> SEQUENCE: 68

```
gagagaatct tctttctgtc tataaaagag agaatcttct ttctgtctat aaaagagaga      60
atcttctttc tgtctataaa agagagaatc ttctttctgt ctat                      104
```

<210> SEQ ID NO 69
<211> LENGTH: 124
<212> TYPE: DNA
<213> ORGANISM: Artificial Sequence
<220> FEATURE:
<223> OTHER INFORMATION: synthetic

<400> SEQUENCE: 69

```
gcggccgcgc tagcacgggt cctgatacca gcgtgagcgg agagaatctt ctttctgtct      60
attagtgaag ccacagatgt aatagacaga aagaagattc tctccgccta cgcccttggc     120
agca                                                                  124
```

<210> SEQ ID NO 70
<211> LENGTH: 21
<212> TYPE: DNA
<213> ORGANISM: Artificial Sequence
<220> FEATURE:
<223> OTHER INFORMATION: synthetic

<400> SEQUENCE: 70

```
tatttaggga aggaactcag g                                               21
```

<210> SEQ ID NO 71
<211> LENGTH: 21
<212> TYPE: DNA
<213> ORGANISM: Artificial Sequence
<220> FEATURE:
<223> OTHER INFORMATION: synthetic

<400> SEQUENCE: 71

```
aatacaaacc tgaacaatgg g                                               21
```

<210> SEQ ID NO 72
<211> LENGTH: 21
<212> TYPE: DNA
<213> ORGANISM: Artificial Sequence
<220> FEATURE:
<223> OTHER INFORMATION: synthetic

<400> SEQUENCE: 72

```
agttgagcca agatcgacac g                                               21
```

<210> SEQ ID NO 73
<211> LENGTH: 21
<212> TYPE: DNA
<213> ORGANISM: Artificial Sequence
<220> FEATURE:
<223> OTHER INFORMATION: synthetic

<400> SEQUENCE: 73

```
atctatacta tttagggaag g                                               21
```

<210> SEQ ID NO 74
<211> LENGTH: 21
<212> TYPE: DNA
<213> ORGANISM: Artificial Sequence
<220> FEATURE:
<223> OTHER INFORMATION: synthetic

<400> SEQUENCE: 74

```
agatcgacac gttaactctt g                                              21

<210> SEQ ID NO 75
<211> LENGTH: 21
<212> TYPE: DNA
<213> ORGANISM: Artificial Sequence
<220> FEATURE:
<223> OTHER INFORMATION: synthetic

<400> SEQUENCE: 75
taggtacagc tagatatttg c                                              21

<210> SEQ ID NO 76
<211> LENGTH: 21
<212> TYPE: DNA
<213> ORGANISM: Artificial Sequence
<220> FEATURE:
<223> OTHER INFORMATION: synthetic

<400> SEQUENCE: 76
tcatgacgtc ttaacaaacg g                                              21

<210> SEQ ID NO 77
<211> LENGTH: 21
<212> TYPE: DNA
<213> ORGANISM: Artificial Sequence
<220> FEATURE:
<223> OTHER INFORMATION: synthetic

<400> SEQUENCE: 77
taacaaacgg taaagaaggt g                                              21

<210> SEQ ID NO 78
<211> LENGTH: 21
<212> TYPE: DNA
<213> ORGANISM: Artificial Sequence
<220> FEATURE:
<223> OTHER INFORMATION: synthetic

<400> SEQUENCE: 78
atcaatacga gtcggaaagc g                                              21

<210> SEQ ID NO 79
<211> LENGTH: 21
<212> TYPE: DNA
<213> ORGANISM: Artificial Sequence
<220> FEATURE:
<223> OTHER INFORMATION: synthetic

<400> SEQUENCE: 79
atctaggaca ctcttcgtct g                                              21

<210> SEQ ID NO 80
<211> LENGTH: 13
<212> TYPE: RNA
<213> ORGANISM: Artificial Sequence
<220> FEATURE:
<223> OTHER INFORMATION: Synthetic

<400> SEQUENCE: 80
aaaaaaaaaa aaa                                                       13
```